US007776877B2

(12) United States Patent
Charvat et al.

(10) Patent No.: US 7,776,877 B2
(45) Date of Patent: Aug. 17, 2010

(54) N-(2-(HETARYL)ARYL) ARYLSULFONAMIDES AND N-(2-(HETARYL) HETARYL ARYLSULFONAMIDES

(75) Inventors: Trevor T. Charvat, San Jose, CA (US); Cheng Hu, Menlo Park, CA (US); Anita Melikian, San Francisco, CA (US); Aaron Novack, San Jose, CA (US); Andrew M. K. Pennell, San Francisco, CA (US); Edward J. Sullivan, San Jose, CA (US); William D. Thomas, San Jose, CA (US); Solomon Ungashe, Fremont, CA (US); Penglie Zhang, Foster City, CA (US); Jay Powers, Pacifica, CA (US); Sreenivas Punna, Sunnyvale, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 182 days.

(21) Appl. No.: 12/140,593

(22) Filed: Jun. 17, 2008

(65) Prior Publication Data
US 2009/0005410 A1 Jan. 1, 2009

Related U.S. Application Data

(60) Provisional application No. 61/046,291, filed on Apr. 18, 2008, provisional application No. 60/948,796, filed on Jul. 10, 2007, provisional application No. 60/945,849, filed on Jun. 22, 2007.

(51) Int. Cl.
*A01N 43/42* (2006.01)
*A61K 31/44* (2006.01)
*C07D 513/02* (2006.01)
*C07D 515/02* (2006.01)
(52) U.S. Cl. .................................. 514/300; 546/117
(58) Field of Classification Search ............. 546/117; 514/300
See application file for complete search history.

(56) References Cited

U.S. PATENT DOCUMENTS

| 3,817,837 | A | 6/1974 | Rubenstein |
| 3,850,752 | A | 11/1974 | Schuurs et al. |
| 3,939,350 | A | 2/1976 | Kronick et al. |
| 3,996,345 | A | 12/1976 | Ullman et al. |
| 4,166,452 | A | 9/1979 | Generales, Jr. |
| 4,256,108 | A | 3/1981 | Theeuwes |
| 4,275,149 | A | 6/1981 | Litman et al. |
| 4,277,437 | A | 7/1981 | Maggio |
| 4,366,241 | A | 12/1982 | Tom et al. |
| 5,120,643 | A | 6/1992 | Ching et al. |
| 5,990,479 | A | 11/1999 | Weiss et al. |
| 6,207,392 | B1 | 3/2001 | Weiss et al. |
| 6,251,303 | B1 | 6/2001 | Bawendi et al. |
| 6,306,610 | B1 | 10/2001 | Bawendi et al. |
| 6,312,914 | B1 | 11/2001 | Kardos et al. |
| 6,319,426 | B1 | 11/2001 | Bawendi et al. |
| 6,322,901 | B1 | 11/2001 | Bawendi et al. |
| 6,326,144 | B1 | 12/2001 | Bawendi et al. |
| 6,403,607 | B1 | 6/2002 | Hidaka et al. |
| 6,423,551 | B1 | 7/2002 | Weiss et al. |
| 6,444,143 | B2 | 9/2002 | Bawendi et al. |
| 6,451,339 | B2 | 9/2002 | Patel et al. |
| 6,939,885 | B2 | 9/2005 | Ungashe et al. |
| 7,227,035 | B2 | 6/2007 | Ungashe et al. |
| 7,718,683 | B2 | 5/2010 | Charvat et al. |
| 2004/0167113 | A1 | 8/2004 | Ugashe et al. |
| 2004/0171654 | A1 | 9/2004 | Ugashe et al. |
| 2005/0009871 | A1 | 1/2005 | Ramesh et al. |
| 2005/0137193 | A1 | 6/2005 | Ungashe et al. |
| 2005/0165067 | A1 | 7/2005 | Ungashe et al. |
| 2006/0111351 | A1 | 5/2006 | Ungashe et al. |
| 2006/0173019 | A1 | 8/2006 | Ungashe et al. |
| 2006/0183751 | A1 | 8/2006 | Hu et al. |
| 2007/0021466 | A1 | 1/2007 | Ungashe et al. |
| 2007/0037794 | A1 | 2/2007 | Ungashe et al. |
| 2007/0203131 | A1 | 8/2007 | Ungashe et al. |
| 2008/0039465 | A1 | 2/2008 | Charvat et al. |
| 2008/0039504 | A1 | 2/2008 | Charvat et al. |
| 2008/0161345 | A1 | 7/2008 | Ungashe et al. |
| 2009/0048301 | A1 | 2/2009 | Chen et al. |

FOREIGN PATENT DOCUMENTS

DE 3544409 A1 12/1985

(Continued)

OTHER PUBLICATIONS

Maquestiau et al., Rapid Communications in Mass Spectrometry (1989), 3(9), 320-2.*
Bendele et al., *Arthritis. Rheum.* 42:498-506 (1999).
Bendele et al., *Toxicologic Pathol.* 27:134-142 (1999).
Berge, S.M. et al, "Pharmaceutical Salts", J. *Pharmaceutical Science*, 1977, 66:1-19.
Berman et al., *Immunol. Invest.*, 17:625-677 (1988).
Campbell et al., J. *Exp. Med.*, 195(1):135-141 (2002).
Cheeseman, G.W.H. et al., "Synthesis of 5,6-dihydropyrrolo[1,2-a][3,1,6]thiadiazocines", Journal of Heterocyclic Chemistry, 22(2), 423-7, 1985.
Dahinden et al., J. *Exp. Med.*, 179:751-756 (1994).
Davidson et al., *J Exp Med.*, 184(1):241-51(1986).
Diamond et al., *Am. J. Physiol.*, 266:F926-33 (1994).

(Continued)

*Primary Examiner*—D. Margaret Seaman
*Assistant Examiner*—Niloofar Rahmani
(74) *Attorney, Agent, or Firm*—Brinks Hofer Gilson & Lione

(57) ABSTRACT

Compounds are provided that act as potent antagonists of the CCR9 receptor. Animal testing demonstrates that these compounds are useful for treating inflammation, a hallmark disease for CCR9. The compounds are generally aryl sulfonamide derivatives and are useful in pharmaceutical compositions, methods for the treatment of CCR9-mediated diseases, and as controls in assays for the identification of CCR9 antagonists.

6 Claims, No Drawings

FOREIGN PATENT DOCUMENTS

| | | |
|---|---|---|
| GB | 2376691 | 12/2002 |
| WO | WO 93/09780 | 5/1993 |
| WO | WO 94/20142 | 9/1994 |
| WO | WO 98/11218 | 3/1998 |
| WO | WO 99/02502 A2 | 1/1999 |
| WO | WO 01/77087 A1 | 10/2001 |
| WO | WO 03/045393 A1 | 6/2003 |
| WO | WO 03/057225 A2 | 7/2003 |
| WO | WO 03/099773 A1 | 12/2003 |
| WO | WO 2004/058741 A1 | 7/2004 |
| WO | WO 2004/073634 A2 | 9/2004 |
| WO | WO 2004/085384 A2 | 10/2004 |
| WO | WO 2005/004810 A2 | 1/2005 |
| WO | WO 2005/004818 A2 | 1/2005 |
| WO | WO 2005/113513 A2 | 12/2005 |
| WO | WO 2006/076644 A2 | 7/2006 |
| WO | WO 2007/014008 A2 | 1/2007 |
| WO | WO 2007/014054 A2 | 1/2007 |
| WO | WO 2008/008374 A2 | 1/2008 |
| WO | WO 2008/008375 A2 | 1/2008 |
| WO | WO 2008/008431 A2 | 1/2008 |
| WO | WO 2008/089005 A2 | 7/2008 |

OTHER PUBLICATIONS

Dubey, P.K. et al., "Aroylation of o-phenylenediamine and subsequent reactions with electrophiles", Indian Journal of Chemistry, Section B: Organic Chemistry Including Medicinal Chemistry, 41B(6), 1305-1309; (Jun. 2002).
Eddy & Giachelli, *Kidney Int.*, 47:1546-57 (1995).
Gonzalez-Cuadrado et al. *Clin. Exp. Immunol.*, 106:518-22 (1996).
International Application No. PCT/US2007/015808 Search Report.
Kavanaugh et al., J. *Immunol.*, 146:4149-4156 (1991).
Kontoyiannis et al., Immunity, 10(3):387-98 (1999).
Kontoyiannis et al., J. *Exp. Med.*, vol. 196, No. 12, Dec. 16, 2002.
Kosiewicz et al., *J Clin. Invest.*, 107(6):695-702 (2001).
Kunkel et al., J. *Exp. Med.*, 192(5):761-768 (2000).
Lloyd et al. J. *Exp. Med.*, 185:1371-80 (1997).
Morii et al., J. *Diabetes Complications*, 17:11-5 (2003).
Neote et al., *Cell*, 72:415425 (1993).
Panwala et al., J Immunol., 161(10):5733-44 (1998).
Papadakis et al., *Gastroenterology*, 121(2):246-254 (2001).
Papadakis et al., J. *Immunol.*, 165(9):5069-5076 (2000).
Powrie et al., *Int. Immunol.*, 5(11):1461-71 (1993).
Registry No. 349404-57-5, entered into Registry file on STN on Jul. 29, 2001.
Rivera-Nieves et al., *Gastroenterology*, Nov. 2006;131(5):1518-29.
Schall, *Cytokine*, 3:165-183 (1991), Schall et al., *Curr. Opin. Immunol.*, 6:865-873 (1994).
Science IP Jun. 29, 2007—Search Report.
Segerer et al., J. *Am. Soc. Nephrol.*, 11:152-76 (2000).
Targan et al., N. Engl. J Med., 337(15):1029-35 (1997).
Trentham et al., J. *Exp. Med.* 146(3):857-868 (1977).
U.S. Appl. No. 12/753,342, filed Apr. 2, 2010.
Uehara et al., J. *Immunol*, 168(6):2811-2819 (2002).
Van Riper et al., J. *Exp. Med.*, 177:851-856 (1993).
Wurbel et al., *Blood*, 98(9):2626-2632 (2001).
Zaballos et al., J. *Immunol.*, 162(10):5671-5675 (1999).
Cook, A.H. et al., "Sulfonamides Derived from Substituted Anilines", *Journal of the Chemical Society*, pp. 182-185, 1945.
Registry No. 460334-45-6, entered into Registry file on STN on Oct. 10, 2002.
PCT International Search Report for PCT/US2005/016544; Mailing date of Nov. 16, 2005.
PCT International Written Opinion for PCT/US2005/016544; Mailing date of Nov. 16, 2005.

\* cited by examiner

N-(2-(HETARYL)ARYL) ARYLSULFONAMIDES AND N-(2-(HETARYL) HETARYL ARYLSULFONAMIDES

CROSS-REFERENCES TO RELATED APPLICATIONS

The present patent document claims the benefit of the filing dates under 35 U.S.C. §119(e) of the following U.S. Provisional Patent Application Ser. Nos. 61/046,291, filed Apr. 18, 2008, 60/948,796, filed Jul. 10, 2007; and 60/945,849, filed Jun. 22, 2007, each of which is hereby incorporated by reference in its entirety.

FEDERALLY SPONSORED RESEARCH OR DEVELOPMENT

The present invention described herein was supported at least in part by NIH (U19-AI056690-01). The government may have certain rights in the invention.

BACKGROUND

The present invention provides compounds, pharmaceutical compositions containing one or more of those compounds or their pharmaceutically acceptable salts, which are effective in inhibiting the binding or function of various chemokines to chemokine receptors. As antagonists or modulators of chemokine receptors, the compounds and compositions have utility in treating various immune disorder conditions and diseases.

Chemokines, also known as chemotactic cytokines, are a group of small molecular-weight proteins that are released by a wide variety of cells and have a variety of biological activities. Chemokines attract various types of cells of the immune system, such as macrophages, T cells, eosinophils, basophils and neutrophils, and cause them to migrate from the blood to various lymphoid and none-lymphoid tissues. They mediate infiltration of inflammatory cells to sites of inflammation, and are responsible for the initiation and perpetuation of many inflammation diseases (reviewed in Schall, *Cytokine*, 3:165-183 (1991), Schall et al., *Curr. Opin. Immunol.*, 6:865-873 (1994)).

In addition to stimulating chemotaxis, chemokines can induce other changes in responsive cells, including changes in cell shape, granule exocytosis, integrin up-regulation, formation of bioactive lipids (e.g., leukotrienes), respiratory burst associated with leukocyte activation, cell proliferation, resistance to induction of apoptosis and angiogenesis. Thus, chemokines are early triggers of the inflammatory response, causing inflammatory mediator release, chemotaxis and extravasation to sites of infection or inflammation. They are also stimulators of a multitude of cellular processes that bear important physiological functions as well as pathological consequences.

Chemokines exert their effects by activating chemokine receptors expressed by responsive cells. Chemokine receptors are a class of G-protein coupled receptors, also known as seven-transmembrane receptors, found on the surface of a wide variety of cell types such as leukocytes, endothelial cells, smooth muscle cells and tumor cells.

Chemokines and chemokine receptors are expressed by intrinsic renal cells and infiltrating cells during renal inflammation (Segerer et al., *J. Am. Soc. Nephrol.*, 11:152-76 (2000); Morii et al., *J. Diabetes Complications*, 17:11-5 (2003); Lloyd et al. *J. Exp. Med.*, 185:1371-80 (1997); Gonzalez-Cuadrado et al. *Clin. Exp. Immunol.*, 106:518-22 (1996); Eddy & Giachelli, *Kidney Int.*, 47:1546-57 (1995); Diamond et al., *Am. J. Physiol.*, 266:F926-33 (1994)).

T lymphocyte (T cell) infiltration into the small intestine and colon has been linked to the pathogenesis of Coeliac diseases, food allergies, rheumatoid arthritis, human inflammatory bowel diseases (IBD) which include Crohn's disease and ulcerative colitis. Blocking trafficking of relevant T cell populations to the intestine can lead to an effective approach to treat human IBD. More recently, chemokine receptor 9 (CCR9) has been noted to be expressed on gut-homing T cells in peripheral blood, elevated in patients with small bowel inflammation such as Crohn's disease and celiac disease. The only CCR9 ligand identified to date, TECK (thymus-expressed chemokine) is expressed in the small intestine and the ligand receptor pair is now thought to play a pivotal role in the development of IBD. In particular, this pair mediates the migration of disease causing T cells to the intestine. See for example, Zaballos et al., *J. Immunol.*, 162(10):5671-5675 (1999); Kunkel et al., *J. Exp. Med.*, 192(5):761-768 (2000); Papadakis et al., *J. Immunol.*, 165(9):5069-5076 (2000); Papadakis et al., *Gastroenterology*, 121(2):246-254 (2001); Campbell et al., *J. Exp. Med.*, 195(1):135-141 (2002); Wurbel et al., *Blood*, 98(9):2626-2632 (2001); and Uehara et al., *J. Immunol*, 168(6):2811-2819 (2002); Rivera-Nieves et al., *Gastroenterology*, 2006 November; 131(5):1518-29; and Kontoyiannis et al., *J. Exp. Med.*, Vol. 196, Number 12, Dec. 16, 2002. In addition CCR9 bearing lymphocytes have been show to mediate the pathology of filariasis (lymphatic filarial disease) and inhibition of CCR9 has been correlated with reduction of the pathology associated with such conditions. See for example Babu et al., Journal of Infectious Diseases, 191: 1018-26, 2005.

The identification of compounds that modulate the function of CCR9 represents an attractive new family of therapeutic agents for the treatment of inflammatory and other conditions and diseases associated with CCR9 activation, such as inflammatory bowel disease.

PCT Published Application WO 2003/099773 (Millennium Pharmaceuticals, Inc.) discloses compounds which can bind to CCR9 receptors of the formula

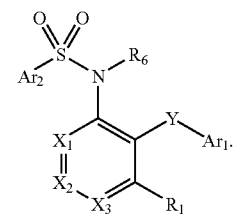

PCT Published Application WO 2005/004810 (Merck & Co., Inc.) discloses brandykinin B1 antagonists or inverse agonists of the formula

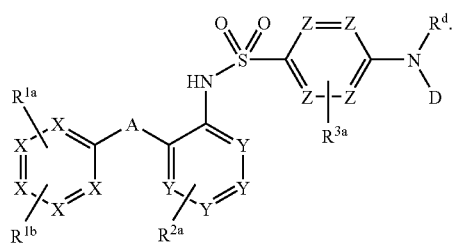

PCT Published Application WO 2005/113513 (ChemoCentryx, Inc.) discloses compounds that modulate various chemokine receptors.

BRIEF SUMMARY

The present invention is directed to compounds and pharmaceutically acceptable salts thereof, compositions, and methods useful in modulating chemokine activity. The compounds and salts thereof, compositions, and methods described herein are useful in treating or preventing chemokine-mediated conditions or diseases, including certain inflammatory and immunoregulatory disorders and diseases.

The compounds of the present invention have been shown to modulate one or more of CCR2, CCR3, CCR4, CCR5, CCR6, CCR7, CCR8, CCR9, CCR10, CXCR3, CXCR4, CXCR5, and CX3CR1. In particular, various compounds of the present invention modulate CCR9 as shown in the examples.

The compounds of the present invention are represented by formulae (I)-(VIII), (CI)-(CVII) and (CCI)-(CCVI), described below.

In another aspect, the present invention provides compositions useful in modulating chemokine activity. In one embodiment, a composition according to the present invention comprises a compound according to the invention and a pharmaceutically acceptable carrier or excipient.

In yet another aspect, the present invention provides methods of modulating chemokine function in a cell, comprising contacting the cell with a therapeutically effective amount of a compound or composition according to the invention.

In still another aspect, the present invention provides methods for modulating chemokine function, comprising contacting a chemokine receptor with a therapeutically effective amount of a compound or composition according to the invention.

In still another aspect, the present invention provides methods for treating a chemokine-mediated condition or disease, comprising administering to a subject a safe and effective amount of a compound or composition according to the invention. The administering may be oral, parenteral, rectal, transdermal, sublingual, nasal or topical. In some aspects the compound may be administered in combination with an anti-inflammatory or analgesic agent.

In addition to the compounds provided herein, the present invention further provides pharmaceutical compositions containing one or more of these compounds, as well as methods for the use of these compounds in therapeutic methods, primarily to treat diseases associated with chemokine signaling activity.

DETAILED DESCRIPTION

General

The present invention is directed to compounds and salts thereof, compositions and methods useful in the modulation of chemokine receptor function, particularly CCR9 function. Modulation of chemokine receptor activity, as used herein in its various forms, is intended to encompass antagonism, agonism, partial antagonism, inverse agonism and/or partial agonism of the activity associated with a particular chemokine receptor, preferably the CCR9 receptor. Accordingly, the compounds of the present invention are compounds which modulate at least one function or characteristic of mammalian CCR9, for example, a human CCR9 protein. The ability of a compound to modulate the function of CCR9, can be demonstrated in a binding assay (e.g., ligand binding or agonist binding), a migration assay, a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like. Additional examples of suitable substituted alkyl include, but are not limited to, hydroxyisoproptyl, —C(CH$_3$)$_2$—OH, aminomethyl, 2-nitroethyl, 4-cyanobutyl, 2,3-dichloropentyl, and 3-hydroxy-5-carboxyhexyl, 2-aminoethyl, pentachloroethyl, trifluoromethyl, 2-diethylaminoethyl, 2-dimethylaminopropyl, ethoxycarbonylmethyl, methanylsulfanylmethyl, methoxymethyl, 3-hydroxypentyl, 2-carboxybutyl, 4-chlorobutyl, and pentafluoroethyl. Suitable substituents for substituted alkyl, include halogen, —CN, —CO$_2$R', —C(O)R', —C(O)NR'R", oxo (=O or —O$^-$), —OR', —OC(O)R', —OC(O)NR'R"—NO$_2$, —NR'C(O)R", —NR'''C(O)NR'R", —NR'R", —NR'CO$_2$R", —NR'S(O)R", —NR'S(O)$_2$R''', —NR'''S(O)NR'R", —NR'''S(O)$_2$NR'R", —SR', —S(O)R', —S(O)$_2$R', —S(O)$_2$NR'R", —NR'—C(NHR")=NR''', —SiR'R"R''', —N$_3$, substituted or unsubstituted $C_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical. With respect to substituted alkyl, R" and R''' each independently refer to a variety of groups including hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6- or 7-membered ring.

"Alkoxy" refers to —O-alkyl. Examples of an alkoxy group include methoxy, ethoxy, n-propoxy etc.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Aryl" refers to a polyunsaturated, aromatic hydrocarbon group having a single ring (monocyclic) or multiple rings (bicyclic), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated.

"Halo" or "halogen", by itself or as part of a substituent refers to a chlorine, bromine, iodine, or fluorine atom.

"Haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic ring containing at least one heteroatom (typically 1 to 5 heteroatoms) selected from nitrogen, oxygen or sulfur. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

In one preferred embodiment, heterocyclic groups may be represented by formula (AA) below:

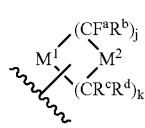

AA where formula (AA) is attached via a free valence on either $M^1$ or $M^2$; $M^1$ represents O, $NR^e$, or $S(O)_l$; $M^2$ represents $CR^fR^g$, O, $S(O)_l$, or $NR^e$; l is 0, 1 or 2; j is 1, 2 or 3 and k is 1, 2 or 3, with the proviso that j+k is 3, 4, or 5; and $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —$COR^h$, —$CO_2R^h$, —$CONR^hR^i$, —$NR^hCOR^i$, —$SO_2R^h$, —$SO_2NR^hR^i$, —$NSO_2R^hR^i$—$NR^hR^i$, —$OR^h$, -$Q^1COR^h$, -$Q^1CO_2R^h$, -$Q^1CONR^hR^i$, -$Q^1NR^hCOR^i$, -$Q^1SO_2R^{28}$, -$Q^1SO_2NR^hR^i$, -$Q^1NSO_2R^hR^i$, -$Q^1NR^hR^i$, -$Q^1OR^h$ wherein $Q^1$ is a member selected from the group consisting of $C_{1-4}$ alkylene, $C_{2-4}$ alkenylene and $C_{2-4}$ alkynylene, and $R^h$ and $R^i$ are independently selected from the group consisting of hydrogen and $C_{1-8}$ alkyl, and wherein the aliphatic portions of each of the $R^a$, $R^b$, $R^c$, $R^d$, $R^e$, $R^f$, $R^g$, $R^h$ and $R^i$ substituents are optionally substituted with from one to three members selected from the group consisting of halogen, —OH, —$OR''$, —OC(O)$NHR''$, —OC(O)$NR''R^o$, —SH, —$SR''$, —$S(O)R''$, —$S(O)_2R''$, —$SO_2NH_2$, —$S(O)_2NHR''$, —$S(O)_2NR''R^o$, —$NHS(O)_2R''$, —$NR''S(O)_2R^o$, —C(O)$NH_2$, —C(O)$NHR''$, —C(O)$NR''R^o$, —$C(O)R''$, —NHC(O)$R^o$, —$NR''C(O)R^o$, —NHC(O)$NH_2$, —$NR''C(O)NH_2$, —$NR''C(O)NHR^o$, —NHC(O)$NHR''$, —$NR''C(O)NR^oR^p$, —NHC(O)$NR''R^o$, —$CO_2H$, —$CO_2R''$, —$NHCO_2R''$, —$NR''CO_2R^o$, —CN, —$NO_2$, —$NH_2$, —$NHR''$, —$NR''R^o$, —$NR''S(O)NH_2$ and —$NR''S(O)_2NHR^o$, wherein $R''$, $R^o$ and $R^p$ are independently an unsubstituted $C_{1-8}$ alkyl. Additionally, any two of $R^a$, $R^b$, $R^c$, $R^d$, $R^f$ and $R^g$ may be combined to form a bridged or spirocyclic ring system.

In one preferred embodiment, the number of $R^a$+$R^b$+$R^c$+$R^d$ groups that are other than hydrogen is 0, 1 or 2. In a more preferred embodiment, $R^a$, $R^b$, $R^c$, $R^d$, $R^e$, $R^f$, and $R^g$ are independently selected from the group consisting of hydrogen, halogen, unsubstituted or substituted $C_{1-8}$ alkyl, —$COR^h$, —$CO_2R^h$, —$CONR^hR^h$, —$NR^hCOR^h$, —$SO_2R^h$, —$SO_2NR^hR^i$, —$NSO_2R^hR^i$, —$NR^hR^i$, and —$OR^h$, wherein $R^h$ and $R^i$ are independently selected from the group consisting of hydrogen and unsubstituted $C_{1-8}$ alkyl and wherein the aliphatic portions of each of the $R^a$, $R^b$, $R^c$, $R^d$, $R^e$, $R^f$ and $R^g$ substituents are optionally substituted with from one to three members selected from the group consisting of halogen, —OH, —$OR''$, —OC(O)$NHR''$, —OC(O)$NR''R^o$, —SH, —$SR''$, —$S(O)R^o$, —$S(O)_2R''$, —$SO_2NH_2$, —$S(O)_2NHR''$, —$S(O)_2NR''R^o$, —$NHS(O)_2R''$, —$NR''S(O)_2R^o$, —C(O)$NH_2$, —C(O)$NHR''$, —C(O)$NR''R^o$, —$C(O)R''$, —NHC(O)$R''$, —$NR''C(O)R^o$, —NHC(O)$NH_2$, —$NR''C(O)NH_2$, —$NR''C(O)NHR^o$, —NHC(O)$NHR''$, —$NR''C(O)NR^oR^p$, —NHC(O)$NR''R^o$, —$CO_2H$, —$CO_2R''$, —$NHCO_2R''$, —$NR''CO_2R^o$, —CN, —$NO_2$, —$NH_2$, —$NHR''$, —$NR''R^o$, —$NR''S(O)NH_2$ and —$NR''S(O)_2NHR^o$, wherein $R''$, $R^o$ and $R^p$ are independently an unsubstituted $C_{1-8}$ alkyl.

In a more preferred embodiment, $R^a$, $R^b$, $R^c$, $R^d$, $R^e$, $R^f$, and $R^g$ are independently hydrogen or $C_{1-4}$ alkyl. In another preferred embodiment, at least three of $R^a$, $R^b$, $R^c$, $R^d$, $R^e$, $R^f$, and $R^g$ are hydrogen.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, azaindolyl, azaindazolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is oxo (=O or —O$^-$), the resulting group may have either a carbonyl (—C(O)—) or a N-oxide (—N$^+$—O$^-$).

Suitable substituents for substituted alkyl, substituted alkenyl, and substituted alkynyl include halogen, —CN, —CO$_2$R', —C(O)R', —C(O)NR'R", oxo (=O or —O$^-$), —OR', —OC(O)R', —OC(O)NR'R"—NO$_2$, —NR'C(O)R", —NR'''C(O)NR'R", —NR'R", —NR'CO$_2$R", —NR'S(O)R", —NR'S(O)$_2$R''', —NR'''S(O)NR'R", —NR'''S(O)$_2$NR'R", —SR', —S(O)R', —S(O)$_2$R', —S(O)$_2$NR'R", —NR'=C(NHR")=NR''', —SiR'R"R''', —N$_3$, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to (2m'+1), where m' is the total number of carbon atoms in such radical.

Suitable substituents for substituted aryl, substituted heteroaryl and substituted heterocyclyl include halogen, —CN, —CO$_2$R', —C(O)R', —C(O)NR'R", oxo (=O or —O$^-$), —OR', —OC(O)R', —OC(O)NR'R", —NO$_2$, —NR'C(O)R", —NR'''C(O)NR'R", —NR'R", —NR'CO$_2$R", —NR'S(O)R", —NR'S(O)$_2$R''', —NR'''S(O)NR'R", —NR'''S(O)$_2$NR'R", —SR', —S(O)R', —S(O)$_2$R', —S(O)$_2$NR'R", —NR'=C(NHR")=NR''', —SiR'R"R''', —N$_3$, substituted or unsubstituted C$_{1-8}$ alkyl, substituted or unsubstituted C$_{2-8}$ alkenyl, substituted or unsubstituted C$_{2-8}$ alkynyl, substituted or unsubstituted C$_{6-10}$ aryl, substituted or unsubstituted 5- to 10-membered heteroaryl, and substituted or unsubstituted 3- to 10 membered heterocyclyl. The number of possible substituents range from zero to the total number of open valences on the aromatic ring system.

As used above, R', R" and R''' each independently refer to a variety of groups including hydrogen, substituted or unsubstituted C$_{1-8}$ alkyl, substituted or unsubstituted C$_{2-8}$ alkenyl, substituted or unsubstituted C$_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl). Furthermore, R' and R", R" and R''', or R' and R''' may together with the atom(s) to which they are attached, form a substituted or unsubstituted 5-, 6- or 7-membered ring.

Two of the substituents on adjacent atoms of an aryl or heteroaryl ring may optionally be replaced with a substituent of the formula -T-C(O)—(CH$_2$)$_q$—U—, wherein T and U are independently —NR""—, —O—, —CH$_2$— or a single bond, and q is an integer of from 0 to 2. Alternatively, two of the substituents on adjacent atoms of the aryl or heteroaryl ring may optionally be replaced with a substituent of the formula -A'-(CH$_2$)$_r$B'—, wherein A' and B' are independently —CH$_2$—, —O—, —NR""—, —S—, —S(O)—, —S(O)$_2$—, —S(O)$_2$NR""— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and XIV is —O—, —NR""—, —S—, —S(O)—, —S(O)$_2$—, or —S(O)$_2$NR'—. R"" in is selected from hydrogen or unsubstituted C$_{1-8}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", J. *Pharmaceutical Science,* 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs may be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The compounds of the invention may be present in the form of pharmaceutically acceptable metabolites thereof. The term "metabolite" means a pharmaceutically acceptable form of a metabolic derivative of a compound of the invention (or a salt thereof). In some aspects, the metabolite may be a functional derivative of a compound that is readily convertible in vivo into an active compound. In other aspects, the metabolite may be an active compound.

"Therapeutically effective amount" refers to an amount sufficient to effect treatment when administered to a patient in need of treatment.

"Treating" or "treatment" as used herein refers to the treating or treatment of a disease or medical condition (such as a viral, bacterial or fungal infection or other infectious diseases, as well as autoimmune or inflammatory conditions) in a patient, such as a mammal (particularly a human or a companion animal) which includes ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

It will be apparent to one skilled in the art that certain compounds of the present invention may exist in tautomeric forms, all such tautomeric forms of the compounds being within the scope of the invention. Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The compounds of the present invention may include a detectable label. A detectable label is a group that is detectable at low concentrations, usually less than micromolar, possibly less than nanomolar, and that can be readily distinguished from other molecules, due to differences in a molecular property (e.g. molecular weight, mass to charge ratio, radioactivity, redox potential, luminescence, fluorescence, electromagnetic properties, binding properties, and the like). Detectable labels may be detected by spectroscopic, photochemical, biochemical, immunochemical, electrical, magnetic, electromagnetic, optical or chemical means and the like.

A wide variety of detectable labels are within the scope of the present invention, including hapten labels (e.g. biotin, or labels used in conjunction with detectable antibodies such as horse radish peroxidase antibodies); mass tag labels (e.g. stable isotope labels); radioisotopic labels (including $^3$H, $^{125}$I, $^{35}$S, $^{14}$C, or $^{32}$P); metal chelate labels; luminescent labels including fluorescent labels (such as fluorescein, isothiocyanate, Texas red, rhodamine, green fluorescent protein, and the like), phosphorescent labels, and chemiluminescent labels, typically having quantum yield greater than 0.1; electroactive and electron transfer labels; enzyme modulator labels including coenzymes, organometallic catalysts horse radish peroxidase, alkaline phosphatase and others commonly used in an ELISA; photosensitizer labels; magnetic bead labels including Dynabeads; calorimetric labels such as colloidal gold, silver, selenium, or other metals and metal sol labels (see U.S. Pat. No. 5,120,643, which is herein incorporated by reference in its entirety for all purposes), or colored glass or plastic (e.g., polystyrene, polypropylene, latex, etc.) bead labels; and carbon black labels. Patents teaching the use of such detectable labels include U.S. Pat. Nos. 3,817,837; 3,850,752; 3,939,350; 3,996,345; 4,277,437; 4,275,149; 4,366,241; 6,312,914; 5,990,479; 6,207,392; 6,423,551; 6,251,303; 6,306,610; 6,322,901; 6,319,426; 6,326,144; and 6,444,143, which are herein incorporated by reference in their entirety for all purposes.

Detectable labels are commercially available or may be prepared as known to one skilled in the art. Detectable labels may be covalently attached to the compounds using a reactive functional group, which can be located at any appropriate position. Methods for attaching a detectable label are known to one skilled in the art. When the reactive group is attached to an alkyl, or substituted alkyl chain tethered to an aryl nucleus, the reactive group may be located at a terminal position of an alkyl chain.

Compounds

The present invention provides compounds that modulate at least one of CCR9 activity. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

For example, compounds of this invention act as potent CCR9 antagonists, and this antagonistic activity has been further confirmed in animal testing for inflammation, one of the hallmark disease states for CCR9. Accordingly, the compounds provided herein are useful in pharmaceutical compositions, methods for the treatment of CCR9-mediated diseases, and as controls in assays for the identification of competitive CCR9 antagonists.

In the formulae set forth below, when a variable appears more than once in the same formula, it can be either the same or different. For example, in formula (II), one $R^4$ can be halogen and the remainder can be hydrogen.

In one embodiment, the compounds of the present invention are represented by formula (I), or salts thereof:

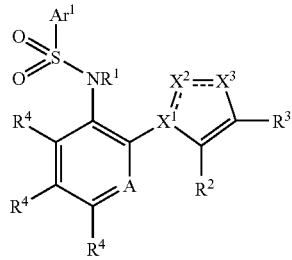

where $Ar^1$ is a substituted or unsubstituted $C_{6-10}$ aryl or substituted or unsubstituted 5- to 10-membered heteroaryl; each having 0 to 5 substituents selected from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, =O, —C(O)R$^3$, —CO$_2$R$^3$, —C(O)NR$^3$R$^4$, —OR$^3$, —OC(O)R$^3$, —OC(O)NR$^3$R$^4$, —NR$^5$C(O)R$^3$, —NR$^5$C(O)NR$^3$R$^4$, —NR$^3$R$^4$, —NR$^5$CO$_2$R$^3$, —NR$^5$S(O)$_2$R$^3$, —SR$^3$, —S(O)R$^3$, —S(O)$_2$R$^3$, —S(O)$_2$NR$^3$R$^4$, substituted or unsubstituted $C_{6-10}$ aryl, substituted or unsubstituted 5- to 10-membered heteroaryl, and substituted or unsubstituted 3- to 10-membered heterocyclyl;

A is N or CR$^4$;

$X^1 = X^2 = X^3$ are selected from the group consisting of:
N—N=N,
C=N—N(R$^5$),
N—C(R$^6$)=N,
N—N=C(R$^7$),
N—C(R$^6$)=C(R$^7$),
C=N—C(R$^7$), and
C=C(R$^6$)—N(R$^5$); (such that = is either a single bond or double bond);

$R^1$ is hydrogen or $C_{1-8}$ alkyl;

each $R^2$, $R^3$, $R^4$, $R^6$ and $R^7$, when present, are independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —NO$_2$, —OR', —OC(O)R', —CO$_2$R', —C(O)R', —C(O)NR"R', —OC(O)NR"R', —NR'''C(O)R', —NR'''C(O)NR"R', —NR"R', —NR"CO$_2$R', —SR', —S(O)R', —S(O)$_2$R', —S(O)$_2$NR"R', —NR"S(O)$_2$R', substituted or unsubstituted $C_{6-10}$ aryl, substituted or unsubstituted 5- to 10-membered heteroaryl and substituted or unsubstituted 3- to 10-membered heterocyclyl; or $R^2$ and $R^3$ together with the atoms which they substitute form a substituted or unsubstituted 5-, 6-, or 7-membered ring;

each $R^5$ is independently selected from group consisting of hydrogen, substituted or unsubstituted $C_{1-8}$ alkyl, substituted or unsubstituted $C_{2-8}$ alkenyl, substituted or unsubstituted $C_{2-8}$ alkynyl, —CO$_2$R', —C(O)R', —C(O)NR"R', —S(O)R', —S(O)$_2$R', —S(O)$_2$NR"R', substituted or unsubstituted $C_{6-10}$ aryl, substituted or unsubstituted 5- to 10-membered heteroaryl, and substituted or unsubstituted 3- to 10-membered heterocyclyl; and R', R" and R''' are each independently hydrogen or unsubstituted $C_{1-4}$ alkyl; or R' and R" together with the atoms which they substitute form a substituted or unsubstituted 5-, 6-, or 7-membered ring.

In one embodiment of the present invention, each $R^2$, $R^3$, $R^4$, $R^6$ and $R^7$, when present, are independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, —OR', —OC(O)R', —CO$_2$R', —C(O)R', —C(O)NR"R', —OC(O)NR"R', —NR'''C(O)R', —NR'''C(O)NR"R', —NR"R', —NR'''CO$_2$R', —SR', —S(O)R', —S(O)$_2$R', —S(O)$_2$NR"R', —NR"S(O)$_2$R', substituted or unsubstituted $C_{6-10}$ aryl, substituted or unsubstituted 5- to 10-membered heteroaryl and substituted or unsubstituted 3- to 10-membered heterocyclyl.

In one embodiment, a compound of the present invention is selected from the group consisting of:
4-tert-butyl-N-(4-chloro-2-(1H-pyrazolo[3,4-b]pyridin-3-yl)phenyl)benzenesulfonamide;
4-tert-butyl-N-(4-chloro-2-(1-methyl-1H-pyrazolo[3,4-b]pyridin-3-yl)phenyl)benzenesulfonamide;
4-tert-butyl-N-(4-chloro-2-(4-(methoxymethyl)-1H-1,2,3-triazol-1-yl)phenyl)benzenesulfonamide;
N-(2-(1H-[1,2,3]triazolo[4,5-b]pyridin-1-yl)-4-chloro-5-fluorophenyl)-4-tert-butylbenzenesulfonamide;
1-(2-(4-tert-butylphenylsulfonamido)-4-chlorophenyl)-N,N-dimethyl-1H-pyrazole-4-carboxamide;
4-tert-butyl-N-(4-chloro-2-(1H-pyrazol-1-yl)phenyl)benzenesulfonamide;
4-tert-butyl-N-(4-chloro-2-(4-chloro-1H-pyrazol-1-yl)phenyl)benzenesulfonamide;
4-tert-butyl-N-(4-chloro-2-(4-isopropyl-1H-1,2,3-triazol-1-yl)phenyl)benzenesulfonamide;
ethyl 1-(2-(4-tert-butylphenylsulfonamido)-5-chlorophenyl)-1H-pyrazole-4-carboxylate;
4-tert-butyl-N-(4-chloro-2-(4-isopropyl-1H-pyrazol-1-yl)phenyl)benzenesulfonamide;
4-tert-butyl-N-(4-chloro-2-(2-methyl-1H-imidazol-1-yl)phenyl)benzenesulfonamide;
4-tert-butyl-N-(4-chloro-2-(2-isopropyl-1H-imidazol-1-yl)phenyl)benzenesulfonamide;
4-tert-butyl-N-(4-chloro-2-(1H-indol-1-yl)phenyl)benzenesulfonamide;
4-tert-butyl-N-(4-chloro-2-(1H-imidazo[4,5-b]pyridin-1-yl)phenyl)benzenesulfonamide;
4-tert-butyl-N-(4-chloro-2-(1H-indazol-1-yl)phenyl)benzenesulfonamide;
N-(2-(1H-benzo[d][1,2,3]triazol-1-yl)-4-chlorophenyl)-4-tert-butylbenzenesulfonamide;

4-tert-butyl-N-(4-chloro-2-(9H-purin-9-yl)phenyl)benzenesulfonamide;
4-tert-butyl-N-(4-chloro-2-(7H-purin-7-yl)phenyl)benzenesulfonamide;
4-tert-butyl-N-(4-chloro-2-(2-ethyl-1H-imidazol-1-yl)phenyl)benzenesulfonamide;
4-tert-butyl-N-(4-chloro-2-(2,4-dimethyl-1H-imidazol-1-yl)phenyl)benzenesulfonamide;
4-tert-butyl-N-(4-chloro-2-(2-ethyl-4-methyl-1H-imidazol-1-yl)phenyl)benzenesulfonamide;
4-tert-butyl-N-(4-chloro-2-(1H-imidazo[4,5-b]pyridin-1-yl)phenyl)benzenesulfonamide;
4-tert-butyl-N-(4-chloro-2-(3H-imidazo[4,5-b]pyridin-3-yl)phenyl)benzenesulfonamide;
N-(2-(2-amino-7H-purin-7-yl)-4-chlorophenyl)-4-tert-butylbenzenesulfonamide;
N-(2-(1H-[1,2,3]triazolo[4,5-b]pyridin-1-yl)-4-chlorophenyl)-4-tert-butylbenzenesulfonamide;
N-(2-(3H-[1,2,3]triazolo[4,5-b]pyridin-3-yl)-4-chlorophenyl)-4-tert-butylbenzenesulfonamide;
4-tert-butyl-N-(4-chloro-2-(2-methyl-1H-benzo[d]imidazol-1-yl)phenyl)benzenesulfonamide;
4-tert-butyl-N-(4-chloro-2-(2-methyl-1H-imidazo[4,5-b]pyridin-1-yl)phenyl)benzenesulfonamide;
4-tert-butyl-N-(4-chloro-2-(1H-imidazo[4,5-c]pyridin-1-yl)phenyl)benzenesulfonamide;
4-tert-butyl-N-(4-chloro-2-(3H-imidazo[4,5-c]pyridin-3-yl)phenyl)benzenesulfonamide;
4-tert-butyl-N-(4-chloro-2-(2-oxo-1H-imidazo[4,5-c]pyridin-3(2H)-yl)phenyl)benzenesulfonamide;
4-tert-butyl-N-(4-chloro-2-(1H-pyrrolo[2,3-b]pyridin-1-yl)phenyl)benzenesulfonamide;
4-tert-butyl-N-(4-chloro-2-(1H-pyrrolo[3,2-c]pyridin-1-yl)phenyl)benzenesulfonamide;
4-tert-butyl-N-(4-chloro-2-(1H-pyrrolo[3,2-b]pyridin-1-yl)phenyl)benzenesulfonamide;
1-(2-(4-tert-butylphenylsulfonamido)-5-chlorophenyl)-N,N-dimethyl-1H-pyrazole-4-carboxamide;
1-(2-(4-tert-butylphenylsulfonamido)-5-chlorophenyl)-1H-pyrazole-4-carboxamide;
N-(2-(1H-[1,2,3]triazolo[4,5-b]pyridin-1-yl)-4-chlorophenyl)-4-isopropoxybenzenesulfonamide;
N-(2-(1H-[1,2,3]triazolo[4,5-b]pyridin-1-yl)-4-chlorophenyl)-4-(4-methyltetrahydro-2H-pyran-4-yl)benzenesulfonamide;
N-(2-(1H-[1,2,3]triazolo[4,5-b]pyridin-1-yl)-4-chlorophenyl)-4-tert-pentylbenzenesulfonamide; and
N-(2-(2-amino-9H-purin-9-yl)-4-chlorophenyl)-4-tert-butylbenzenesulfonamide; or a salt thereof.

In one embodiment, a compound of the present invention is selected from the group consisting of:
N-(2-(6-amino-9H-purin-9-yl)-4-chlorophenyl)-4-tert-butylbenzenesulfonamide;
4-tert-butyl-N-(4-chloro-2-(1H-1,2,3-triazol-1-yl)phenyl)benzenesulfonamide;
ethyl 1-(2-(4-tert-butylphenylsulfonamido)-5-chlorophenyl)-1H-1,2,3-triazole-4-carboxylate;
N-(2-(5-amino-1H-pyrrolo[3,2-b]pyridine-1-yl)-4-chlorophenyl)-4-tert-butylbenzenesulfonamide;
4-tert-butyl-N-(4-chloro-2-(5-methyl-1H-[1,2,3]triazolo[4,5-b]pyridine-1-yl)phenyl)benzenesulfonamide;
N-(2-(1H-[1,2,3]triazolo[4,5-b]pyridin-1-yl)-4-chlorophenyl)-4-isopropylbenzenesulfonamide;
N-(2-(5-amino-1H-[1,2,3]triazolo[4,5-b]pyridine-1-yl)-4-chlorophenyl)-4-tert-butylbenzenesulfonamide;
1-(2-(4-tert-butylphenylsulfonamido)-5-chlorophenyl)-N-methyl-1H-1,2,3-triazole-4-carboxamide;
1-(2-(4-tert-butylphenylsulfonamido)-5-chlorophenyl)-N,N-dimethyl-1H-1,2,3-triazole-4-carboxamide;
N-(2-(4-(azetidine-1-carbonyl)-1H-1,2,3-triazol-1-yl)-4-chlorophenyl)-4-tert-butylbenzenesulfonamide;
4-tert-butyl-N-(4-chloro-2-(4-(4-methylpiperazine-1-carbonyl)-1H-1,2,3-triazol-1-yl)phenyl)benzenesulfonamide;
1-(2-(4-tert-butylphenylsulfonamido)-5-chlorophenyl)-1H-1,2,3-triazole-4-carboxamide;
1-(2-(4-tert-butylphenylsulfonamido)-5-chlorophenyl)-1H-1,2,3-triazole-4-carboxylic acid;
4-tert-butyl-N-(4-chloro-2-(4-(dimethylamino)-1H-pyrazolo[4,3-c]pyridine-1-yl)phenyl)benzenesulfonamide;
N-(2-(4-amino-1H-[1,2,3]triazolo[4,5-c]pyridine-1-yl)-4-chlorophenyl)-4-tert-butylbenzenesulfonamide;
N-(2-(4-amino-1H-pyrazolo[4,3-c]pyridine-1-yl)-4-chlorophenyl)-4-tert-butylbenzenesulfonamide;
4-tert-butyl-N-(4-chloro-2-(4-oxo-4,5-dihydro-1H-pyrazolo[4,3-c]pyridine-1-yl)phenyl)benzenesulfonamide;
4-tert-butyl-N-(4-chloro-2-(4-morpholino-1H-[1,2,3]triazolo[4,5-c]pyridine-1-yl)phenyl)benzenesulfonamide;
4-tert-butyl-N-(4-morpholino-2-(4-morpholino-1H-[1,2,3]triazolo[4,5-c]pyridine-1-yl)phenyl)benzenesulfonamide;
4-tert-butyl-N-(3,4-dichloro-2-(1H-pyrazol-1-yl)phenyl)benzenesulfonamide;
N-(2-(1H-[1,2,3]triazolo[4,5-b]pyridine-1-yl)-4-cyanophenyl)-4-tert-butylbenzenesulfonamide;
4-tert-butyl-N-(4-chloro-2-(5-methyl-4,5,6,7-tetrahydro-1H-[1,2,3]triazolo[4,5-b]pyridine-1-yl)phenyl)benzenesulfonamide;
4-tert-butyl-N-(4-chloro-2-(4,5,6,7-tetrahydro-1H-[1,2,3]triazolo[4,5-b]pyridine-1-yl)phenyl)benzenesulfonamide;
4-tert-butyl-N-(4-chloro-2-(4-(2-methoxyethyl)-4,5,6,7-tetrahydro-1H-[1,2,3]triazolo[4,5-b]pyridine-1-yl)phenyl)benzenesulfonamide;
4-tert-butyl-N-(4-chloro-2-(4-methyl-4,5,6,7-tetrahydro-1H-[1,2,3]triazolo[4,5-b]pyridine-1-yl)phenyl)benzenesulfonamide;
4-tert-butyl-N-(4-chloro-2-(4-ethyl-4,5,6,7-tetrahydro-1H-[1,2,3]triazolo[4,5-b]pyridine-1-yl)phenyl)benzenesulfonamide;
4-tert-butyl-N-(4-chloro-2-(4-isopropyl-4,5,6,7-tetrahydro-1H-[1,2,3]triazolo[4,5-b]pyridine-1-yl)phenyl)benzenesulfonamide;
N-(2-(4-acetyl-4,5,6,7-tetrahydro-1H-[1,2,3]triazolo[4,5-b]pyridine-1-yl)-4-chlorophenyl)-4-tert-butylbenzenesulfonamide;
4-tert-butyl-N-(4-chloro-2-(4-(methylsulfonyl)-4,5,6,7-tetrahydro-1H-[1,2,3]triazolo[4,5-b]pyridine-1-yl)phenyl)benzenesulfonamide;
4-tert-butyl-N-(4-chloro-2-(5-isopropyl-1H-1,2,3-triazol-1-yl)phenyl)benzenesulfonamide;
4-tert-butyl-N-(4-chloro-2-(5-ethyl-1H-1,2,3-triazol-1-yl)phenyl)benzenesulfonamide;
4-tert-butyl-N-(4-chloro-2-(5-(morpholinomethyl)-1H-1,2,3-triazol-1-yl)phenyl)benzenesulfonamide;
4-tert-butyl-N-(4-chloro-2-(4-((dimethylamino)methyl)-1H-1,2,3-triazol-1-yl)phenyl)benzenesulfonamide;
4-tert-butyl-N-(4-chloro-2-(5-(pyrrolidin-1-ylmethyl)-1H-1,2,3-triazol-1-yl)phenyl)benzenesulfonamide;
N-(2-(1H-[1,2,3]triazolo[4,5-b]pyridine-1-yl)-4-chlorophenyl)-3-fluoro-4-morpholinobenzenesulfonamide;
4-tert-butyl-N-(4-chloro-2-(4-(2-hydroxypropan-2-yl)-1H-pyrazol-1-yl)phenyl)benzenesulfonamide;
4-tert-butyl-N-(5-chloro-2-(1H-pyrazolo[4,3-b]pyridine-1-yl)pyridine-3-yl)benzenesulfonamide;
4-tert-butyl-N-(5-chloro-2-(5-methyl-1H-pyrazolo[4,3-b]pyridine-1-yl)pyridine-3-yl)benzenesulfonamide;

4-tert-butyl-N-(5-chloro-2-(1H-imidazo[4,5-b]pyridine-1-yl)pyridine-3-yl)benzenesulfonamide; and
4-tert-butyl-N-(5-chloro-2-(3H-imidazo[4,5-b]pyridine-3-yl)pyridine-3-yl)benzenesulfonamide;
or a salt thereof.

In one embodiment, a compound of the present invention is selected from the group consisting of:
N-(2-(5-amino-1H-pyrrolo[3,2-b]pyridin-1-yl)-5-chloropyridin-3-yl)-4-tert-butylbenzenesulfonamide;
N-(2-(1H-[1,2,3]triazolo[4,5-b]pyridin-1-yl)-5-chloropyridin-3-yl)-4-tert-butylbenzenesulfonamide;
ethyl 1-(3-(4-tert-butylphenylsulfonamido)-5-chloropyridin-2-yl)-1H-pyrazole-4-carboxylate;
N-(2-(1H-[1,2,3]triazolo[4,5-b]pyridin-1-yl)-5-methylpyridin-3-yl)-4-tert-butylbenzenesulfonamide;
4-tert-butyl-N-(5-chloro-2-(4-chloro-1H-pyrazol-1-yl)pyridin-3-yl)benzenesulfonamide;
4-tert-butyl-N-(5-chloro-2-(4-methyl-1H-imidazol-1-yl)pyridin-3-yl)benzenesulfonamide;
4-tert-butyl-N-(5-chloro-2-(4-phenyl-1H-imidazol-1-yl)pyridin-3-yl)benzenesulfonamide;
4-tert-butyl-N-(5-chloro-2-(2-methyl-1H-imidazol-1-yl)pyridin-3-yl)benzenesulfonamide;
4-tert-butyl-N-(5-chloro-2-(2-isopropyl-1H-imidazol-1-yl)pyridin-3-yl)benzenesulfonamide;
4-tert-butyl-N-(5-chloro-2-(2-phenyl-1H-imidazol-1-yl)pyridin-3-yl)benzenesulfonamide;
4-tert-butyl-N-(5-chloro-2-(2-ethyl-1H-imidazol-1-yl)pyridin-3-yl)benzenesulfonamide;
4-tert-butyl-N-(5-chloro-2-(1H-indol-1-yl)pyridin-3-yl)benzenesulfonamide;
N-(2-(1H-benzo[d]imidazol-1-yl)-5-chloropyridin-3-yl)-4-tert-butylbenzenesulfonamide;
4-tert-butyl-N-(5-chloro-2-(1H-indazol-1-yl)pyridin-3-yl)benzenesulfonamide;
N-(2-(1H-benzo[d][1,2,3]triazol-1-yl)-5-chloropyridin-3-yl)-4-tert-butylbenzenesulfonamide;
4-tert-butyl-N-(5-chloro-2-(9H-purin-9-yl)pyridin-3-yl)benzenesulfonamide;
4-tert-butyl-N-(5-chloro-2-(2,4-dimethyl-1H-imidazol-1-yl)pyridin-3-yl)benzenesulfonamide;
4-tert-butyl-N-(5-chloro-2-(2-ethyl-4-methyl-1H-imidazol-1-yl)pyridin-3-yl)benzenesulfonamide;
4-tert-butyl-N-(5-chloro-2-(4-(piperidine-1-carbonyl)-1H-pyrazol-1-yl)pyridin-3-yl)benzenesulfonamide;
4-tert-butyl-N-(5-chloro-2-(4-(morpholine-4-carbonyl)-1H-pyrazol-1-yl)pyridin-3-yl)benzenesulfonamide;
4-tert-butyl-N-(5-chloro-2-(4-(pyrrolidine-1-carbonyl)-1H-pyrazol-1-yl)pyridin-3-yl)benzenesulfonamide;
4-tert-butyl-N-(5-chloro-2-(4-(4-methylpiperazine-1-carbonyl)-1H-pyrazol-1-yl)pyridin-3-yl)benzenesulfonamide;
N-(2-(4-(azetidine-1-carbonyl)-1H-pyrazol-1-yl)-5-chloropyridin-3-yl)-4-tert-butylbenzenesulfonamide;
1-(3-(4-tert-butylphenylsulfonamido)-5-chloropyridin-2-yl)-N-isopropyl-N-methyl-1H-pyrazole-4-carboxamide;
4-tert-butyl-N-(5-chloro-2-(4-(4-isopropylpiperazine-1-carbonyl)-1H-pyrazol-1-yl)pyridin-3-yl)benzenesulfonamide;
4-tert-butyl-N-(5-chloro-2-(4-(3-(dimethylamino)pyrrolidine-1-carbonyl)-1H-pyrazol-1-yl)pyridin-3-yl)benzenesulfonamide;
1-(3-(4-tert-butylphenylsulfonamido)-5-chloropyridin-2-yl)-N-(2-(dimethylamino)ethyl)-N-methyl-1H-pyrazole-4-carboxamide;
4-tert-butyl-N-(5-chloro-2-(4-(1,2,3,6-tetrahydropyridine-1-carbonyl)-1H-pyrazol-1-yl)pyridin-3-yl)benzenesulfonamide;
1-(3-(4-tert-butylphenylsulfonamido)-5-chloropyridin-2-yl)-N-methyl-1H-pyrazole-4-carboxamide;
1-(3-(4-tert-butylphenylsulfonamido)-5-chloropyridin-2-yl)-N,N-dimethyl-1H-pyrazole-4-carboxamide;
1-(3-(4-tert-butylphenylsulfonamido)-5-chloropyridin-2-yl)-N,3-dimethyl-1H-pyrazole-4-carboxamide;
1-(3-(4-tert-butylphenylsulfonamido)-5-chloropyridin-2-yl)-N,N,3-trimethyl-1H-pyrazole-4-carboxamide;
1-(3-(4-tert-butylphenylsulfonamido)-5-chloropyridin-2-yl)-1H-pyrazole-4-carboxylic acid;
N-(2-(4-amino-1H-pyrazol-1-yl)-5-chloropyridin-3-yl)-4-tert-butylbenzenesulfonamide;
N-(1-(3-(4-tert-butylphenylsulfonamido)-5-chloropyridin-2-yl)-1H-pyrazol-4-yl)acetamide;
4-tert-butyl-N-(5-chloro-2-(4-(oxazol-2-yl)-1H-pyrazol-1-yl)pyridin-3-yl)benzenesulfonamide;
4-tert-butyl-N-(4-chloro-2-(1H-indazol-3-yl)phenyl)benzenesulfonamide;
4-tert-butyl-N-(4-chloro-2-(1H-pyrrolo[2,3-b]pyridin-3-yl)phenyl)benzenesulfonamide;
N-(2-(1H-[1,2,3]triazolo[4,5-b]pyridin-1-yl)-4-chlorophenyl)-4-acetylbenzenesulfonamide; and
N-(2-(1H-[1,2,3]triazolo[4,5-b]pyridin-1-yl)-4-chlorophenyl)-4-(1-(hydroxyimino)ethyl)benzenesulfonamide;
or a salt thereof.

In one embodiment, a compound of the present invention is selected from the group consisting of:
N-(2-(1H-[1,2,3]triazolo[4,5-b]pyridin-1-yl)-4-chlorophenyl)-4-(1-(methoxyimino)ethyl)benzenesulfonamide;
N-(2-(1H-[1,2,3]triazolo[4,5-b]pyridin-1-yl)-4-chlorophenyl)-4-(1-aminoethyl)benzenesulfonamide;
N-(2-(1H-[1,2,3]triazolo[4,5-b]pyridin-1-yl)-4-chlorophenyl)-4-(1-(methylamino)ethyl)benzenesulfonamide;
N-(2-(1H-[1,2,3]triazolo[4,5-b]pyridin-1-yl)-4-chlorophenyl)-4-(1-(dimethylamino)ethyl)benzenesulfonamide;
N-(2-(1H-[1,2,3]triazolo[4,5-b]pyridin-1-yl)-4-chlorophenyl)-4-(1-morpholinoethyl)benzenesulfonamide;
N-(4-Chloro-2[1,2,3]triazolo[4,5-b]pyridin-1-yl-phenyl)-4-(1-hydroxy-1-methyl-ethyl)-benzene-sulfonamide;
N-(2-(1H-[1,2,3]triazolo[4,5-b]pyridin-1-yl)-4-chlorophenyl)-4-(1-(ethoxyimino)ethyl)benzenesulfonamide;
N-(2-(1H-[1,2,3]triazolo[4,5-b]pyridin-1-yl)-4-chlorophenyl)-4-(1-(allyloxyimino)ethyl)benzenesulfonamide;
N-(2-(1H-[1,2,3]triazolo[4,5-b]pyridin-1-yl)-4-chlorophenyl)-4-(1-(tert-butoxyimino)ethyl)benzenesulfonamide;
2-(1-(4-(N-(2-(1H-[1,2,3]triazolo[4,5-b]pyridin-1-yl)-4-chlorophenyl)sulfamoyl)phenyl)ethylideneaminooxy)acetic acid;
N-(2-(1H-[1,2,3]triazolo[4,5-b]pyridin-1-yl)-4-chlorophenyl)-4-(1-hydroxy-2-methylpropan-2-yl)benzenesulfonamide;
methyl 2-(4-(N-(2-(1H-[1,2,3]triazolo[4,5-b]pyridin-1-yl)-4-chlorophenyl)sulfamoyl)phenyl)-2-methylpropanoate;
N-(2-(1H-[1,2,3]triazolo[4,5-b]pyridin-1-yl)-4-chlorophenyl)-4-isopropylbenzenesulfonamide;
N-(2-(1H-[1,2,3]triazolo[4,5-b]pyridin-1-yl)-4-chlorophenyl)-4-cyanobenzenesulfonamide;
N-(2-(1H-[1,2,3]triazolo[4,5-b]pyridin-1-yl)-4-chlorophenyl)-4-(1-hydroxyethyl)benzenesulfonamide;
N-(2-(1H-[1,2,3]triazolo[4,5-b]pyridin-1-yl)-4-chlorophenyl)-4-(1,1,1-trifluoro-2-hydroxypropan-2-yl)benzenesulfonamide;
N-(2-(1H-[1,2,3]triazolo[4,5-b]pyridin-1-yl)-4-chlorophenyl)-4-(2-hydroxybutan-2-yl)benzenesulfonamide;
4-tert-butyl-N-(4-chloro-2-(5-methyl-1H-1,2,3-triazol-1-yl)phenyl)benzenesulfonamide;
4-tert-butyl-N-(4-chloro-2-(4-(1-hydroxyethyl)-5-methyl-1H-1,2,3-triazol-1-yl)phenyl)benzenesulfonamide;
N-(2-(1H-[1,2,3]triazolo[4,5-b]pyridin-1-yl)-4-chlorophenyl)-4-iodobenzenesulfonamide;
4-tert-butyl-N-(4-chloro-2-(4-ethynyl-5-methyl-1H-1,2,3-triazol-1-yl)phenyl)benzenesulfonamide;

4-tert-butyl-N-(4-chloro-2-(4-ethyl-5-methyl-1H-1,2,3-triazol-1-yl)phenyl)benzenesulfonamide;
methyl 1-(2-(4-tert-butylphenylsulfonamido)-5-chlorophenyl)-5-methyl-1H-1,2,3-triazole-4-carboxylate;
4-tert-butyl-N-(4-chloro-2-(5-methyl-4-((methylamino)methyl)-1H-1,2,3-triazol-1-yl)phenyl)benzenesulfonamide;
4-tert-butyl-N-(4-chloro-2-(4-((isopropylamino)methyl)-5-methyl-1H-1,2,3-triazol-1-yl)phenyl)benzenesulfonamide;
4-tert-butyl-N-(4-chloro-2-(4-((cyclopropylamino)methyl)-5-methyl-1H-1,2,3-triazol-1-yl)phenyl)benzenesulfonamide;
4-tert-butyl-N-(4-chloro-2-(4-((dimethylamino)methyl)-5-methyl-1H-1,2,3-triazol-1-yl)phenyl)benzenesulfonamide;
4-tert-butyl-N-(4-chloro-2-(5-methyl-4-(morpholinomethyl)-1H-1,2,3-triazol-1-yl)phenyl)benzenesulfonamide;
4-tert-butyl-N-(4-chloro-2-(5-methyl-4-(thiazol-2-yl)-1H-1,2,3-triazol-1-yl)phenyl)benzenesulfonamide;
1-(2-(4-tert-butylphenylsulfonamido)-5-chlorophenyl)-5-methyl-1H-1,2,3-triazole-4-carboxylic acid;
4-tert-butyl-N-(4-chloro-2-(5-methyl-4-(oxazol-2-yl)-1H-1,2,3-triazol-1-yl)phenyl)benzenesulfonamide;
4-tert-butyl-N-(4-chloro-2-(4-(hydroxymethyl)-1H-pyrazol-1-yl)phenyl)benzenesulfonamide;
4-tert-butyl-N-(4-chloro-2-(4-((isopropylamino)methyl)-1H-pyrazol-1-yl)phenyl)benzenesulfonamide;
4-tert-butyl-N-(4-chloro-2-(4-((methylamino)methyl)-1H-pyrazol-1-yl)phenyl)benzenesulfonamide;
4-tert-butyl-N-(4-chloro-2-(4-(morpholinomethyl)-1H-pyrazol-1-yl)phenyl)benzenesulfonamide;
4-tert-butyl-N-(4-chloro-2-(4-((dimethylamino)methyl)-1H-pyrazol-1-yl)phenyl)benzenesulfonamide;
ethyl 1-(2-(4-tert-butylphenylsulfonamido)-5-chlorophenyl)-5-methyl-1H-pyrazole-4-carboxylate;
4-tert-butyl-N-(4-chloro-2-(4-(2-hydroxypropan-2-yl)-5-methyl-1H-pyrazol-1-yl)phenyl)benzenesulfonamide;
N-(4-Chloro-2-[1,2,3]triazolo[4,5-b]pyridin-1-yl-phenyl)-3-fluoro-4-(1-hydroxy-1-methyl-ethyl)-benzenesulfonamide;
N-(2-(1H-[1,2,3]triazolo[4,5-b]pyridin-1-yl)-4-chlorophenyl)-4-(2-hydroxypropan-2-yl)-3-methylbenzenesulfonamide;
N-(2-(1H-[1,2,3]triazolo[4,5-b]pyridin-1-yl)-4-chlorophenyl)-3-chloro-4-(2-hydroxypropan-2-yl)benzenesulfonamide;
N-(2-(1H-[1,2,3]triazolo[4,5-b]pyridin-1-yl)-4-chlorophenyl)-4-(2-hydroxypropan-2-yl)-3-methoxybenzenesulfonamide; and
N-(2-(1H-[1,2,3]triazolo[4,5-b]pyridin-1-yl)-4-chlorophenyl)-4-(2-hydroxypropan-2-yl)-3-(trifluoromethyl)benzenesulfonamide;
or a salt thereof.

In one embodiment, a compound of the present invention is selected from the group consisting of:
4-tert-butyl-N-(4-chloro-2-(4-(2-hydroxypropan-2-yl)-5-methyl-1H-pyrazol-1-yl)phenyl)benzenesulfonamide;
4-tert-butyl-N-(4-chloro-2-(4-ethynyl-5-methyl-1H-1,2,3-triazol-1-yl)phenyl)benzenesulfonamide;
N-(2-(1H-[1,2,3]triazolo[4,5-b]pyridin-1-yl)-4-chlorophenyl)-4-isopropylbenzenesulfonamide;
N-(2-(1H-[1,2,3]triazolo[4,5-b]pyridin-1-yl)-4-chlorophenyl)-4-(1-(hydroxyimino)ethyl)benzenesulfonamide;
4-tert-butyl-N-(4-chloro-2-(5-methyl-4-(thiazol-2-yl)-1H-1,2,3-triazol-1-yl)phenyl)benzenesulfonamide;
4-tert-butyl-N-(4-chloro-2-(4-(1-hydroxyethyl)-5-methyl-1H-1,2,3-triazol-1-yl)phenyl)benzenesulfonamide;
N-(4-Chloro-2[1,2,3]triazolo[4,5-b]pyridin-1-yl-phenyl)-4-(1-hydroxy-1-methyl-ethyl)-benzene-sulfonamide sodium salt
N-(4-Chloro-2[1,2,3]triazolo[4,5-b]pyridin-1-yl-phenyl)-4-(1-hydroxy-1-methyl-ethyl)-benzene-sulfonamide;
N-(4-Chloro-2-[1,2,3]triazolo[4,5-b]pyridin-1-yl-phenyl)-3-fluoro-4-(1-hydroxy-1-methyl-ethyl)-benzenesulfonamide sodium salt; and
N-(4-Chloro-2-[1,2,3]triazolo[4,5-b]pyridin-1-yl-phenyl)-3-fluoro-4-(1-hydroxy-1-methyl-ethyl)-benzenesulfonamide.

In one embodiment, the compounds of the present invention are represented by formula (II), or salts thereof:

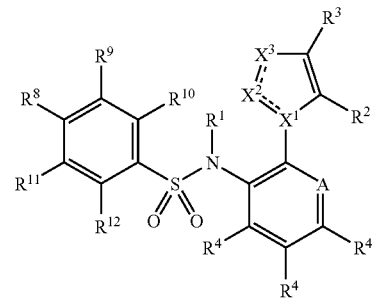

where $R^8$, $R^9$, $R^{10}$, $R^{11}$, and $R^{12}$ are each independently selected from the group consisting of hydrogen, halogen, $C_{1-8}$ alkoxy, $C_{1-8}$ alkyl, —CN, or $C_{1-8}$ haloalkyl, wherein $R^2$, $R^3$, $R^4$, $X^1$, $X^2$, and $X^3$ are as defined above in Formula I.

In one embodiment, the compounds of the present invention are represented by formula (III), or salts thereof:

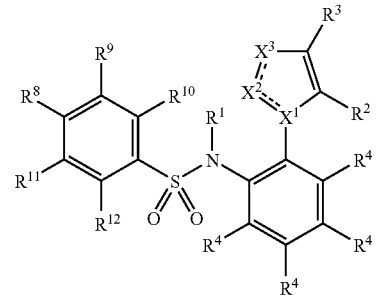

where $R^8$, $R^9$, $R^{10}$, $R^{11}$, and $R^{12}$ are as defined for formula (II).

In one embodiment, the compounds of the present invention are represented by formula (IV), or salts thereof:

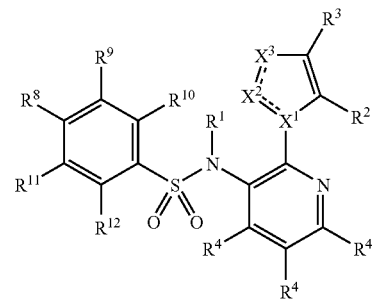

where $R^8$, $R^9$, $R^{10}$, $R^{11}$, and $R^{12}$ are as defined for formula (II).

In one embodiment, the compound is of the formula (V):

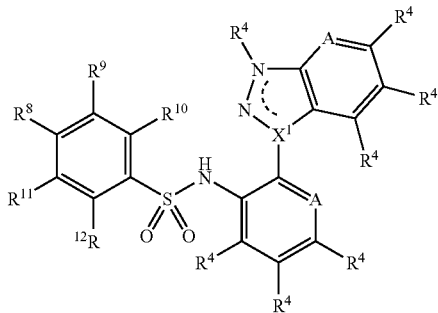

where $R^4$, $R^5$, $R^8$, $R^9$, $R^{10}$, $R^{11}$, $R^{12}$, and $X^1$ and A are as defined in formula (II).

In one embodiment, the compound is of the formula (VI):

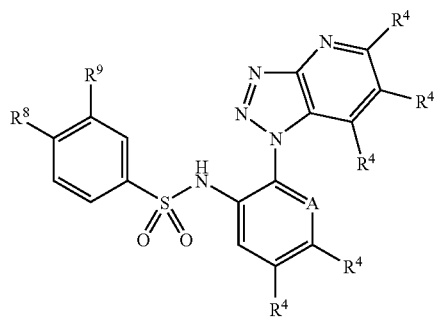

where $R^4$, $R^8$, $R^9$, and A are as defined in formula (II).

In one embodiment, the compound is of the formula (VII):

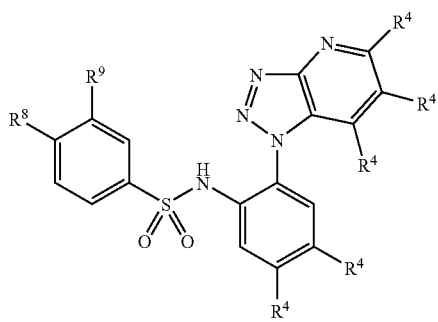

where $R^4$, $R^8$, and $R^9$ are as defined in formula (II).

In one embodiment, the compound is of the formula (VIII):

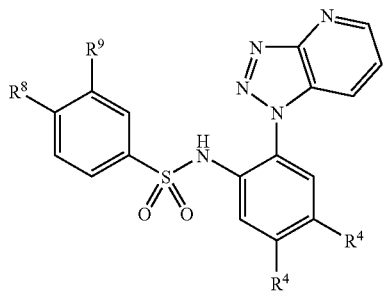

where $R^4$, $R^8$, and $R^9$ are as defined in formula (II).

In another embodiment, the compounds of the present invention are of the formula (CI):

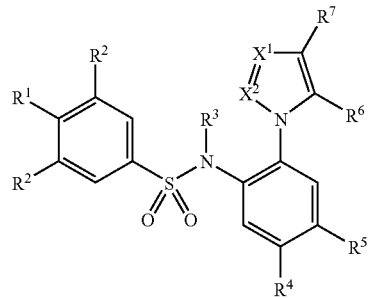

where $R^1$ is halogen, $C_{1-8}$ alkoxy, $C_{1-8}$ alkyl, —CN, or $C_{1-8}$ haloalkyl;

each $R^2$ is independently hydrogen, halogen, $C_{1-8}$ alkyl, —CN, or $C_{1-8}$ haloalkyl;

$R^3$ is hydrogen or $C_{1-8}$ alkyl;

$R^4$ is hydrogen, halogen or $C_{1-8}$ alkyl;

$R^5$ is halogen, —CN or $C_{1-8}$ alkyl;

$R^6$, $R^7$, $R^8$ and $R^9$ are each independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —NO$_2$, —OR', —OC(O)R', —CO$_2$R', —C(O)R', —C(O)NR"R', —OC(O)NR"R', —NR'''C(O)R', —NR'''C(O)NR"R', —NR"R', —NR'''CO$_2$R', —SR', —S(O)R', —S(O)$_2$R', —S(O)$_2$NR"R', —NR"S(O)$_2$R', substituted or unsubstituted $C_{6-10}$ aryl, substituted or unsubstituted 5- to 10-membered heteroaryl and substituted or unsubstituted 3- to 10-membered heterocyclyl; or $R^6$ and $R^7$ together with the atoms which they substitute form a substituted or unsubstituted 5-, 6-, or 7-membered ring;

R', R" and R''' are each independently hydrogen or unsubstituted $C_{1-4}$ alkyl; or R' and R" together with the atoms which they substitute form a substituted or unsubstituted 5-, 6-, or 7-membered ring;

$X^1$ is $CR^8$ or N; and $X^2$ is $CR^9$ or N.

In one embodiment, for the compounds of the present invention of the formula (CI), $R^6$, $R^7$, $R^8$ and $R^9$ are each independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, —NO$_2$, —OR', —OC(O)R', —CO$_2$R', —C(O)R', —C(O)NR"R', —OC(O)NR"R', —NR'''C(O)R', —NR'''C(O)NR"R', —NR"R', —NR'''CO$_2$R', —SR', —S(O)R', —S(O)$_2$R', —S(O)$_2$NR"R', —NR"S(O)$_2$R', substituted or unsubstituted $C_{6-10}$ aryl, substituted or unsubstituted 5- to 10-membered heteroaryl and substituted or unsubstituted 3- to 10-membered heterocyclyl.

In another embodiment, the compounds of the present invention are of the formula (CII):

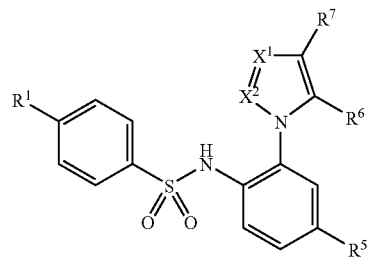

where $R^1$, $R^5$, $R^6$, $R^7$, $X^1$ and $X^2$ are as described in formula (I).

In another embodiment, the compounds of the present invention are of the formula (CIII):

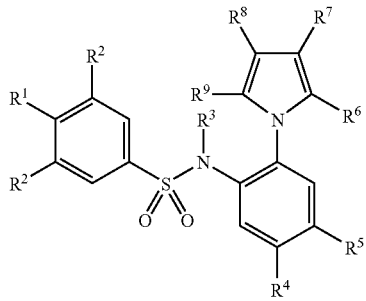

where $R^1$, $R^2$, $R^3$, $R^4$, $R^5$, $R^6$, $R^7$, $R^8$, and $R^9$ are as described in formula (CI).

In another embodiment, the compounds of the present invention are of the formula (CIV):

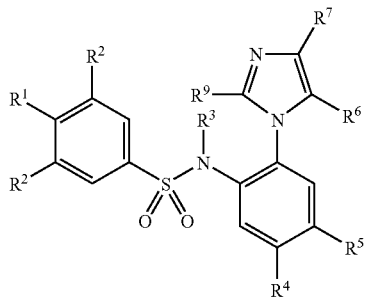

where $R^1$, $R^2$, $R^3$, $R^4$, $R^5$, $R^6$, $R^7$, $R^8$, and $R^9$ are as described in formula (CI).

In another embodiment, the compounds of the present invention are of the formula (CV):

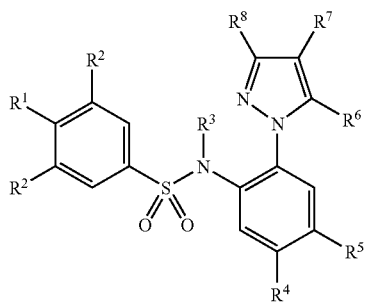

where $R^1$, $R^2$, $R^3$, $R^4$, $R^5$, $R^6$, $R^7$, $R^8$, and $R^9$ are as described in formula (CI).

In another embodiment, the compounds of the present invention are of the formula (CVI):

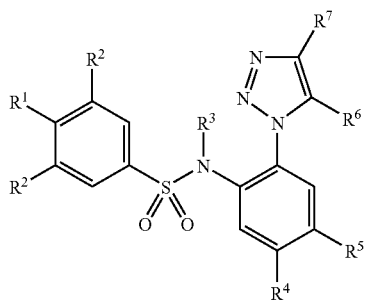

where $R^1$, $R^2$, $R^3$, $R^4$, $R^5$, $R^6$, $R^7$, $R^8$, and $R^9$ are as described in formula (CI).

In another embodiment, the compounds of the present invention are of the of the formula (CVII):

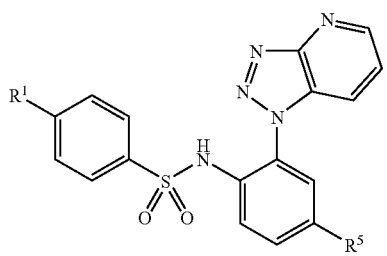

where $R^1$ and $R^5$ are as described in formula (CI).

In another embodiment, the compounds of the present invention are of the formula (CCI):

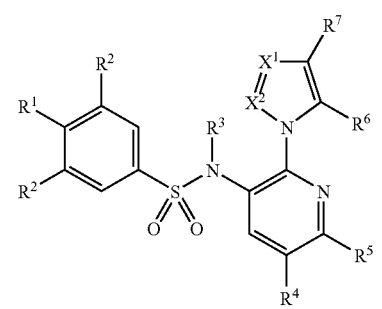

where $R^1$ is halogen, $C_{1-8}$ alkoxy, $C_{1-8}$ alkyl, —CN, or $C_{1-8}$ haloalkyl;

each $R^2$ is independently hydrogen, halogen, $C_{1-8}$ alkyl, —CN, or $C_{1-8}$ haloalkyl;

$R^3$ is hydrogen or $C_{1-8}$ alkyl;

$R^4$ is halogen or $C_{1-8}$ alkyl;

$R^5$ is hydrogen, halogen or $C_{1-8}$ alkyl;

$R^6$, $R^7$, $R^8$ and $R^9$ are each independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —NO$_2$, —OR', —OC(O)R', —CO$_2$R', —C(O)R', —C(O)NR"R', —OC(O)NR"R', —NR'''C(O)R', —NR'''C(O)NR"R', —NR"R', —NR'''CO$_2$R', —SR', —S(O)R', —S(O)$_2$R', —S(O)$_2$NR"R', —NR"S(O)$_2$R', substituted or unsubstituted $C_{6-10}$ aryl, substituted or unsubstituted 5- to 10-membered heteroaryl and substituted or unsubstituted 3- to 10-membered heterocyclyl; or $R^6$ and $R^7$ together with the atoms which they substitute form an substituted or unsubstituted 5-, 6-, or 7-membered ring;

R', R" and R''' are each independently hydrogen or unsubstituted C1-4 alkyl; or R' and R" together with the atoms which they substitute form a substituted or unsubstituted 5-, 6-, or 7-membered ring;

$X^1$ is $CR^8$ or N; and $X^2$ is $CR^9$ or N.

In another embodiment, the compounds of the present invention are of the formula (CCII):

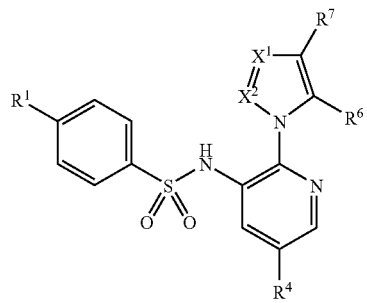

where $R^1$, $R^5$, $R^6$, $R^7$, $X^1$ and $X^2$ are as defined in formula (CCI).

In another embodiment, the compounds of the present invention are of the formula (CCIII):

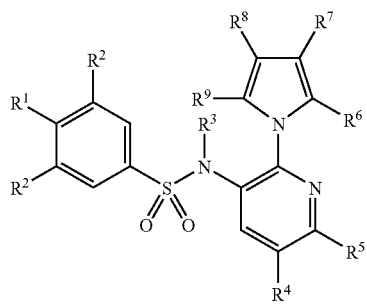

where $R^1$, $R^2$, $R^3$, $R^4$, $R^5$, $R^6$, $R^7$, $R^8$, and $R^9$ are as defined in formula (CCI).

In another embodiment, the compounds of the present invention are of the formula (CCIV):

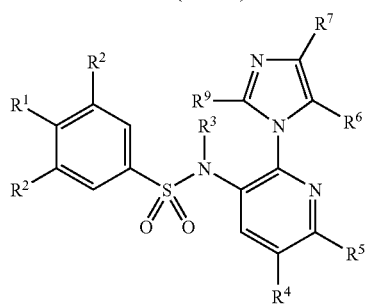

where $R^1$, $R^2$, $R^3$, $R^4$, $R^5$, $R^6$, $R^7$, and $R^9$ are as defined in formula (CCI).

In another embodiment, the compounds of the present invention are of the formula (CCV):

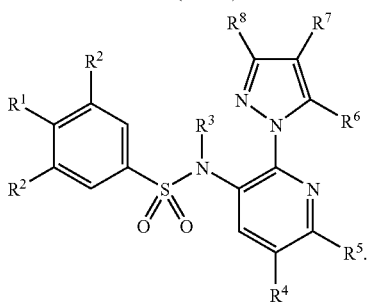

where $R^1$, $R^2$, $R^3$, $R^4$, $R^5$, $R^6$, $R^7$, and $R^8$ are as defined in formula (CCI).

In another embodiment, the compounds of the present invention are of the formula (CCVI):

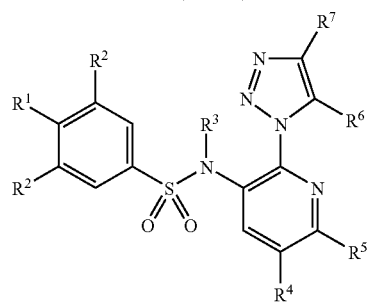

where $R^1$, $R^2$, $R^3$, $R^4$, $R^5$, $R^6$, and $R^7$ are as defined in formula (CCI).

In the following preferred embodiments, the variables are defined when present. For example, for preferred embodiments I-IV, Ar is only in formula (I); whereas $R^8$ is only present in formula (I-IV).

Known Compounds

The compounds shown below:

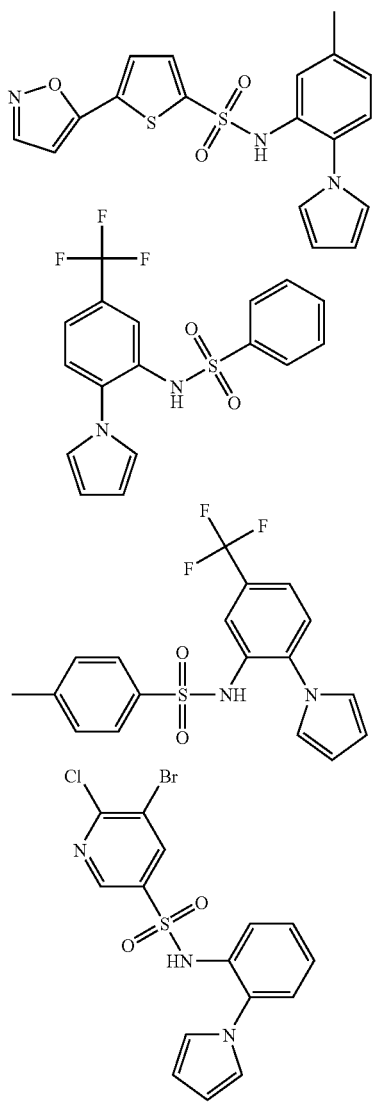

also referred to as:
2-Thiophenesulfonamide, 5-(5-isoxazolyl)-N-[5-methyl-2-(1H-pyrrol-1-yl)phenyl];
Benzenesulfonamide, N-[2-(1H-pyrrol-1-yl)-5-(trifluoromethyl)phenyl];
Benzenesulfonamide, 4-methyl-N-[2-(1H-pyrrol-1-yl)-5-(trifluoromethyl)phenyl];
3-Pyridinesulfonamide, 5-bromo-6-chloro-N-[2-(1H-pyrrol-1-yl)phenyl];
Benzenesulfonamide, 4-fluoro-N-[2-(1H-pyrrol-1-yl)phenyl]; and
2-Thiophenesulfonamide, 5-(3-isoxazolyl)-N-[5-methyl-2-(1H-pyrrol-1-yl)phenyl],
are known, but not as CCR9 or CCR2 antagonists.

Preferred Embodiments I-IV

In one embodiment, Ar is a $C_{6-10}$ aryl.
In one embodiment, Ar is phenyl.
In one embodiment, Ar is a $C_{5-10}$ heteroaryl.
In one embodiment, Ar is a $C_5$ heteroaryl, preferably with one heteroatom which is N, O or S.
In one embodiment, Ar is a $C_{6-10}$ aryl with at least 1 substituents other than hydrogen; preferably halogen or alkyl.
In one embodiment, Ar is a $C_{6-10}$ aryl with at least 2 substituents other than hydrogen; preferably where at least one is halogen or alkyl.
In one embodiment, Ar is a substituted or unsubstituted bicyclic aryl or substituted or unsubstituted bicyclic heteroaryl.
In one embodiment, A is $CR^4$.
In one embodiment, A is N.
In one embodiment, $R^8$ is $C_{1-8}$ alkyl or halogen.
In one embodiment, $R^8$ is substituted $C_{1-8}$ alkyl.
In one embodiment, $R^8$ is substituted $C_{1-8}$ alkyl, wherein $R^8$ is substituted with —OH.
In one embodiment, $R^8$ is —C(CH$_3$)$_2$OH.
In one embodiment, $R^9$ is $C_{1-8}$ alkyl or halogen.
In one embodiment, $R^9$ is fluorine.
In one embodiment, $X^1$ is N, $X^2$ is $CR^6$ and $X^3$ is $CR^7$.
In one embodiment, $X^1$ is C, $X^2$ is N and $X^3$ is $CR^7$.
In one embodiment, $X^1$ is C, $X^2$ is $CR^6$ and $X^3$ is N.
In one embodiment, $X^1$ is N, $X^2$ is N and $X^3$ is $CR^7$.
In one embodiment, $X^1$ is N, $X^2$ is $CR^6$ and $X^3$ is N.
In one embodiment, $X^1$ is C, $X^2$ is N and $X^3$ is N.
In one embodiment, $X^1$ is N, $X^2$ is N and $X^3$ is N.
In one embodiment, $R^2$ and $R^3$, together with the atoms which they substitute form a 5- or 6-membered ring.
In one embodiment, $R^2$ and $R^3$, together with the atoms which they substitute form phenyl.
In one embodiment, $R^2$ and $R^3$, together with the atoms which they substitute form a pyridine.
In one embodiment, $R^2$ and $R^3$, together with the atoms which they substitute form a pyrimidine.
In one embodiment, $R^2$ and $R^3$, together with the atoms which they substitute form a pyrazine.
In one embodiment, the $R^4$ para to the sulfonamide bond is halogen.
In one embodiment, the $R^4$ meta to the sulfonamide bond and para to the 5-membered ring is halogen.

Preferred Embodiments V-VIII

In one embodiment, the $R^4$ para to the sulfonamide bond is halogen.
In one embodiment, the $R^4$ meta to the sulfonamide bond and para to the 5-membered ring is halogen.
In one embodiment, $R^8$ is substituted $C_{1-8}$ alkyl.
In one embodiment, $R^8$ is substituted $C_{1-8}$ alkyl, wherein $R^8$ is substituted with —OH.
In one embodiment, $R^8$ is —C(CH$_3$)$_2$OH.
In one embodiment, $R^9$ is fluorine.

Preferred Substituents for Formula CI-CVII

In one embodiment, $R^1$ is unsubstituted or substituted $C_{1-8}$ alkyl.
In one embodiment, $R^1$ is substituted $C_{1-8}$ alkyl, wherein $R^8$ is substituted with —OH.
In one embodiment, $R^1$ is —C(CH$_3$)$_3$
In one embodiment, $R^1$ is substituted $C_{1-8}$ alkyl.
In one embodiment, $R^1$ is —C(CH$_3$)$_2$OH.
In one embodiment, each $R^2$ is hydrogen.
In one embodiment, at least one $R^2$ is fluorine.
In one embodiment, $R^3$ is hydrogen.
In one embodiment, $R^4$ is hydrogen.
In one embodiment, $R^5$ is halogen, more preferably chlorine.
In one embodiment, $R^6$ is hydrogen, halogen, substituted or unsubstituted $C_{1-8}$ alkyl, —CO$_2$R', —C(O)R', —C(O)NR'R", oxo (=O or —O$^-$), and —OR', where R' and R" are defined above in the definitions section under suitable substituents for substituted alkyl. When $R^6$ is substituted alkyl, preferred substituents include halogen, and —OR.
In one embodiment, $R^7$ is hydrogen, halogen, substituted or unsubstituted $C_{1-8}$ alkyl.
In one embodiment, $R^6$ and $R^7$ together form a substituted or unsubstituted $C_6$ aryl.
In one embodiment, $R^6$ and $R^7$ together form a substituted or unsubstituted $C_6$ heteroaryl.
In one embodiment, $R^6$ and $R^7$ together form a substituted or unsubstituted pyridine.
In one embodiment, $R^9$ is hydrogen or substituted or unsubstituted $C_{1-8}$ alkyl.

Preferred Embodiments of Formula CCI-CCVI

In one embodiment, $R^1$ is $C_{1-8}$ alkyl.
In one embodiment, $R^1$ is unsubstituted or substituted $C_{1-8}$ alkyl.
In one embodiment, $R^1$ is substituted $C_{1-8}$ alkyl, wherein $R^8$ is substituted with —OH.

In one embodiment, $R^1$ is $C(CH_3)_3$
In one embodiment, $R^1$ is substituted $C_{1-8}$ alkyl.
In one embodiment, $R^1$ is —$C(CH_3)_2OH$.
In one embodiment, each $R^2$ is hydrogen.
In one embodiment, $R^3$ is hydrogen.
In one embodiment, $R^4$ is halogen, preferably chlorine.
In one embodiment, $R^5$ is hydrogen.
In one embodiment, $R^6$ and $R^7$ together form a substituted or unsubstituted $C_6$ aryl.
In one embodiment, $R^6$ and $R^7$ together form a substituted or unsubstituted $C_6$ heteroaryl.
In one embodiment, $R^6$ and $R^7$ together form a substituted or unsubstituted pyridine.

Compositions that Modulate Chemokine Activity

In another aspect, the present invention provides compositions that modulate chemokine activity, specifically CCR9 activity. Generally, the compositions for modulating chemokine receptor activity in humans and animals will comprise a pharmaceutically acceptable excipient or diluent and a compound having any of the formulae (I-VIII).

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative. and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

In one embodiment, the present invention provides a composition consisting of a pharmaceutically acceptable carrier and a compound of the invention.

Methods of Treatment

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present invention also contemplates administration of the compounds and compositions of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In still other embodiments, the present methods are directed to the treatment of allergic diseases, wherein a compound or composition of the invention is administered either alone or in combination with a second therapeutic agent, wherein said second therapeutic agent is an antihistamine. When used in combination, the practitioner can administer a combination of the compound or composition of the present invention and a second therapeutic agent. Also, the compound or composition and the second therapeutic agent can be administered sequentially, in any order.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

In treating, preventing, ameliorating, controlling or reducing the risk of inflammation, the compounds of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, biological TNF sequestrants, fentanyl, ibuprofen, indomethacin, ketorolac, morphine, naproxen, phenacetin, piroxicam, a steroidal analgesic, sufentanyl, sunlindac, tenidap, and the like.

Similarly, the compounds of the present invention may be administered with a pain reliever; a potentiator such as caffeine, an H2-antagonist, simethicone, aluminum or magnesium hydroxide; a decongestant such as pseudophedrine; an antitussive such as codeine; a diuretic; a sedating or non-sedating antihistamine; a very late antigen (VLA-4) antagonist; an immunosuppressant such as cyclosporin, tacrolimus, rapamycin, EDG receptor agonists, or other FK-506 type immunosuppressants; a steroid; a non-steroidal anti-asthmatic agent such as a β2-agonist, leukotriene antagonist, or leukotriene biosynthesis inhibitor; an inhibitor of phosphodiesterase type IV (PDE-IV); a cholesterol lowering agent such as a HMG-CoA reductase inhibitor, sequestrant, or cholesterol absorption inhibitor; and an anti-diabetic agent such as insulin, α-glucosidase inhibitors or glitazones.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating or Preventing CCR9-mediated Conditions or Diseases

In yet another aspect, the present invention provides methods of treating or preventing a CCR9-mediated condition or disease by administering to a subject having such a condition or disease a therapeutically effective amount of any compound of formulae above. Compounds for use in the present methods include those compounds according to the above formulae, those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR9-mediated condition or disease" and related phrases and terms refer to a condition or disease characterized by inappropriate, i.e., less than or greater than normal, CCR9 functional activity. Inappropriate CCR9 functional activity might arise as the result of CCR9 expression in cells which normally do not express CCR9, increased CCR9 expression (leading to, e.g., inflammatory and immunoregulatory disorders and diseases) or decreased CCR9 expression. Inappropriate CCR9 functional activity might also arise as the result of TECK secretion by cells which normally do not secrete TECK, increased TECK expression (leading to, e.g., inflammatory and immunoregulatory disorders and diseases) or decreased TECK expression. A CCR9-mediated condition or disease may be completely or partially mediated by inappropriate CCR9 functional activity. However, a CCR9-mediated condition or disease is one in which modulation of CCR9 results in some effect on the underlying condition or disease (e.g., a CCR9 antagonist results in some improvement in patient well being in at least some patients).

The term "therapeutically effective amount" means the amount of the subject compound that will elicit the biological or medical response of a cell, tissue, system, or animal, such as a human, that is being sought by the researcher, veterinarian, medical doctor or other treatment provider.

Diseases and conditions associated with inflammation, immune disorders, infection and cancer can be treated or prevented with the present compounds, compositions, and methods. In one group of embodiments, diseases or conditions, including chronic diseases, of humans or other species can be treated with inhibitors of CCR9 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, microscopic colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) immune mediated food allergies such as Coeliac (Celiac) disease (14) pulmonary fibrosis and other fibrotic diseases, (15) irritable bowel syndrome, (16) primary sclerosing cholangitis and (17) cancer (including both primary and metastatic).

In another group of embodiments, diseases or conditions can be treated with modulators and agonists of CCR9 function. Examples of diseases to be treated by modulating CCR9 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is means to include bone marrow transplant conditions and solid organ (e.g., kidney, liver, lung, heart, pancreas or combination thereof) transplant conditions.

Preferably, the present methods are directed to the treatment of diseases or conditions selected from inflammatory bowel disease including Crohn's disease and Ulcerative Colitis, allergic diseases, psoriasis, atopic dermatitis and asthma, autoimmune disease such as rheumatoid arthritis and immune-mediated food allergies such as Coelaic disease.

In yet other embodiments, the present methods are directed to the treatment of psoriasis where a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

Preparation of Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in the examples. Specifically, generic procedures for sulfonamide formation, pyridine N-oxide formation and 2-aminophenyl-arylmethanone synthesis via Friedel-Crafts type approaches are given, but numerous other standard chemistries are described within and were employed routinely.

While not intended to be exhaustive, representative synthetic organic transformations which can be used to prepare compounds of the invention are included below.

These representative transformations include; standard functional group manipulations; reductions such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckwald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nucleophilic substitution reactions; alkylations; acylations; sulfonamide formation; chlorosulfonylations; ester and related hydrolyses, and the like.

Certain molecules claimed in this patent can exist in different enantiomeric and diastereomeric forms and all such variants of these compounds are within the scope of the invention.

In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention, including those listed in the table of activities, can be made by the methods and approaches described in the following experimental section, and by the use of standard organic chemistry transformations that are well known to those skilled in the art.

EXAMPLES

Exemplary compounds used in the method of the invention and in pharmaceutical compositions of the invention include but are not limited to the compounds listed in the following table. Pharmaceutically acceptable salts of the compounds listed in this table are also useful in the method of the invention and in pharmaceutical compositions of the invention. These compounds are within the scope of this invention and were tested for CCR9 activity as described below.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (br, broad; s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

Examples

Exemplary compounds used in the method of the invention and in pharmaceutical compositions of the invention include but are not limited to the compounds listed in Table 1. Pharmaceutically acceptable salts of the compounds listed in Table 1 are also useful in the method of the invention and in pharmaceutical compositions of the invention.

The compounds shown in Table 1 can be synthesized using the method shown in the chart and detailed below.

Compounds of the invention were assayed for activity in the chemotaxis assay described herein under the section below titled "Example of in vitro assay" where the "chemotaxis assay" is described. All compounds listed in Table 1 has IC$_{50}$ of <1000 nM in the chemotaxis assay.

TABLE 1

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 1. | 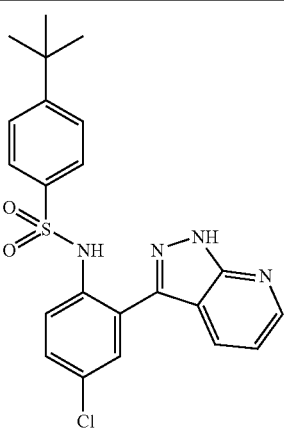 | T | 441.0 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 2. | 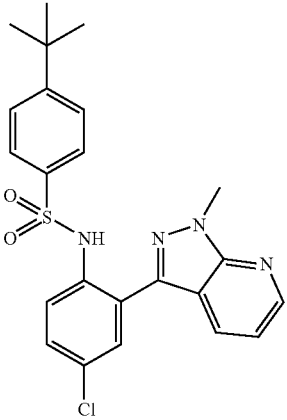 | T | 455.0 |
| 3. | 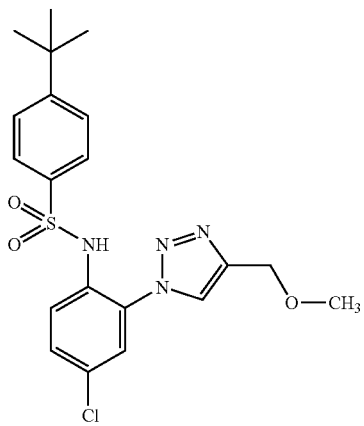 | D | 435.0 |
| 4. | 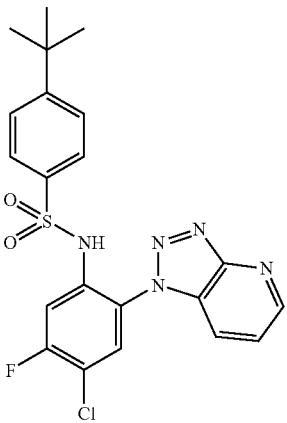 | D | 460.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 5. | 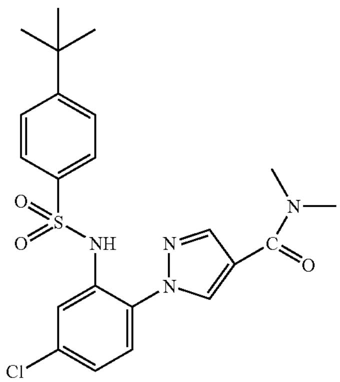 | D | 460.0 |
| 6. | 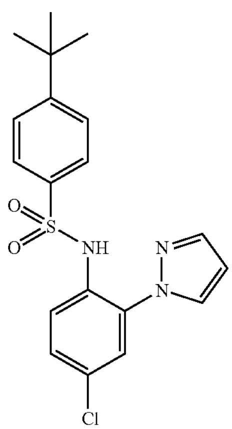 | D | 390.0 |
| 7. | 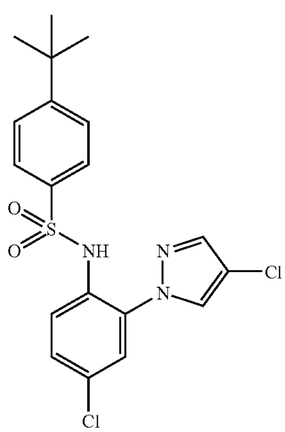 | D | 424.0 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 8. | (structure) | D | 433.1 |
| 9. | (structure) | D | 462.1 |
| 10. | (structure) | D | 432.1 |

TABLE 1-continued
Exemplary compounds with CCR9 activity in one of the
chemotaxis, binding or calcium mobilization assays,
with IC50 < 1000 nM
| | STRUCTURE | Synthetic Method | Observed Molecular Ion (M + 1) |
|---|---|---|---|
| 11. | 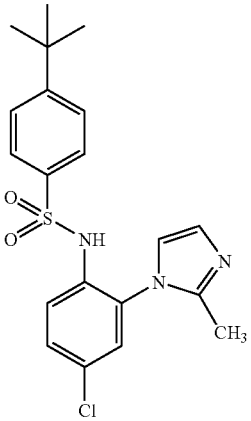 | D | 404.0 |
| 12. | 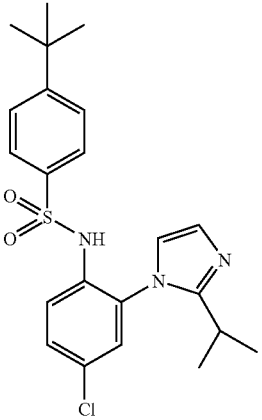 | D | 432.1 |
| 13. | 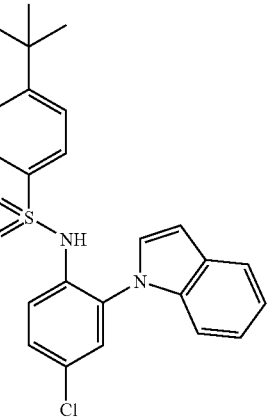 | D | 439.0 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 14. | 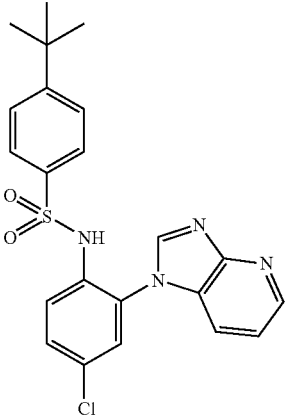 | D | 440.0 |
| 15. | 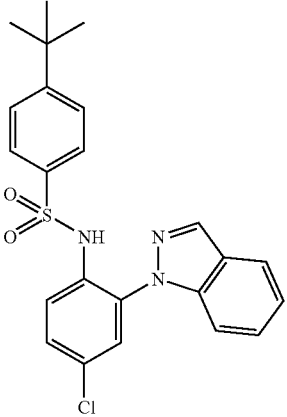 | D | 440.0 |
| 16. | 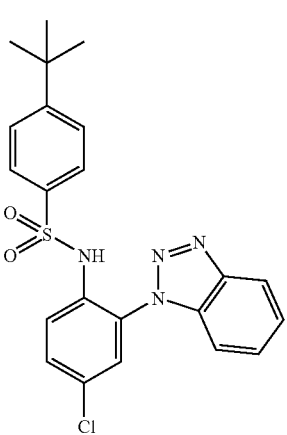 | D | 441.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 17. | *4-tert-butylphenyl sulfonamide linked to 4-chloro-2-(9H-purin-9-yl)phenyl* | D | 442.0 |
| 18. | *4-tert-butylphenyl sulfonamide linked to 4-chloro-2-(7H-purin-7-yl)phenyl* | D | 442.0 |
| 19. | *4-tert-butylphenyl sulfonamide linked to 4-chloro-2-(2-ethyl-1H-imidazol-1-yl)phenyl* | D | 418.0 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 20. | 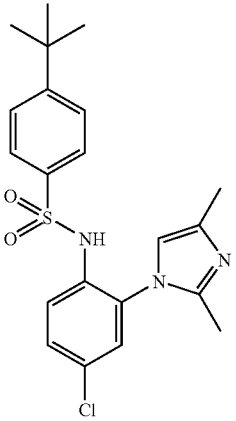 | D | 418.0 |
| 21. | 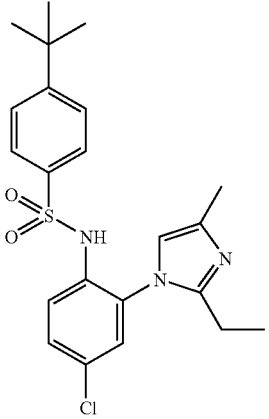 | D | 432.1 |
| 22. | 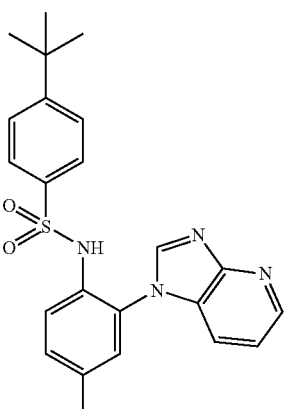 | D | 441.0 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 23. | | D | 441.0 |
| 24. | | D | 457.0 |
| 25. | | D | 442.0 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 26. | 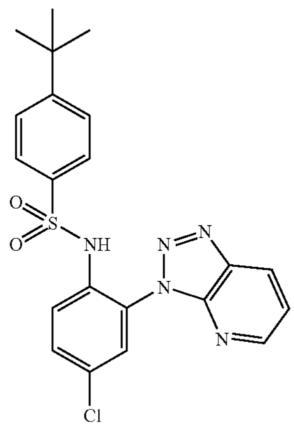 | D | 442.0 |
| 27. | 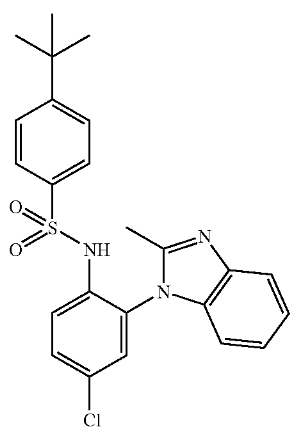 | D | 454.0 |
| 28. | 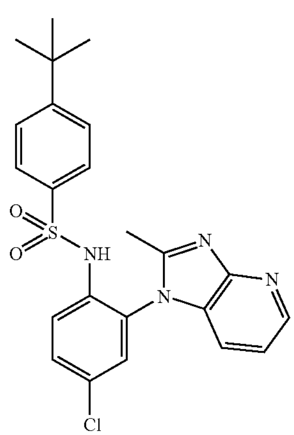 | D | 455.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 29. | 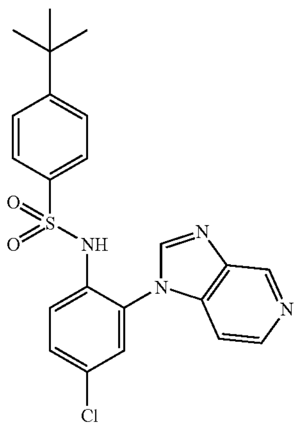 | D | 441.0 |
| 30. | 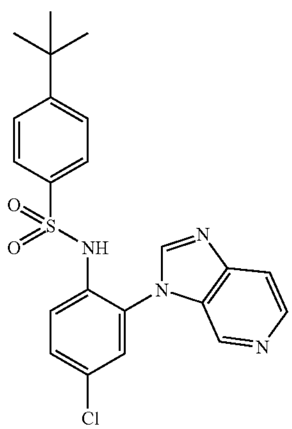 | D | 441.0 |
| 31. | 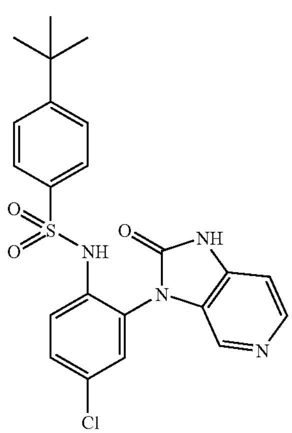 | D | 457.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 32. | 4-tert-butyl-N-[4-chloro-2-(1H-pyrrolo[2,3-b]pyridin-1-yl)phenyl]benzenesulfonamide | D | 440.0 |
| 33. | 4-tert-butyl-N-[4-chloro-2-(1H-pyrrolo[3,2-c]pyridin-1-yl)phenyl]benzenesulfonamide | D | 440.0 |
| 34. | 4-tert-butyl-N-[4-chloro-2-(1H-pyrrolo[3,2-b]pyridin-1-yl)phenyl]benzenesulfonamide | D | 440.0 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 35. | 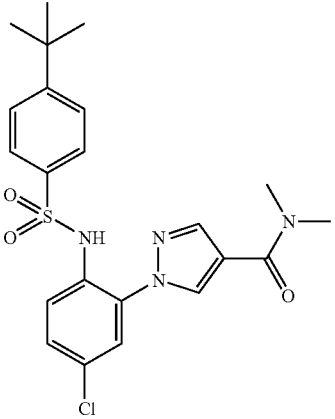 | E | 435.0 |
| 36. | 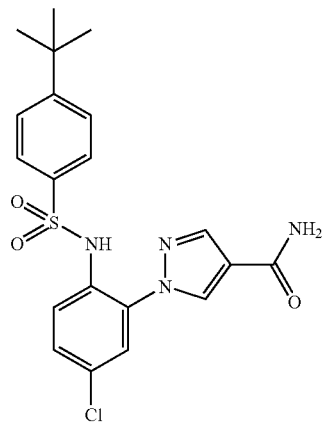 | E | 461.1 |
| 37. | 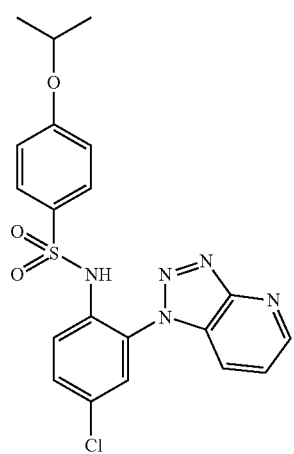 | G | 444.0 |

TABLE 1-continued

Exemplary compounds with CCR9 activity in one of the chemotaxis, binding or calcium mobilization assays, with IC50 < 1000 nM

| STRUCTURE | Synthetic Method | Observed Molecular Ion (M + 1) |
|---|---|---|
| 38. | G | 484.0 |
| 39. | G | 456.1 |
| 40. | G | 457.0 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 41. | | G | 457.1 |
| 42. | | G | 391.0 |
| 43. | | G | 463.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 44. | (structure) | G | 455.0 |
| 45. | (structure) | G | 456.4 |
| 46. | (structure) | G | 352.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 47. | | G | 457.0 |
| 48. | | H | 448.0 |
| 49. | | H | 462.0 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 50. | 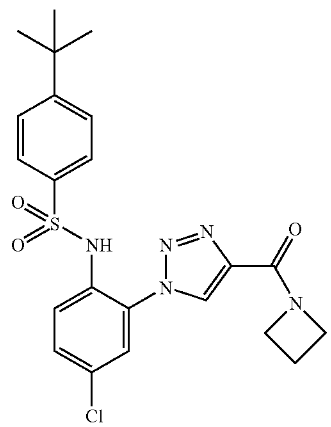 | H | 474.0 |
| 51. | 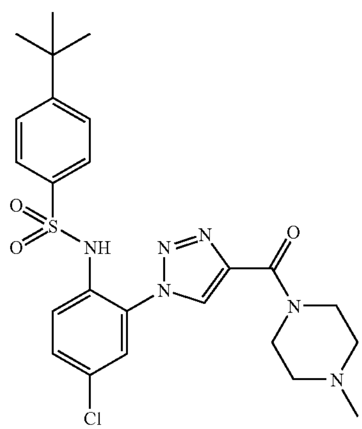 | H | 517.1 |
| 52. | 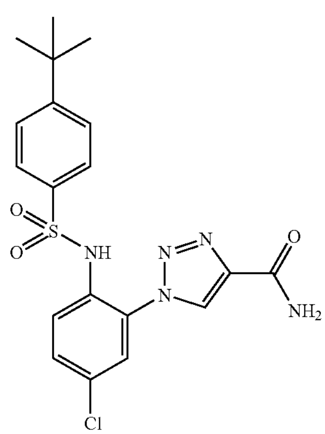 | H | 434.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 53. | 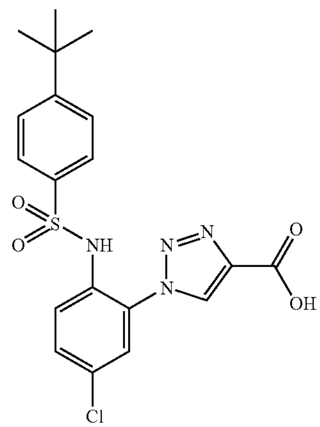 | I | 435.0 |
| 54. | 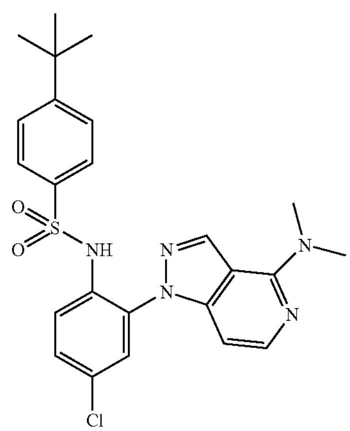 | J | 484.0 |
| 55. | 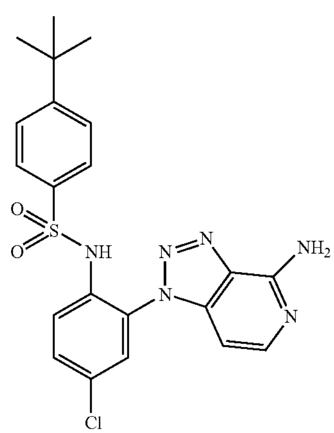 | J | 457.0 |

TABLE 1-continued
Exemplary compounds with CCR9 activity in one of the
chemotaxis, binding or calcium mobilization assays,
with IC50 < 1000 nM
| | STRUCTURE | Synthetic Method | Observed Molecular Ion (M + 1) |
|---|---|---|---|
| 56. | 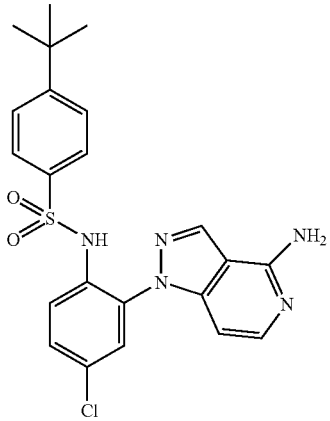 | J | 456.0 |
| 57. | 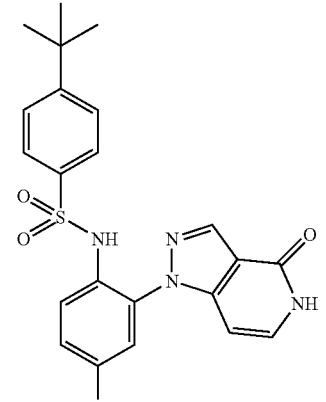 | J | 457.0 |
| 58. | 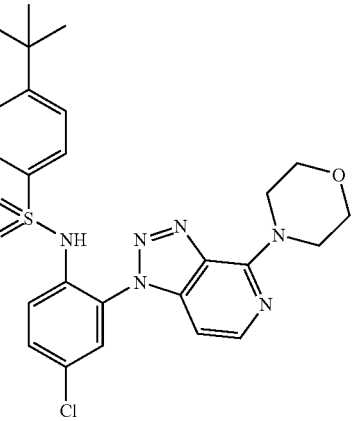 | J | 527.5 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 59. | | J | 578.6 |
| 60. | | L | 424.1 |
| 61. | | L | 433.1 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 62. | 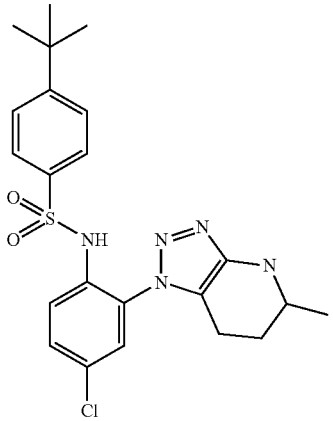 | M | 460.4 |
| 63. | 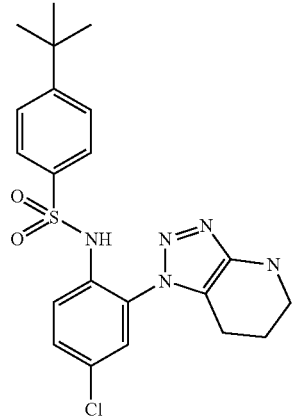 | M | 446.1 |
| 64. | 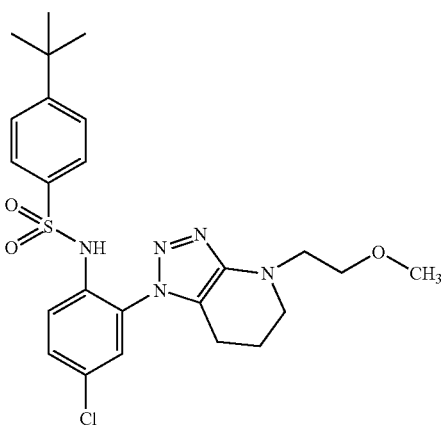 | N | 504.4 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 65. | 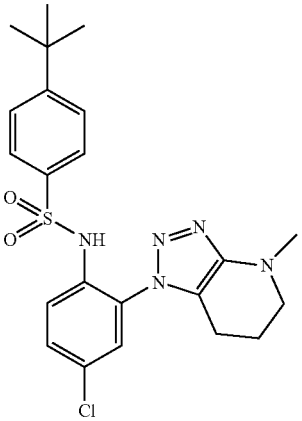 | N | 460.1 |
| 66. | 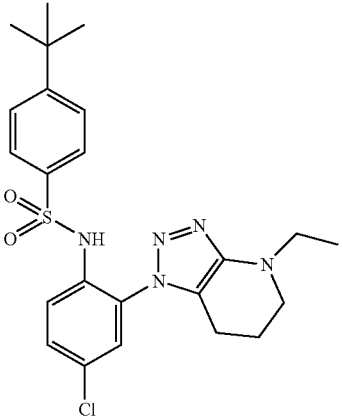 | N | 474.1 |
| 67. | 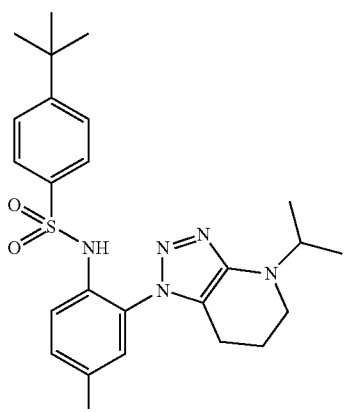 | N | 488.1 |

TABLE 1-continued
Exemplary compounds with CCR9 activity in one of the
chemotaxis, binding or calcium mobilization assays,
with IC50 < 1000 nM
| STRUCTURE | Synthetic Method | Observed Molecular Ion (M + 1) |
|---|---|---|
| 68. 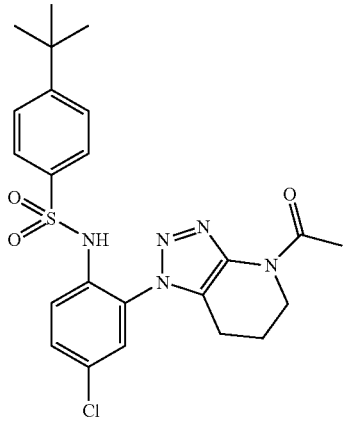 | O | 488.4 |
| 69. 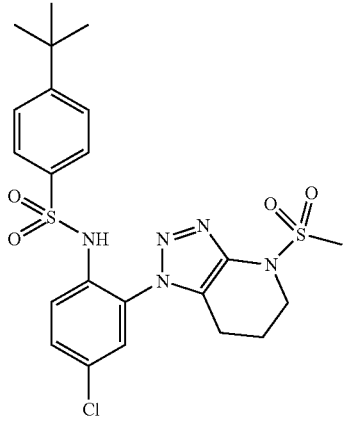 | O | 524.0 |
| 70. 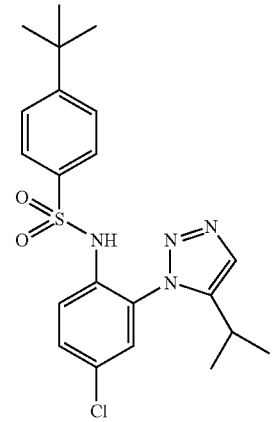 | Q | 433.1 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 71. | | Q | 419.3 |
| 72. | | Q | 490.4 |
| 73. | | Q | 448.4 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 74. | 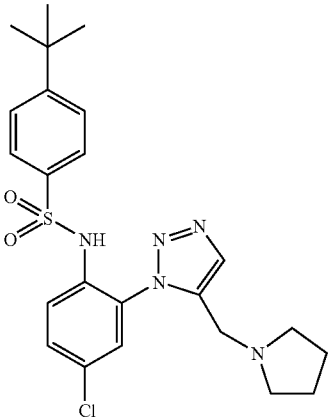 | Q | 474.4 |
| 75. | 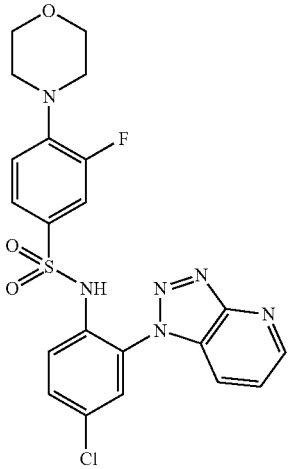 | R | 489.0 |
| 76. | 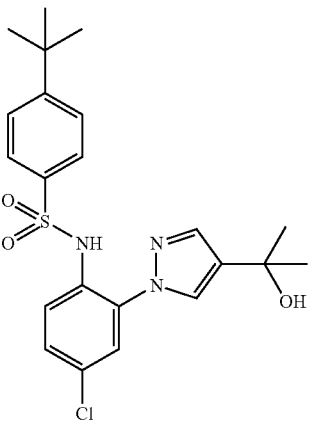 | S | 448.1 |

TABLE 1-continued
Exemplary compounds with CCR9 activity in one of the
chemotaxis, binding or calcium mobilization assays,
with IC50 < 1000 nM
| STRUCTURE | Synthetic Method | Observed Molecular Ion (M + 1) |
|---|---|---|
| 77. 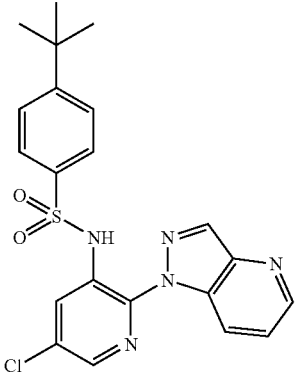 | D | 442.0 |
| 78. 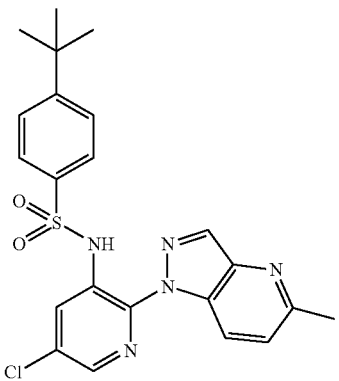 | D | 456.0 |
| 79. 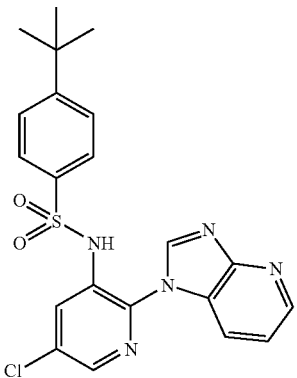 | D | 442.1 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 80. | 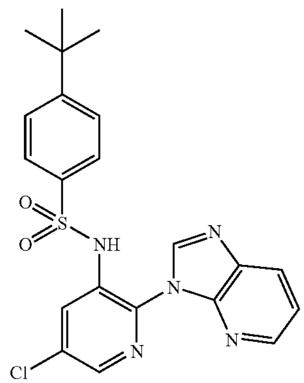 | D | 442.1 |
| 81. | 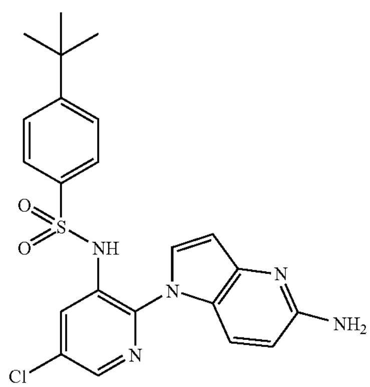 | D | 456.0 |
| 82. | 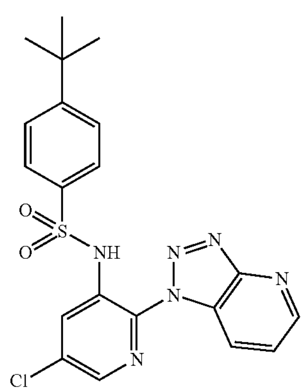 | D | 443.0 |

TABLE 1-continued
Exemplary compounds with CCR9 activity in one of the
chemotaxis, binding or calcium mobilization assays,
with IC50 < 1000 nM
| | STRUCTURE | Synthetic Method | Observed Molecular Ion (M + 1) |
|---|---|---|---|
| 83. | 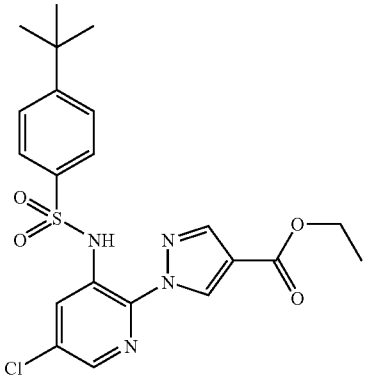 | D | 463.0 |
| 84. | 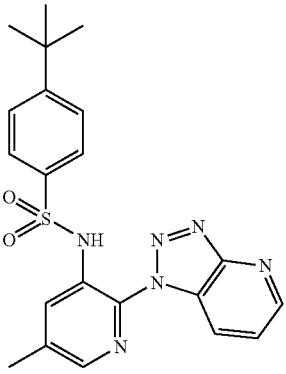 | D | 423.1 |
| 85. | 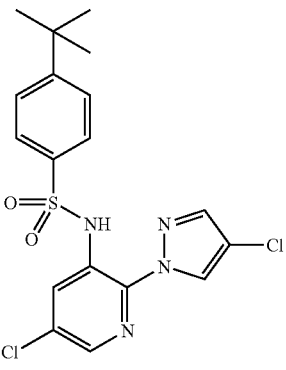 | D | 425.0 |

TABLE 1-continued

Exemplary compounds with CCR9 activity in one of the chemotaxis, binding or calcium mobilization assays, with IC50 < 1000 nM

| STRUCTURE | Synthetic Method | Observed Molecular Ion (M + 1) |
|---|---|---|
| 86. (4-tert-butylphenylsulfonamide-5-chloro-2-(4-methylimidazol-1-yl)pyridine) | D | 405.0 |
| 87. (4-tert-butylphenylsulfonamide-5-chloro-2-(4-phenylimidazol-1-yl)pyridine) | D | 467.0 |
| 88. (4-tert-butylphenylsulfonamide-5-chloro-2-(2-methylimidazol-1-yl)pyridine) | D | 405.0 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 89. | | D | 433.1 |
| 90. | | D | 467.0 |
| 91. | | D | 419.0 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 92. | 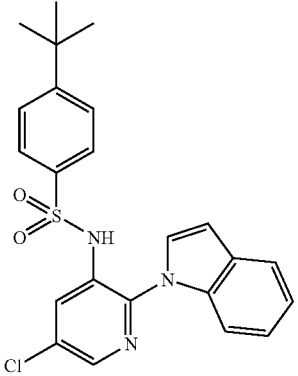 | D | 440.0 |
| 93. | 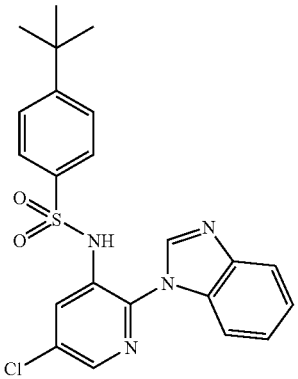 | D | 441.0 |
| 94. | 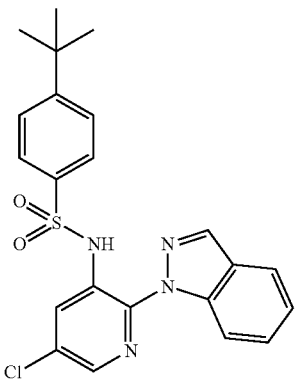 | D | 441.0 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 95. | 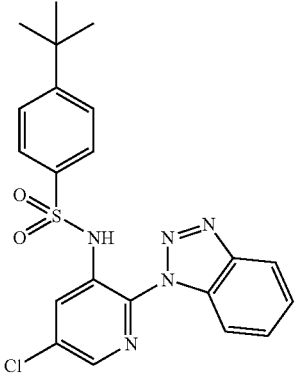 | D | 442.0 |
| 96. | 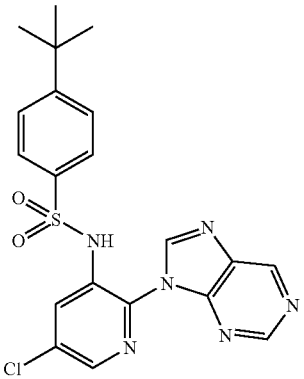 | D | 443.0 |
| 97. | 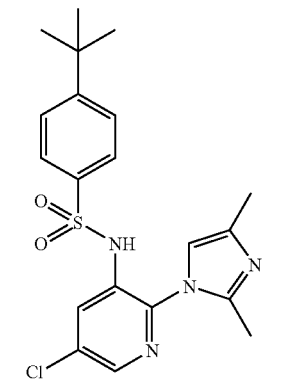 | D | 419.0 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 98. | (structure) | D | 433.1 |
| 99. | (structure) | E | 502.1 |
| 100. | (structure) | E | 504.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 101. | | E | 488.0 |
| 102. | | E | 517.1 |
| 103. | | E | 474.0 |

TABLE 1-continued

Exemplary compounds with CCR9 activity in one of the chemotaxis, binding or calcium mobilization assays, with IC50 < 1000 nM

| STRUCTURE | Synthetic Method | Observed Molecular Ion (M + 1) |
|---|---|---|
| 104. | E | 490.1 |
| 105. | E | 545.1 |
| 106. | E | 531.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 107. | | E | 519.1 |
| 108. | | E | 500.0 |
| 109. | | E | 448.0 |

TABLE 1-continued

Exemplary compounds with CCR9 activity in one of the
chemotaxis, binding or calcium mobilization assays,
with IC50 < 1000 nM

| STRUCTURE | Synthetic Method | Observed Molecular Ion (M + 1) |
|---|---|---|
| 110. | E | 462.0 |
| 111. | E | 462.0 |
| 112. | E | 476.0 |

TABLE 1-continued
Exemplary compounds with CCR9 activity in one of the
chemotaxis, binding or calcium mobilization assays,
with IC50 < 1000 nM
| | STRUCTURE | Synthetic Method | Observed Molecular Ion (M + 1) |
|---|---|---|---|
| 113. | 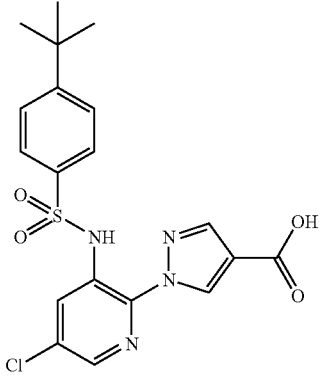 | F | 435.0 |
| 114. | 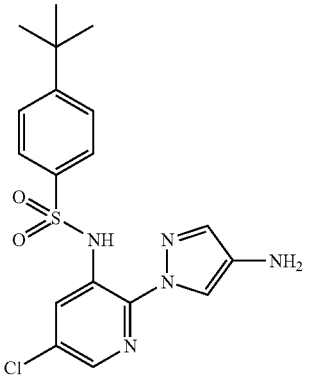 | G | 406.0 |
| 115. | 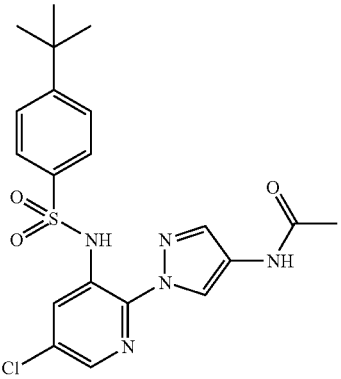 | H | 448.0 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 116. | 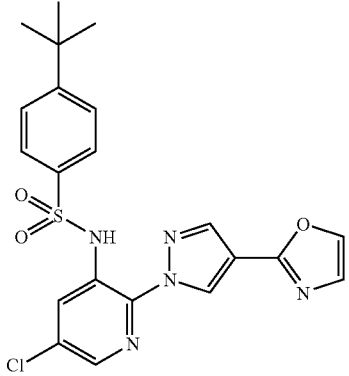 | I | 458.0 |
| 117. | 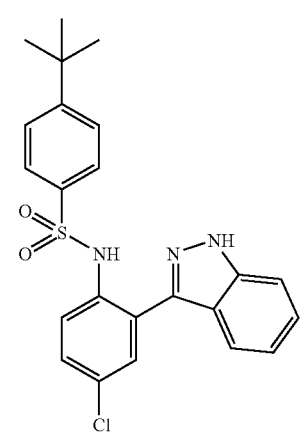 | V | 441.1 |
| 118. | 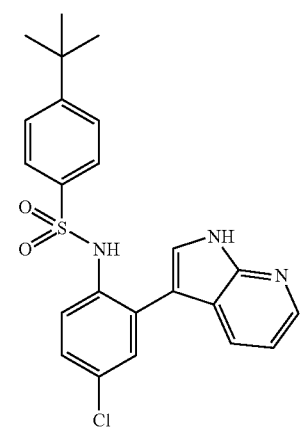 | V | 440.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 119. | 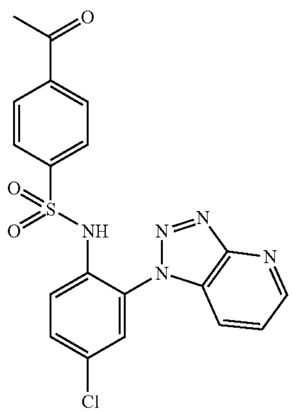 | G | 428.0 |
| 120. | 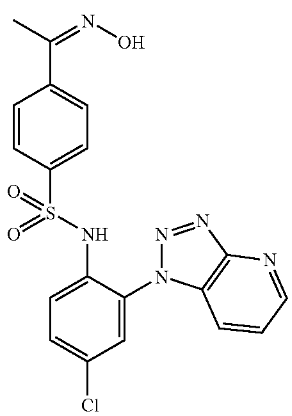 | W | 443.0 |
| 121. | 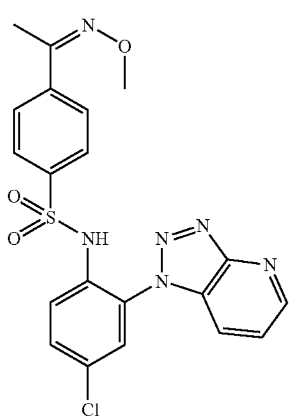 | W | 457.0 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 122. | 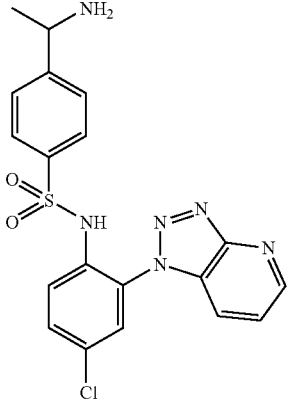 | X | 428.0 |
| 123. | 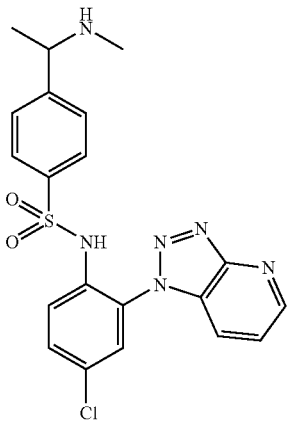 | X | 443.1 |
| 124. | 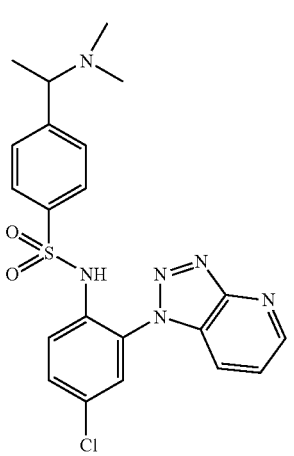 | X | 457.1 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 125. | 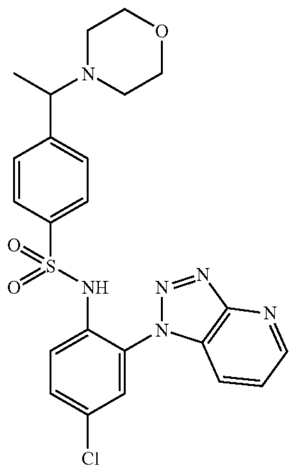 | X | 499.1 |
| 126. | 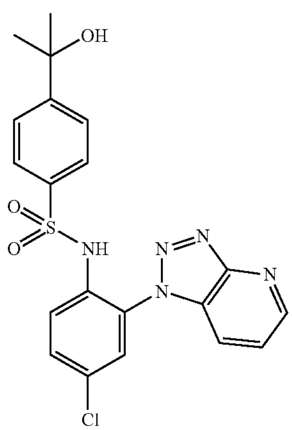 | Y | 466.0 (M + Na) |
| 127. | 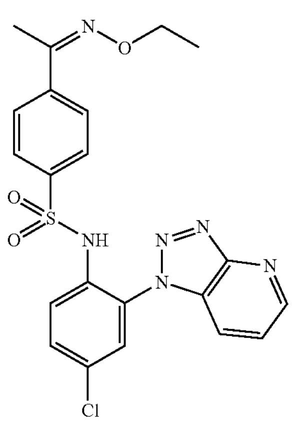 | W | 471.1 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 128. | 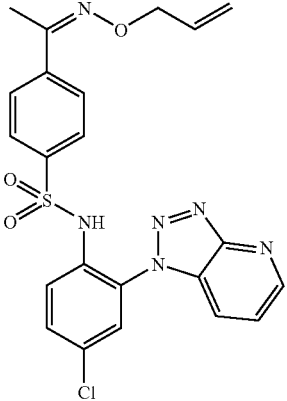 | W | 483.1 |
| 129. | 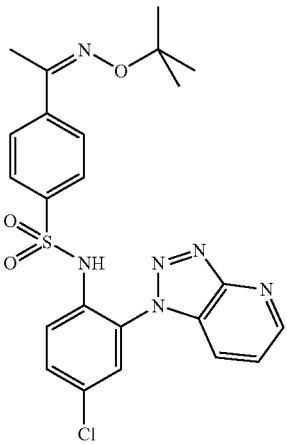 | W | 499.1 |
| 130. | 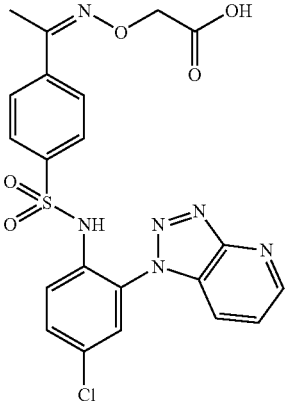 | W | 501.1 |

TABLE 1-continued
Exemplary compounds with CCR9 activity in one of the chemotaxis, binding or calcium mobilization assays, with IC50 < 1000 nM
| | STRUCTURE | Synthetic Method | Observed Molecular Ion (M + 1) |
|---|---|---|---|
| 131. | 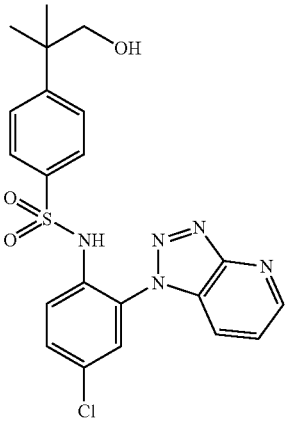 | Z | 458.0 |
| 132. | 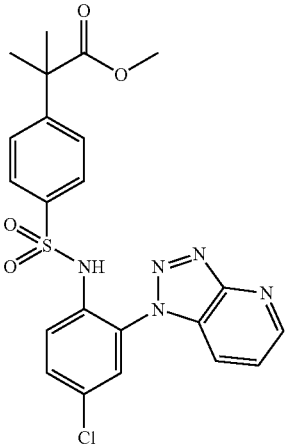 | G | 486.4 |
| 133. | 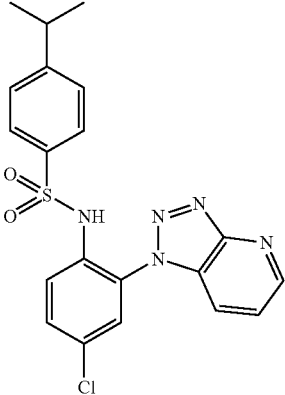 | G | 428.0 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 134. | | G | 411.0 |
| 135. | | AA | 430.1 |
| 136. | | BB | 498.0 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 137. | 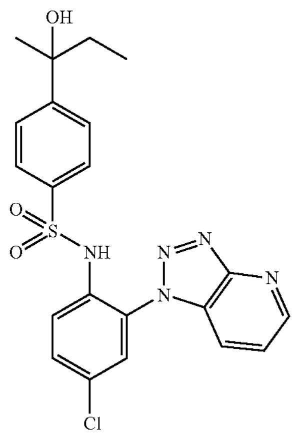 | Y | 440.0 |
| 138. | 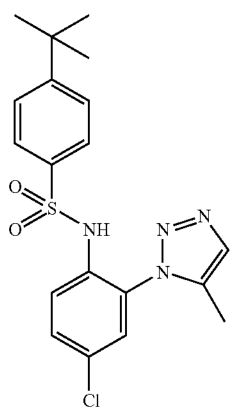 | CC | 405.4 |
| 139. | 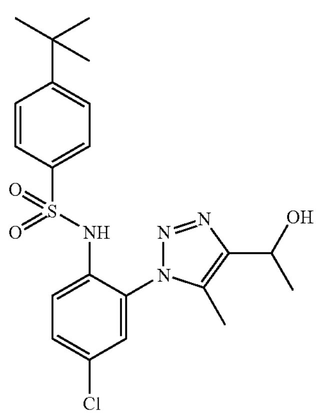 | DD | 449.1 |

TABLE 1-continued
Exemplary compounds with CCR9 activity in one of the chemotaxis, binding or calcium mobilization assays, with IC50 < 1000 nM
| STRUCTURE | Synthetic Method | Observed Molecular Ion (M + 1) |
|---|---|---|
| 140. 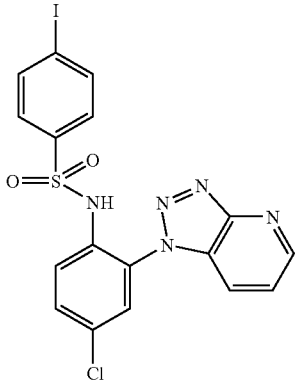 | G | 512.0 |
| 141. 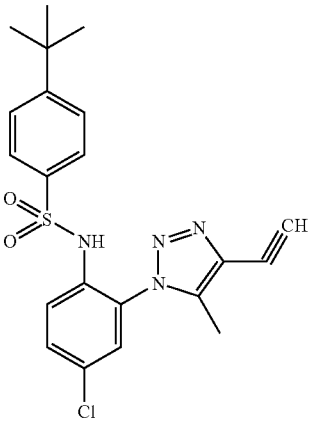 | EE | 429.3 |
| 142. 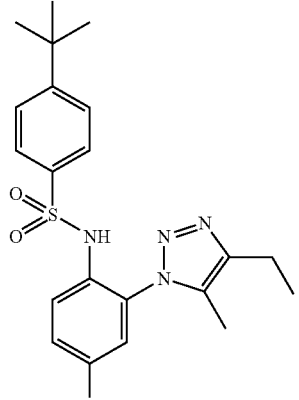 | FF | 433.4 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 143. | 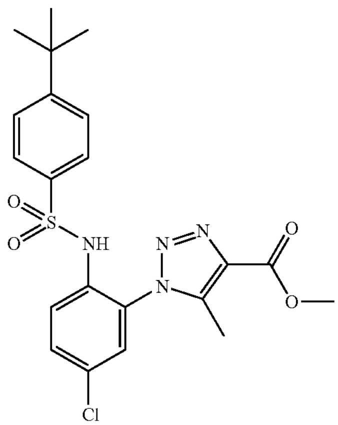 | GG | 463.4 |
| 144. | 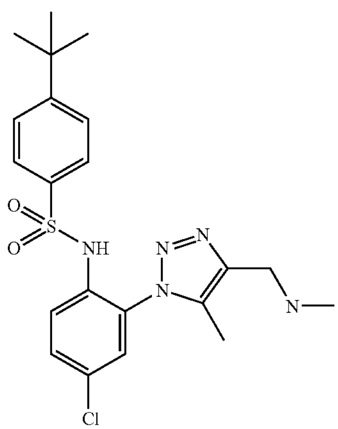 | HH | 448.4 |
| 145. | 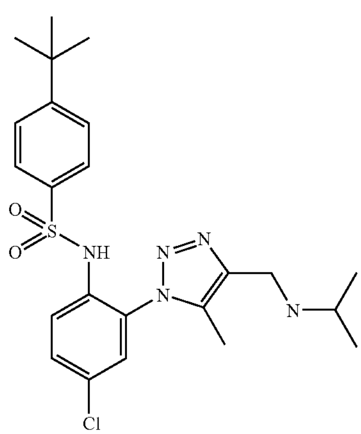 | HH | 476.5 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 146. | | HH | 474.4 |
| 147. | | HH | 462.4 |
| 148. | | HH | 504.5 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 149. | [4-tert-butylphenyl-SO2-NH-(4-chloro-2-yl)phenyl-N-triazole(5-methyl)-thiazole] | II | 488.1 |
| 150. | [4-tert-butylphenyl-SO2-NH-(4-chloro-2-yl)phenyl-N-triazole(5-methyl)-COOH] | JJ | 449.3 |
| 151. | [4-tert-butylphenyl-SO2-NH-(4-chloro-2-yl)phenyl-N-triazole(5-methyl)-oxazole] | KK | 472.0 |

TABLE 1-continued
Exemplary compounds with CCR9 activity in one of the chemotaxis, binding or calcium mobilization assays, with IC50 < 1000 nM
| STRUCTURE | Synthetic Method | Observed Molecular Ion (M + 1) |
|---|---|---|
| 152. 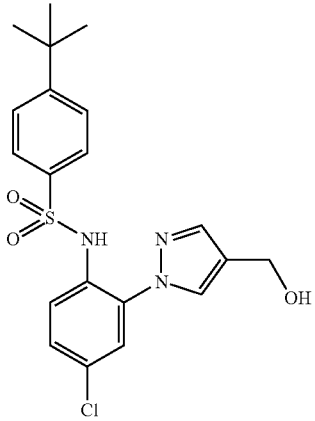 | LL | 420.1 |
| 153. 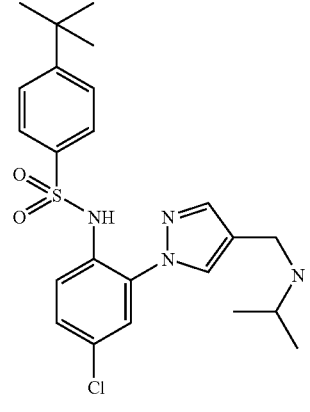 | MM | 461.4 |
| 154. 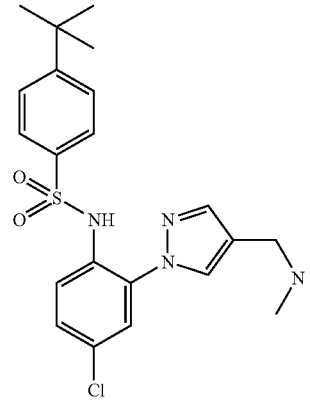 | MM | 433.4 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 155. | 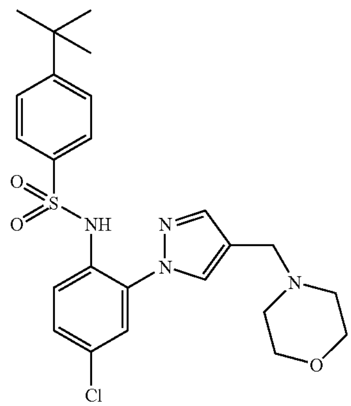 | MM | 489.4 |
| 156. | 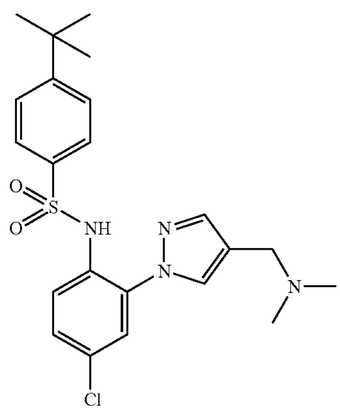 | MM | 447.4 |
| 157. | 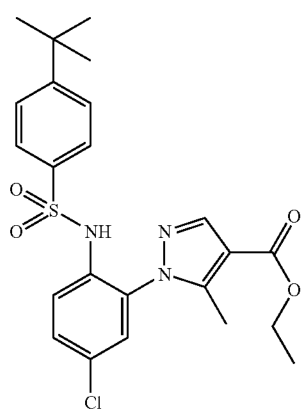 | NN | 476.5 |

TABLE 1-continued

Exemplary compounds with CCR9 activity in one of the chemotaxis, binding or calcium mobilization assays, with IC50 < 1000 nM

| | STRUCTURE | Synthetic Method | Observed Molecular Ion (M + 1) |
|---|---|---|---|
| 158. | 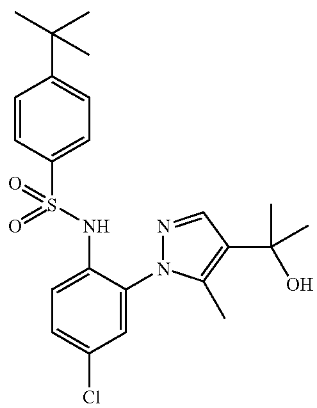 | S | 462.4 |
| 159. | 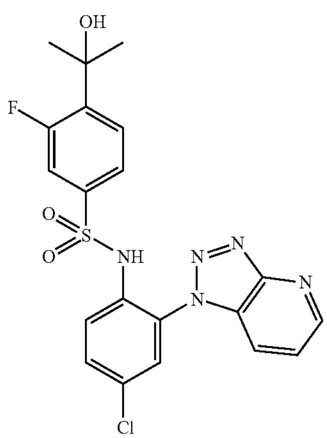 | PP | 484.0 (M + Na) |
| 160. | 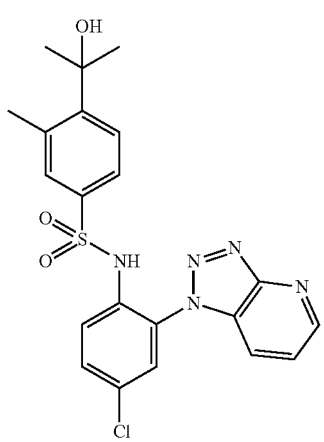 | PP | 480.1 |

TABLE 1-continued

Exemplary compounds with CCR9 activity in one of the
chemotaxis, binding or calcium mobilization assays,
with IC50 < 1000 nM

| | STRUCTURE | Synthetic Method | Observed Molecular Ion (M + 1) |
|---|---|---|---|
| 161. | (structure) | PP | 500.0 (M + Na) |
| 162. | (structure) | PP | 496.0 (M + Na) |
| 163. | (structure) | PP | 512.0 |

The names for the structures 1-163 are provided in the following table:

| Structure | Name |
|---|---|
| 1 | 4-tert-butyl-N-(4-chloro-2-(1H-pyrazolo[3,4-b]pyridin-3-yl)phenyl)benzenesulfonamide |
| 2 | 4-tert-butyl-N-(4-chloro-2-(1-methyl-1H-pyrazolo[3,4-b]pyridin-3-yl)phenyl)benzenesulfonamide |
| 3 | 4-tert-butyl-N-(4-chloro-2-(4-(methoxymethyl)-1H-1,2,3-triazol-1-yl)phenyl)benzenesulfonamide |
| 4 | N-(2-(1H-[1,2,3]triazolo[4,5-b]pyridin-1-yl)-4-chloro-5-fluorophenyl)-4-tert-butylbenzenesulfonamide |
| 5 | 1-(2-(4-tert-butylphenylsulfonamido)-4-chlorophenyl)-N,N-dimethyl-1H-pyrazole-4-carboxamide |
| 6 | 4-tert-butyl-N-(4-chloro-2-(1H-pyrazol-1-yl)phenyl)benzenesulfonamide |
| 7 | 4-tert-butyl-N-(4-chloro-2-(4-chloro-1H-pyrazol-1-yl)phenyl)benzenesulfonamide |
| 8 | 4-tert-butyl-N-(4-chloro-2-(4-isopropyl-1H-1,2,3-triazol-1-yl)phenyl)benzenesulfonamide |
| 9 | ethyl 1-(2-(4-tert-butylphenylsulfonamido)-5-chlorophenyl)-1H-pyrazole-4-carboxylate |
| 10 | 4-tert-butyl-N-(4-chloro-2-(4-isopropyl-1H-pyrazol-1-yl)phenyl)benzenesulfonamide |
| 11 | 4-tert-butyl-N-(4-chloro-2-(2-methyl-1H-imidazol-1-yl)phenyl)benzenesulfonamide |
| 12 | 4-tert-butyl-N-(4-chloro-2-(2-isopropyl-1H-imidazol-1-yl)phenyl)benzenesulfonamide |
| 13 | 4-tert-butyl-N-(4-chloro-2-(1H-indol-1-yl)phenyl)benzenesulfonamide |
| 14 | 4-tert-butyl-N-(4-chloro-2-(1H-imidazo[4,5-b]pyridin-1-yl)phenyl)benzenesulfonamide |
| 15 | 4-tert-butyl-N-(4-chloro-2-(1H-indazol-1-yl)phenyl)benzenesulfonamide |
| 16 | N-(2-(1H-benzo[d][1,2,3]triazol-1-yl)-4-chlorophenyl)-4-tert-butylbenzenesulfonamide |
| 17 | 4-tert-butyl-N-(4-chloro-2-(9H-purin-9-yl)phenyl)benzenesulfonamide |
| 18 | 4-tert-butyl-N-(4-chloro-2-(7H-purin-7-yl)phenyl)benzenesulfonamide |
| 19 | 4-tert-butyl-N-(4-chloro-2-(2-ethyl-1H-imidazol-1-yl)phenyl)benzenesulfonamide |
| 20 | 4-tert-butyl-N-(4-chloro-2-(2,4-dimethyl-1H-imidazol-1-yl)phenyl)benzenesulfonamide |
| 21 | 4-tert-butyl-N-(4-chloro-2-(2-ethyl-4-methyl-1H-imidazol-1-yl)phenyl)benzenesulfonamide |
| 22 | 4-tert-butyl-N-(4-chloro-2-(1H-imidazo[4,5-b]pyridin-1-yl)phenyl)benzenesulfonamide |
| 23 | 4-tert-butyl-N-(4-chloro-2-(3H-imidazo[4,5-b]pyridin-3-yl)phenyl)benzenesulfonamide |
| 24 | N-(2-(2-amino-7H-purin-7-yl)-4-chlorophenyl)-4-tert-butylbenzenesulfonamide |
| 25 | N-(2-(1H-[1,2,3]triazolo[4,5-b]pyridin-1-yl)-4-chlorophenyl)-4-tert-butylbenzenesulfonamide |
| 26 | N-(2-(3H-[1,2,3]triazolo[4,5-b]pyridin-3-yl)-4-chlorophenyl)-4-tert-butylbenzenesulfonamide |
| 27 | 4-tert-butyl-N-(4-chloro-2-(2-methyl-1H-benzo[d]imidazol-1-yl)phenyl)benzenesulfonamide |
| 28 | 4-tert-butyl-N-(4-chloro-2-(2-methyl-1H-imidazo[4,5-b]pyridin-1-yl)phenyl)benzenesulfonamide |
| 29 | 4-tert-butyl-N-(4-chloro-2-(1H-imidazo[4,5-c]pyridin-1-yl)phenyl)benzenesulfonamide |
| 30 | 4-tert-butyl-N-(4-chloro-2-(3H-imidazo[4,5-c]pyridin-3-yl)phenyl)benzenesulfonamide |
| 31 | 4-tert-butyl-N-(4-chloro-2-(2-oxo-1H-imidazo[4,5-c]pyridin-3(2H)-yl)phenyl)benzenesulfonamide |
| 32 | 4-tert-butyl-N-(4-chloro-2-(1H-pyrrolo[2,3-b]pyridin-1-yl)phenyl)benzenesulfonamide |
| 33 | 4-tert-butyl-N-(4-chloro-2-(1H-pyrrolo[3,2-c]pyridin-1-yl)phenyl)benzenesulfonamide |
| 34 | 4-tert-butyl-N-(4-chloro-2-(1H-pyrrolo[3,2-b]pyridin-1-yl)phenyl)benzenesulfonamide |
| 35 | 1-(2-(4-tert-butylphenylsulfonamido)-5-chlorophenyl)-N,N-dimethyl-1H-pyrazole-4-carboxamide |
| 36 | 1-(2-(4-tert-butylphenylsulfonamido)-5-chlorophenyl)-1H-pyrazole-4-carboxamide |
| 37 | N-(2-(1H-[1,2,3]triazolo[4,5-b]pyridin-1-yl)-4-chlorophenyl)-4-isopropoxybenzenesulfonamide |
| 38 | N-(2-(1H-[1,2,3]triazolo[4,5-b]pyridin-1-yl)-4-chlorophenyl)-4-(4-methyltetrahydro-2H-pyran-4-yl)benzenesulfonamide |
| 39 | N-(2-(1H-[1,2,3]triazolo[4,5-b]pyridin-1-yl)-4-chlorophenyl)-4-tert-pentylbenzenesulfonamide |
| 40 | N-(2-(2-amino-9H-purin-9-yl)-4-chlorophenyl)-4-tert-butylbenzenesulfonamide |

-continued

| Structure | Name |
|---|---|
| 41 | N-(2-(6-amino-9H-purin-9-yl)-4-chlorophenyl)-4-tert-butylbenzenesulfonamide |
| 42 | 4-tert-butyl-N-(4-chloro-2-(1H-1,2,3-triazol-1-yl)phenyl)benzenesulfonamide |
| 43 | ethyl 1-(2-(4-tert-butylphenylsulfonamido)-5-chlorophenyl)-1H-1,2,3-triazole-4-carboxylate |
| 44 | N-(2-(5-amino-1H-pyrrolo[3,2-b]pyridin-1-yl)-4-chlorophenyl)-4-tert-butylbenzenesulfonamide |
| 45 | 4-tert-butyl-N-(4-chloro-2-(5-methyl-1H-[1,2,3]triazolo[4,5-b]pyridin-1-yl)phenyl)benzenesulfonamide |
| 46 | N-(2-(1H-[1,2,3]triazolo[4,5-b]pyridin-1-yl)-4-chlorophenyl)-4-isopropylbenzenesulfonamide |
| 47 | N-(2-(5-amino-1H-[1,2,3]triazolo[4,5-b]pyridin-1-yl)-4-chlorophenyl)-4-tert-butylbenzenesulfonamide |
| 48 | 1-(2-(4-tert-butylphenylsulfonamido)-5-chlorophenyl)-N-methyl-1H-1,2,3-triazole-4-carboxamide |
| 49 | 1-(2-(4-tert-butylphenylsulfonamido)-5-chlorophenyl)-N,N-dimethyl-1H-1,2,3-triazole-4-carboxamide |
| 50 | N-(2-(4-(azetidine-1-carbonyl)-1H-1,2,3-triazol-1-yl)-4-chlorophenyl)-4-tert-butylbenzenesulfonamide |
| 51 | 4-tert-butyl-N-(4-chloro-2-(4-(4-methylpiperazine-1-carbonyl)-1H-1,2,3-triazol-1-yl)phenyl)benzenesulfonamide |
| 52 | 1-(2-(4-tert-butylphenylsulfonamido)-5-chlorophenyl)-1H-1,2,3-triazole-4-carboxamide |
| 53 | 1-(2-(4-tert-butylphenylsulfonamido)-5-chlorophenyl)-1H-1,2,3-triazole-4-carboxylic acid |
| 54 | 4-tert-butyl-N-(4-chloro-2-(4-(dimethylamino)-1H-pyrazolo[4,3-c]pyridin-1-yl)phenyl)benzenesulfonamide |
| 55 | N-(2-(4-amino-1H-[1,2,3]triazolo[4,5-c]pyridin-1-yl)-4-chlorophenyl)-4-tert-butylbenzenesulfonamide |
| 56 | N-(2-(4-amino-1H-pyrazolo[4,3-c]pyridin-1-yl)-4-chlorophenyl)-4-tert-butylbenzenesulfonamide |
| 57 | 4-tert-butyl-N-(4-chloro-2-(4-oxo-4,5-dihydro-1H-pyrazolo[4,3-c]pyridin-1-yl)phenyl)benzenesulfonamide |
| 58 | 4-tert-butyl-N-(4-chloro-2-(4-morpholino-1H-[1,2,3]triazolo[4,5-c]pyridin-1-yl)phenyl)benzenesulfonamide |
| 59 | 4-tert-butyl-N-(4-morpholino-2-(4-morpholino-1H-[1,2,3]triazolo[4,5-c]pyridin-1-yl)phenyl)benzenesulfonamide |
| 60 | 4-tert-butyl-N-(3,4-dichloro-2-(1H-pyrazol-1-yl)phenyl)benzenesulfonamide |
| 61 | N-(2-(1H-[1,2,3]triazolo[4,5-b]pyridin-1-yl)-4-cyanophenyl)-4-tert-butylbenzenesulfonamide |
| 62 | 4-tert-butyl-N-(4-chloro-2-(5-methyl-4,5,6,7-tetrahydro-1H-[1,2,3]triazolo[4,5-b]pyridin-1-yl)phenyl)benzenesulfonamide |
| 63 | 4-tert-butyl-N-(4-chloro-2-(4,5,6,7-tetrahydro-1H-[1,2,3]triazolo[4,5-b]pyridin-1-yl)phenyl)benzenesulfonamide |
| 64 | 4-tert-butyl-N-(4-chloro-2-(4-(2-methoxyethyl)-4,5,6,7-tetrahydro-1H-[1,2,3]triazolo[4,5-b]pyridin-1-yl)phenyl)benzenesulfonamide |
| 65 | 4-tert-butyl-N-(4-chloro-2-(4-methyl-4,5,6,7-tetrahydro-1H-[1,2,3]triazolo[4,5-b]pyridin-1-yl)phenyl)benzenesulfonamide |
| 66 | 4-tert-butyl-N-(4-chloro-2-(4-ethyl-4,5,6,7-tetrahydro-1H-[1,2,3]triazolo[4,5-b]pyridin-1-yl)phenyl)benzenesulfonamide |
| 67 | 4-tert-butyl-N-(4-chloro-2-(4-isopropyl-4,5,6,7-tetrahydro-1H-[1,2,3]triazolo[4,5-b]pyridin-1-yl)phenyl)benzenesulfonamide |
| 68 | N-(2-(4-acetyl-4,5,6,7-tetrahydro-1H-[1,2,3]triazolo[4,5-b]pyridin-1-yl)-4-chlorophenyl)-4-tert-butylbenzenesulfonamide |
| 69 | 4-tert-butyl-N-(4-chloro-2-(4-(methylsulfonyl)-4,5,6,7-tetrahydro-1H-[1,2,3]triazolo[4,5-b]pyridin-1-yl)phenyl)benzenesulfonamide |
| 70 | 4-tert-butyl-N-(4-chloro-2-(5-isopropyl-1H-1,2,3-triazol-1-yl)phenyl)benzenesulfonamide |
| 71 | 4-tert-butyl-N-(4-chloro-2-(5-ethyl-1H-1,2,3-triazol-1-yl)phenyl)benzenesulfonamide |
| 72 | 4-tert-butyl-N-(4-chloro-2-(5-(morpholinomethyl)-1H-1,2,3-triazol-1-yl)phenyl)benzenesulfonamide |
| 73 | 4-tert-butyl-N-(4-chloro-2-(4-((dimethylamino)methyl)-1H-1,2,3-triazol-1-yl)phenyl)benzenesulfonamide |
| 74 | 4-tert-butyl-N-(4-chloro-2-(5-(pyrrolidin-1-ylmethyl)-1H-1,2,3-triazol-1-yl)phenyl)benzenesulfonamide |
| 75 | N-(2-(1H-[1,2,3]triazolo[4,5-b]pyridin-1-yl)-4-chlorophenyl)-3-fluoro-4-morpholinobenzenesulfonamide |
| 76 | 4-tert-butyl-N-(4-chloro-2-(4-(2-hydroxypropan-2-yl)-1H-pyrazol-1-yl)phenyl)benzenesulfonamide |
| 77 | 4-tert-butyl-N-(5-chloro-2-(1H-pyrazolo[4,3-b]pyridin-1-yl)pyridin-3-yl)benzenesulfonamide |
| 78 | 4-tert-butyl-N-(5-chloro-2-(5-methyl-1H-pyrazolo[4,3-b]pyridin-1-yl)pyridin-3-yl)benzenesulfonamide |
| 79 | 4-tert-butyl-N-(5-chloro-2-(1H-imidazo[4,5-b]pyridin-1-yl)pyridin-3-yl)benzenesulfonamide |
| 80 | 4-tert-butyl-N-(5-chloro-2-(3H-imidazo[4,5-b]pyridin-3-yl)pyridin-3-yl)benzenesulfonamide |

-continued

| Structure | Name |
|---|---|
| 81 | N-(2-(5-amino-1H-pyrrolo[3,2-b]pyridin-1-yl)-5-chloropyridin-3-yl)-4-tert-butylbenzenesulfonamide |
| 82 | N-(2-(1H-[1,2,3]triazolo[4,5-b]pyridin-1-yl)-5-chloropyridin-3-yl)-4-tert-butylbenzenesulfonamide |
| 83 | ethyl 1-(3-(4-tert-butylphenylsulfonamido)-5-chloropyridin-2-yl)-1H-pyrazole-4-carboxylate |
| 84 | N-(2-(1H-[1,2,3]triazolo[4,5-b]pyridin-1-yl)-5-methylpyridin-3-yl)-4-tert-butylbenzenesulfonamide |
| 85 | 4-tert-butyl-N-(5-chloro-2-(4-chloro-1H-pyrazol-1-yl)pyridin-3-yl)benzenesulfonamide |
| 86 | 4-tert-butyl-N-(5-chloro-2-(4-methyl-1H-imidazol-1-yl)pyridin-3-yl)benzenesulfonamide |
| 87 | 4-tert-butyl-N-(5-chloro-2-(4-phenyl-1H-imidazol-1-yl)pyridin-3-yl)benzenesulfonamide |
| 88 | 4-tert-butyl-N-(5-chloro-2-(2-methyl-1H-imidazol-1-yl)pyridin-3-yl)benzenesulfonamide |
| 89 | 4-tert-butyl-N-(5-chloro-2-(2-isopropyl-1H-imidazol-1-yl)pyridin-3-yl)benzenesulfonamide |
| 90 | 4-tert-butyl-N-(5-chloro-2-(2-phenyl-1H-imidazol-1-yl)pyridin-3-yl)benzenesulfonamide |
| 91 | 4-tert-butyl-N-(5-chloro-2-(2-ethyl-1H-imidazol-1-yl)pyridin-3-yl)benzenesulfonamide |
| 92 | 4-tert-butyl-N-(5-chloro-2-(1H-indol-1-yl)pyridin-3-yl)benzenesulfonamide |
| 93 | N-(2-(1H-benzo[d]imidazol-1-yl)-5-chloropyridin-3-yl)-4-tert-butylbenzenesulfonamide |
| 94 | 4-tert-butyl-N-(5-chloro-2-(1H-indazol-1-yl)pyridin-3-yl)benzenesulfonamide |
| 95 | N-(2-(1H-benzo[d][1,2,3]triazol-1-yl)-5-chloropyridin-3-yl)-4-tert-butylbenzenesulfonamide |
| 96 | 4-tert-butyl-N-(5-chloro-2-(9H-purin-9-yl)pyridin-3-yl)benzenesulfonamide |
| 97 | 4-tert-butyl-N-(5-chloro-2-(2,4-dimethyl-1H-imidazol-1-yl)pyridin-3-yl)benzenesulfonamide |
| 98 | 4-tert-butyl-N-(5-chloro-2-(2-ethyl-4-methyl-1H-imidazol-1-yl)pyridin-3-yl)benzenesulfonamide |
| 99 | 4-tert-butyl-N-(5-chloro-2-(4-(piperidine-1-carbonyl)-1H-pyrazol-1-yl)pyridin-3-yl)benzenesulfonamide |
| 100 | 4-tert-butyl-N-(5-chloro-2-(4-(morpholine-4-carbonyl)-1H-pyrazol-1-yl)pyridin-3-yl)benzenesulfonamide |
| 101 | 4-tert-butyl-N-(5-chloro-2-(4-(pyrrolidine-1-carbonyl)-1H-pyrazol-1-yl)pyridin-3-yl)benzenesulfonamide |
| 102 | 4-tert-butyl-N-(5-chloro-2-(4-(4-methylpiperazine-1-carbonyl)-1H-pyrazol-1-yl)pyridin-3-yl)benzenesulfonamide |
| 103 | N-(2-(4-(azetidine-1-carbonyl)-1H-pyrazol-1-yl)-5-chloropyridin-3-yl)-4-tert-butylbenzenesulfonamide |
| 104 | 1-(3-(4-tert-butylphenylsulfonamido)-5-chloropyridin-2-yl)-N-isopropyl-N-methyl-1H-pyrazole-4-carboxamide |
| 105 | 4-tert-butyl-N-(5-chloro-2-(4-(4-isopropylpiperazine-1-carbonyl)-1H-pyrazol-1-yl)pyridin-3-yl)benzenesulfonamide |
| 106 | 4-tert-butyl-N-(5-chloro-2-(4-(3-(dimethylamino)pyrrolidine-1-carbonyl)-1H-pyrazol-1-yl)pyridin-3-yl)benzenesulfonamide |
| 107 | 1-(3-(4-tert-butylphenylsulfonamido)-5-chloropyridin-2-yl)-N-(2-(dimethylamino)ethyl)-N-methyl-1H-pyrazole-4-carboxamide |
| 108 | 4-tert-butyl-N-(5-chloro-2-(4-(1,2,3,6-tetrahydropyridine-1-carbonyl)-1H-pyrazol-1-yl)pyridin-3-yl)benzenesulfonamide |
| 109 | 1-(3-(4-tert-butylphenylsulfonamido)-5-chloropyridin-2-yl)-N-methyl-1H-pyrazole-4-carboxamide |
| 110 | 1-(3-(4-tert-butylphenylsulfonamido)-5-chloropyridin-2-yl)-N,N-dimethyl-1H-pyrazole-4-carboxamide |
| 111 | 1-(3-(4-tert-butylphenylsulfonamido)-5-chloropyridin-2-yl)-N,3-dimethyl-1H-pyrazole-4-carboxamide |
| 112 | 1-(3-(4-tert-butylphenylsulfonamido)-5-chloropyridin-2-yl)-N,N,3-trimethyl-1H-pyrazole-4-carboxamide |
| 113 | 1-(3-(4-tert-butylphenylsulfonamido)-5-chloropyridin-2-yl)-1H-pyrazole-4-carboxylic acid |
| 114 | N-(2-(4-amino-1H-pyrazol-1-yl)-5-chloropyridin-3-yl)-4-tert-butylbenzenesulfonamide |
| 115 | N-(1-(3-(4-tert-butylphenylsulfonamido)-5-chloropyridin-2-yl)-1H-pyrazol-4-yl)acetamide |
| 116 | 4-tert-butyl-N-(5-chloro-2-(4-(oxazol-2-yl)-1H-pyrazol-1-yl)pyridin-3-yl)benzenesulfonamide |
| 117 | 4-tert-butyl-N-(4-chloro-2-(1H-indazol-3-yl)phenyl)benzenesulfonamide |
| 118 | 4-tert-butyl-N-(4-chloro-2-(1H-pyrrolo[2,3-b]pyridin-3-yl)phenyl)benzenesulfonamide |
| 119 | N-(2-(1H-[1,2,3]triazolo[4,5-b]pyridin-1-yl)-4-chlorophenyl)-4-acetylbenzenesulfonamide |
| 120 | N-(2-(1H-[1,2,3]triazolo[4,5-b]pyridin-1-yl)-4-chlorophenyl)-4-(1-(hydroxyimino)ethyl)benzenesulfonamide |

-continued

| Structure | Name |
|---|---|
| 121 | N-(2-(1H-[1,2,3]triazolo[4,5-b]pyridin-1-yl)-4-chlorophenyl)-4-(1-(methoxyimino)ethyl)benzenesulfonamide |
| 122 | N-(2-(1H-[1,2,3]triazolo[4,5-b]pyridin-1-yl)-4-chlorophenyl)-4-(1-aminoethyl)benzenesulfonamide |
| 123 | N-(2-(1H-[1,2,3]triazolo[4,5-b]pyridin-1-yl)-4-chlorophenyl)-4-(1-(methylamino)ethyl)benzenesulfonamide |
| 124 | N-(2-(1H-[1,2,3]triazolo[4,5-b]pyridin-1-yl)-4-chlorophenyl)-4-(1-(dimethylamino)ethyl)benzenesulfonamide |
| 125 | N-(2-(1H-[1,2,3]triazolo[4,5-b]pyridin-1-yl)-4-chlorophenyl)-4-(1-morpholinoethyl)benzenesulfonamide |
| 126 | N-(4-Chloro-2 [1,2,3]triazolo[4,5-b]pyridin-1-yl-phenyl)-4-(1-hydroxy-1-methyl-ethyl)-benzene-sulfonamide |
| 127 | N-(2-(1H-[1,2,3]triazolo[4,5-b]pyridin-1-yl)-4-chlorophenyl)-4-(1-(ethoxyimino)ethyl)benzenesulfonamide |
| 128 | N-(2-(1H-[1,2,3]triazolo[4,5-b]pyridin-1-yl)-4-chlorophenyl)-4-(1-(allyloxyimino)ethyl)benzenesulfonamide |
| 129 | N-(2-(1H-[1,2,3]triazolo[4,5-b]pyridin-1-yl)-4-chlorophenyl)-4-(1-(tert-butoxyimino)ethyl)benzenesulfonamide |
| 130 | 2-(1-(4-(N-(2-(1H-[1,2,3]triazolo[4,5-b]pyridin-1-yl)-4-chlorophenyl)sulfamoyl)phenyl)ethylideneaminooxy)acetic acid |
| 131 | N-(2-(1H-[1,2,3]triazolo[4,5-b]pyridin-1-yl)-4-chlorophenyl)-4-(1-hydroxy-2-methylpropan-2-yl)benzenesulfonamide |
| 132 | methyl 2-(4-(N-(2-(1H-[1,2,3]triazolo[4,5-b]pyridin-1-yl)-4-chlorophenyl)sulfamoyl)phenyl)-2-methylpropanoate |
| 133 | N-(2-(1H-[1,2,3]triazolo[4,5-b]pyridin-1-yl)-4-chlorophenyl)-4-isopropylbenzenesulfonamide |
| 134 | N-(2-(1H-[1,2,3]triazolo[4,5-b]pyridin-1-yl)-4-chlorophenyl)-4-cyanobenzenesulfonamide |
| 135 | N-(2-(1H-[1,2,3]triazolo[4,5-b]pyridin-1-yl)-4-chlorophenyl)-4-(1-hydroxyethyl)benzenesulfonamide |
| 136 | N-(2-(1H-[1,2,3]triazolo[4,5-b]pyridin-1-yl)-4-chlorophenyl)-4-(1,1,1-trifluoro-2-hydroxypropan-2-yl)benzenesulfonamide |
| 137 | N-(2-(1H-[1,2,3]triazolo[4,5-b]pyridin-1-yl)-4-chlorophenyl)-4-(2-hydroxybutan-2-yl)benzenesulfonamide |
| 138 | 4-tert-butyl-N-(4-chloro-2-(5-methyl-1H-1,2,3-triazol-1-yl)phenyl)benzenesulfonamide |
| 139 | 4-tert-butyl-N-(4-chloro-2-(4-(1-hydroxyethyl)-5-methyl-1H-1,2,3-triazol-1-yl)phenyl)benzenesulfonamide |
| 140 | N-(2-(1H-[1,2,3]triazolo[4,5-b]pyridin-1-yl)-4-chlorophenyl)-4-iodobenzenesulfonamide |
| 141 | 4-tert-butyl-N-(4-chloro-2-(4-ethynyl-5-methyl-1H-1,2,3-triazol-1-yl)phenyl)benzenesulfonamide |
| 142 | 4-tert-butyl-N-(4-chloro-2-(4-ethyl-5-methyl-1H-1,2,3-triazol-1-yl)phenyl)benzenesulfonamide |
| 143 | methyl 1-(2-(4-tert-butylphenylsulfonamido)-5-chlorophenyl)-5-methyl-1H-1,2,3-triazole-4-carboxylate |
| 144 | 4-tert-butyl-N-(4-chloro-2-(5-methyl-4-((methylamino)methyl)-1H-1,2,3-triazol-1-yl)phenyl)benzenesulfonamide |
| 145 | 4-tert-butyl-N-(4-chloro-2-(4-((isopropylamino)methyl)-5-methyl-1H-1,2,3-triazol-1-yl)phenyl)benzenesulfonamide |
| 146 | 4-tert-butyl-N-(4-chloro-2-(4-((cyclopropylamino)methyl)-5-methyl-1H-1,2,3-triazol-1-yl)phenyl)benzenesulfonamide |
| 147 | 4-tert-butyl-N-(4-chloro-2-(4-((dimethylamino)methyl)-5-methyl-1H-1,2,3-triazol-1-yl)phenyl)benzenesulfonamide |
| 148 | 4-tert-butyl-N-(4-chloro-2-(5-methyl-4-(morpholinomethyl)-1H-1,2,3-triazol-1-yl)phenyl)benzenesulfonamide |
| 149 | 4-tert-butyl-N-(4-chloro-2-(5-methyl-4-(thiazol-2-yl)-1H-1,2,3-triazol-1-yl)phenyl)benzenesulfonamide |
| 150 | 1-(2-(4-tert-butylphenylsulfonamido)-5-chlorophenyl)-5-methyl-1H-1,2,3-triazole-4-carboxylic acid |
| 151 | 4-tert-butyl-N-(4-chloro-2-(5-methyl-4-(oxazol-2-yl)-1H-1,2,3-triazol-1-yl)phenyl)benzenesulfonamide |
| 152 | 4-tert-butyl-N-(4-chloro-2-(4-(hydroxymethyl)-1H-pyrazol-1-yl)phenyl)benzenesulfonamide |
| 153 | 4-tert-butyl-N-(4-chloro-2-(4-((isopropylamino)methyl)-1H-pyrazol-1-yl)phenyl)benzenesulfonamide |
| 154 | 4-tert-butyl-N-(4-chloro-2-(4-((methylamino)methyl)-1H-pyrazol-1-yl)phenyl)benzenesulfonamide |
| 155 | 4-tert-butyl-N-(4-chloro-2-(4-(morpholinomethyl)-1H-pyrazol-1-yl)phenyl)benzenesulfonamide |
| 156 | 4-tert-butyl-N-(4-chloro-2-(4-((dimethylamino)methyl)-1H-pyrazol-1-yl)phenyl)benzenesulfonamide |
| 157 | ethyl 1-(2-(4-tert-butylphenylsulfonamido)-5-chlorophenyl)-5-methyl-1H-pyrazole-4-carboxylate |
| 158 | 4-tert-butyl-N-(4-chloro-2-(4-(2-hydroxypropan-2-yl)-5-methyl-1H-pyrazol-1-yl)phenyl)benzenesulfonamide |

-continued

| Structure | Name |
|---|---|
| 159 | N-(4-Chloro-2-[1,2,3]triazolo[4,5-b]pyridin-1-yl-phenyl)-3-fluoro-4-(1-hydroxy-1-methyl-ethyl)-benzenesulfonamide |
| 160 | N-(2-(1H-[1,2,3]triazolo[4,5-b]pyridin-1-yl)-4-chlorophenyl)-4-(2-hydroxypropan-2-yl)-3-methylbenzenesulfonamide |
| 161 | N-(2-(1H-[1,2,3]triazolo[4,5-b]pyridin-1-yl)-4-chlorophenyl)-3-chloro-4-(2-hydroxypropan-2-yl)benzenesulfonamide |
| 162 | N-(2-(1H-[1,2,3]triazolo[4,5-b]pyridin-1-yl)-4-chlorophenyl)-4-(2-hydroxypropan-2-yl)-3-methoxybenzenesulfonamide |
| 163 | N-(2-(1H-[1,2,3]triazolo[4,5-b]pyridin-1-yl)-4-chlorophenyl)-4-(2-hydroxypropan-2-yl)-3-(trifluoromethyl)benzenesulfonamide |

Reagents and solvents used below can be obtained from commercial sources such as Aldrich Chemical Co. (Milwaukee, Wis., USA). ¹H-NMR were recorded on a Varian Mercury 400 MHz NMR spectrometer. Significant peaks are tabulated in the order: multiplicity (br, broad; s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H, M+Na, etc.) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH₄OAc in acetonitrile/water as delivery system.

General Procedure A

Example 4-tert-Butyl-N-(4-chloro-2-iodo-phenyl)-benzenesulfonamide

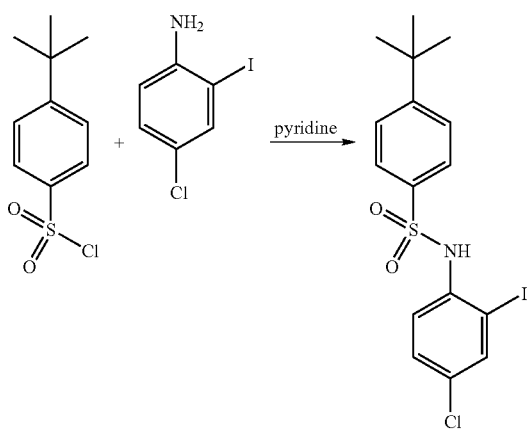

A 100 mL round-bottom flask was charged with 2-iodo-4-chloroaniline (8.40 g, 33.2 mmol) and 4-tert-butyl benzenesulfonyl chloride (8.28 g, 35.5 mmol). The flask was evacuated and purged with nitrogen, followed by the addition of pyridine (33 mL). The homogeneous purple solution was stirred 4 hours (during which pyridine salts crashed out), and then poured onto a rapidly stirring cold slurry of 6 M HCl (66 mL) (formed by placing the acidic solution in acetonic dry ice). The resultant precipitated sulfonamide was filtered, washed thoroughly with 10% HCl, and dried in vacuo to afford 15.586 g of a purplish solid. To the crude sulfonamide was subsequently added 200 mL EtOH and the heterogeneous purple solution was vigorously stirred and heated until the volume was reduced to ~150 mL. The solution was then cooled to ambient temperature overnight and placed in the freezer for 2 hours, during which the sulfonamide recrystallized from solution. The solid was filtered and washed with cold MeOH (0° C.) to produce the pure sulfonamide (14.2 g, 95%) as a white solid: MS (ES) M+H expected 450.0, found 450.1.

Example 4-tert-Butyl-N-(4-chloro-5-fluoro-2-iodo-phenyl)-benzenesulfonamide

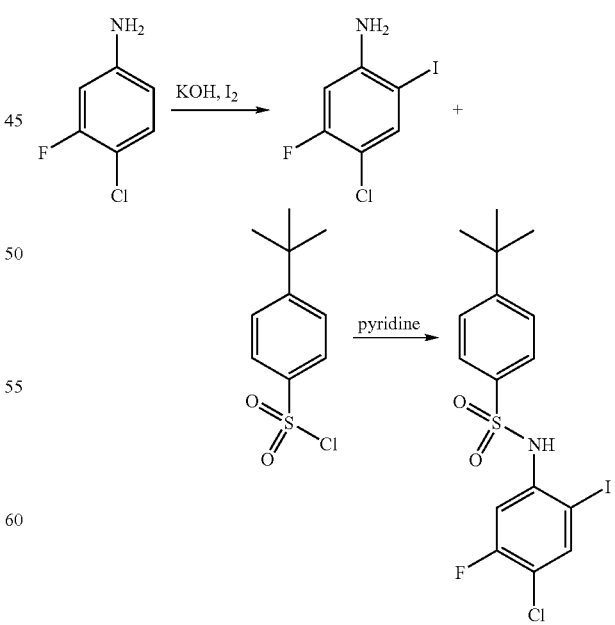

Step 1: Iodine (873 mg, 3.44 mmol) was added to a solution of 4-chloro-3-fluoroaniline (500 mg, 3.44 mmol) and potassium hydroxide (193 mg, 3.44 mmol) in N,N-dimethylformamide ("DMF") (10 mL) and the reaction was stirred at 60° C. for 18 hours. The crude mixture was subsequently partitioned with ethyl acetate (20 mL) and saturated ammonium chloride (20 mL) and the layers separated. The organic layer was washed with saturated ammonium chloride (3×20 mL), dried over magnesium sulfate, filtered, and concentrated in vacuo. The crude material was purified by flash column chromatography (0-50% ethyl acetate in hexanes) to afford the desired iodoaniline (234 mg, 25%).

Step 2: 4-tert-Butyl-N-(4-chloro-5-fluoro-2-iodo-phenyl)-benzenesulfonamide was synthesized from the above iodoaniline and 4-tert-butyl benzenesulfonyl chloride according to general procedure A: MS (ES) M+H expected 468.0, found 467.9.

Example

N-(2-Bromo-5-chloro-pyridin-3-yl)-4-tert-butyl-benzenesulfonamide

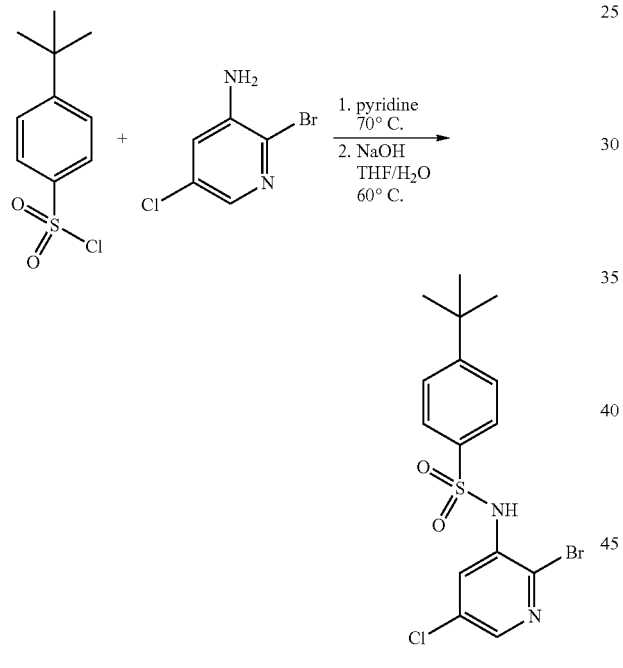

A 200 mL round-bottom flask was charged with 2-bromo-5-chloro-pyridin-3-ylamine (10.4 g, 50.0 mmol), 4-tert-butyl-benzenesulfonyl chloride (20.0 g, 85.0 mmol), and pyridine (38 mL). The resultant solution was heated to 70° C. and stirred overnight. The following day, the pyridine was removed by removed in vacuo and 30 mL THF (tetrahydrofuran) and 100 mL 4.0 N NaOH were added and the reaction was stirred at 60° C. overnight. The organics were subsequently removed in vacuo and the residues were diluted with 400 mL water. The small quantity of insoluble solid was removed by filtration and the pH was adjusted to 6-7 with concentrated HCl. The resultant aqueous solution was extracted with EtOAc, washed with brine, dried over MgSO$_4$, and concentrated under reduced pressure to afford the desired sulfonamide (13.4 g) in 66% yield: MS (ES) M+H expected 403.0, found 403.1.

General Procedure B

Example

N-(2-Bromo-4-chloro-phenyl)-4-tert-butyl-N-methoxymethyl-benzenesulfonamide

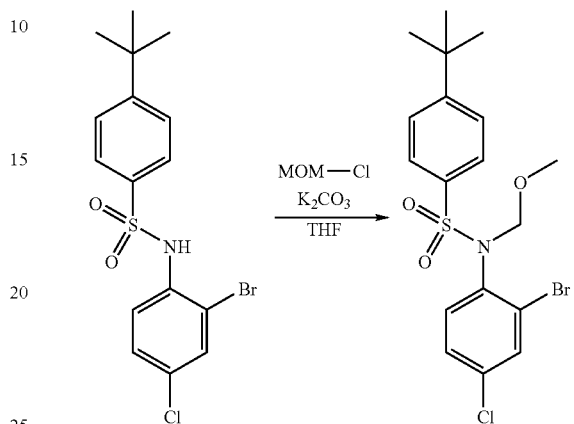

To a solution of N-(2-bromo-4-chloro-phenyl)-4-tert-butyl-benzenesulfonamide (1.00 g, 2.49 mmol) and K$_2$CO$_3$ (1.72 g, 12.4 mmol) in 8 mL anhydrous THF was added chloromethyl methyl ether (299 mg, 3.73 mmol). The resultant heterogeneous solution was stirred for 60 minutes at ambient temperature and the solids were subsequently removed via filtration. The filtrate was subsequently concentrated in vacuo and the residue was dissolved in EtOAc. The organics were washed with saturated Na$_2$CO$_3$, dried over MgSO$_4$, and evaporated in vacuo. The resultant residue was then purified via automated silica gel chromatography to afford the desired protected sulfonamide: MS (ES) M+H expected 446.0, found 446.0.

Example

N-(2-Bromo-5-chloro-pyridin-3-yl)-4-tert-butyl-N-methoxymethyl-benzenesulfonamide

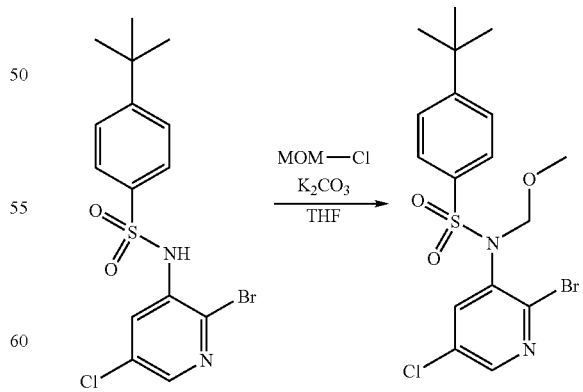

To a solution N-(2-bromo-5-chloro-pyridin-3-yl)-4-tert-butyl-benzenesulfonamide (12.0 g, 35.0 mmol) and K$_2$CO$_3$ (24.0 g, 170 mmol) in 80 mL anhydrous THF was added chloromethyl methyl ether (4.0 mL, 52.7 mmol). The resultant heterogeneous solution was stirred for 60 minutes at ambient temperature and the solids were subsequently removed via filtration. The filtrate was then removed in vacuo and the residue was dissolved in EtOAc. The organics were washed with saturated $Na_2CO_3$, dried over $MgSO_4$, and evaporated in vacuo to generate a brownish oil. The oil was finally triturated with hexanes and the resultant solid filtered to produce the desired product as a light yellowish solid (11.5 g, 86% yield): MS (ES) M+H expected 447.0, found 447.0.

General Procedure D

Example 4-tert-Butyl-N-(4-chloro-2-[1,2,3]triazolo[4,5-b]pyridine-1-yl-phenyl)-benzenesulfonamide

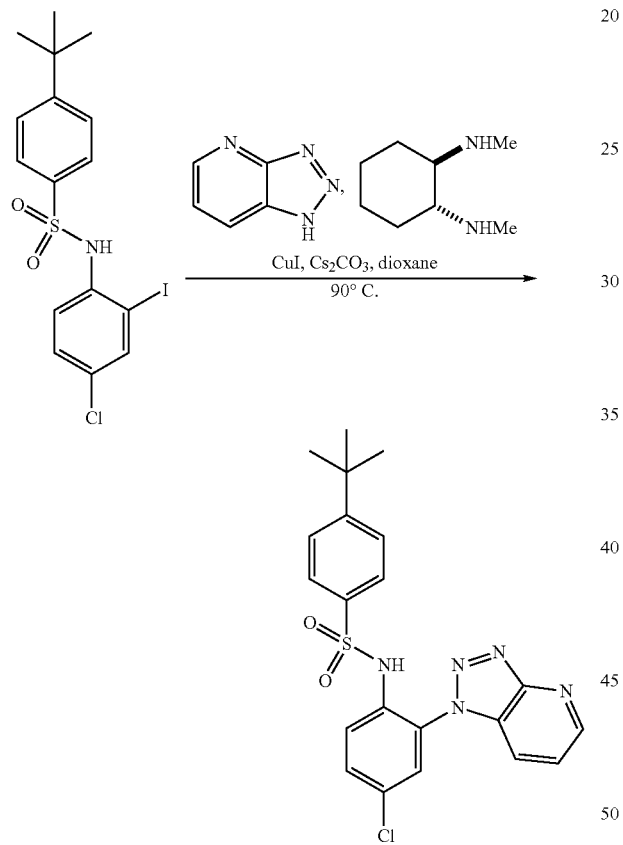

A 4 mL scintillation vial was charged with 4-tert-butyl-N-(4-chloro-2-iodo-phenyl)-benzenesulfonamide (84 mg, 0.19 mmol), 4-azabenzotriazole (29 mg, 0.22 mmol), CuI (3 mg, 0.014 mmol), $Cs_2CO_3$ (127 mg, 0.39 mmol), trans-N,N'-dimethylcyclohexane-1,2-diamine (5 mg, 0.04 mmol), and dioxane (500 μL). The reaction was heated to 90° C. and stirred overnight. The following day, the volatiles were removed in vacuo. The residue was subsequently diluted in EtOAc and washed with saturated $NH_4Cl$ (aq). The organic layer was then concentrated in vacuo and the residue purified by preparative TLC (thin-layer chromatography) to afford 4-tert-butyl-N-(4-chloro-2-[1,2,3]triazolo[4,5-b]pyridine-1-yl-phenyl)-benzenesulfonamide: MS (ES) M+H expected 442.1, found 442.0.

Example 4-tert-Butyl-N-(5-chloro-2-pyrazolo[4,3-b]pyridin-1-yl-pyridin-3-yl)-benzenesulfonamide

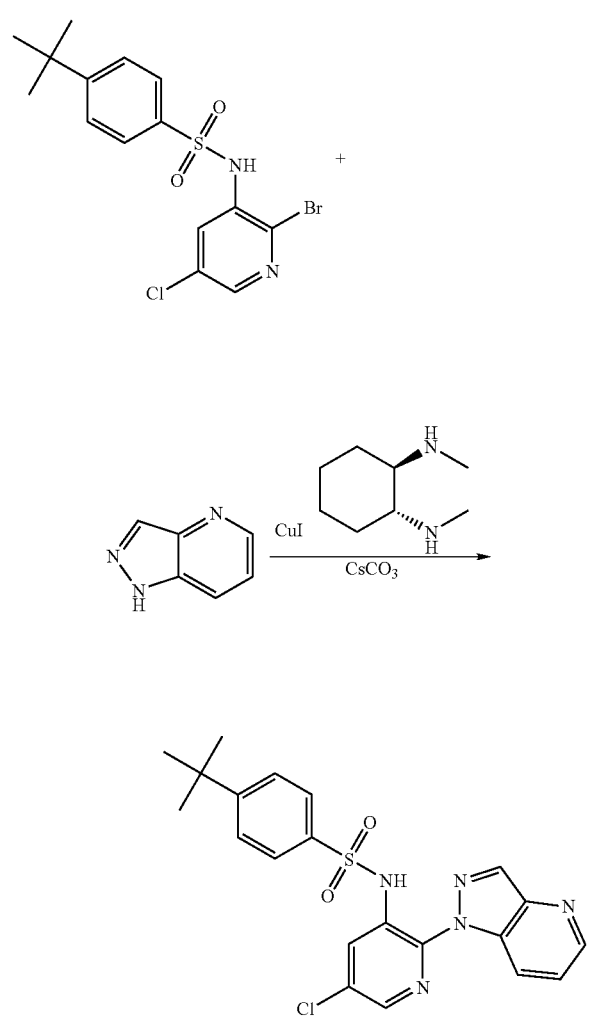

A solution of N-(2-bromo-5-chloro-pyridin-3-yl)-4-tert-butyl-benzene sulfonamide (226 mg, 0.559 mmol), 1H-pyrazolo[4,3-b]pyridine (100 mg, 0.839 mmol), trans-N,N'-dimethyl-cyclohexane-1,2-diamine (18 μL, 0.112 mmol), copper iodide (22 mg, 0.112 mmol), and cesium carbonate (383 mg, 1.17 mmol) in 2 mL of N,N-dimethylacetamide was heated at 130° C. for 2 hours. Ethyl acetate and water were added and the layers were separated. The organic layer was washed with brine, dried over magnesium sulfate, filtered, and concentrated in vacuo. The crude reside was subsequently purified by flash column chromatography (0-100% ethyl acetate in hexanes) to afford 4-tert-butyl-N-(5-chloro-2-pyrazolo[4,3-b]pyridin-1-yl-pyridin-3-yl)-benzenesulfonamide: MS (ES) M+H expected 442.1, found 442.0.

General Procedure E

Example

1-[2-(4-tert-Butyl-benzenesulfonylamino)-5-chloro-phenyl]-1H-pyrazole-4-carboxylic acid amide

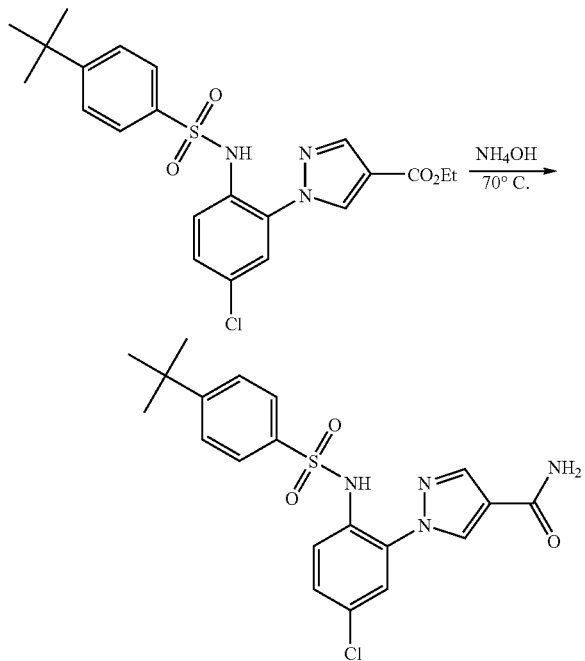

1-[2-(4-tert-butyl-benzenesulfonylamino)-5-chloro-phenyl]-1H-pyrazole-4-carboxylic acid ethyl ester (synthesized according to general procedure D, 55 mg, 0.119 mmol) and 1 mL of ammonium hydroxide were stirred at 70° C. for 18 hours. The resultant solution was partitioned between saturated sodium bicarbonate and dichloromethane, and the aqueous layer extracted with dichloromethane. The combined organic layers were dried over magnesium sulfate, filtered, and concentrated in vacuo. The crude product was subsequently purified by flash column chromatography (0-100% ethyl acetate in hexanes) to yield 1-[2-(4-tert-butyl-benzenesulfonylamino)-5-chloro-phenyl]-1H-pyrazole-4-carboxylic acid amide: MS (ES) M+H expected 433.1, found 433.0.

Example

1-[3-(4-tert-Butyl-benzenesulfonylamino)-5-chloro-pyridin-2-yl]-1H-pyrazole-4-carboxylic acid dimethylamide

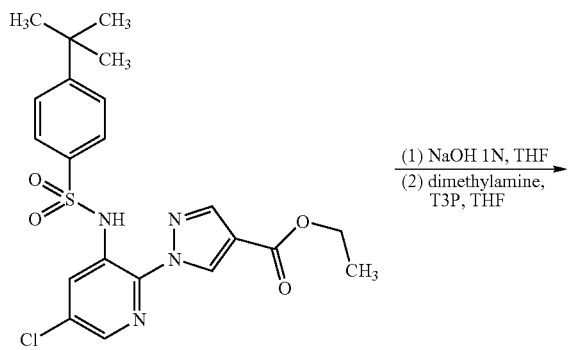

A 25 mL scintillation vial was charged with 1-[3-(4-tert-butyl-benzenesulfonylamino)-5-chloro-pyridin-2-yl]-1H-pyrazole-4-carboxylic acid ethyl ester (synthesized according to general procedure D, 93 mg, 0.2 mmol), NaOH (2 mL, 1.0 M solution in water), and THF (3 mL). The vial was sealed and stirred at 80° C. for 16 hours. The reaction solution was subsequently neutralized to pH=5 with glacial acetic acid. The mixture was extracted with ethyl acetate (2×10 mL) and the combined organics were concentrated in vacuo. The crude product was subsequently dissolved in 2 mL of THF in a 25 mL scintillation vial. To the resultant solution was added with dimethylamine (0.2 mL, 2.0 M in THF), 1-propanephosphonic anhydride solution (184 mg, 50% solution in ethyl acetate), and triethylamine (41 mg, 0.4 mmol). The vial was sealed and stirred at ambient temperature for 1 hour. The volatiles were then evacuated in vacuo and the residue was purified via preparative HPLC to afford 1-[3-(4-tert-butyl-benzenesulfonylamino)-5-chloro-pyridin-2-yl]-1H-pyrazole-4-carboxylic acid dimethylamide as a white powder: MS (ES) M+H expected 462.1, found 462.0.

General Procedure F

Example

4-Chloro-2-[1,2,3]triazolo[4,5-b]pyridin-1-yl-phenylamine

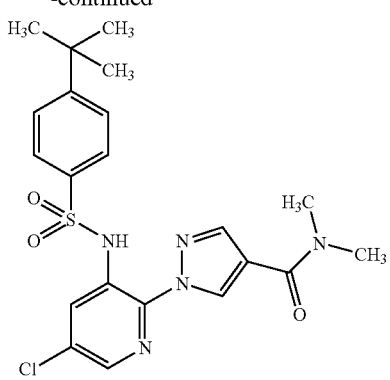

-continued

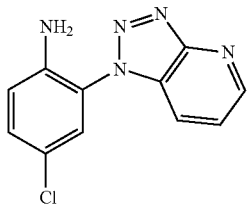

Step 1: 4-Chloro-2-fluoro-1-nitrobenzene (25 g, 142 mmol) and 1H-[1,2,3]triazolo[4,5-b]pyridine (18.8 g, 157 mmol) were slurried in DMF (50 mL) in a 200 mL round-bottom flask fitted with a magnetic stir bar. Potassium carbonate (29.5 g, 214 mmol) was added to the mixture and it was then heated while stirring in a 60° C. oil bath under $N_2$. LCMS analysis after two hours indicated complete consumption of the nitrobenzene and two different isomeric forms of the desired product. Water (250 mL) was subsequently added in a steady stream to the rapidly stirring mixture to precipitate the crude product. The resultant precipitate was collected by vacuum filtration and washed with 2×100 mL water.

The resultant damp filter was slurried with 50 mL toluene and the solids collected by vacuum filtration. This action was repeated three additional times and then the resultant solid was dried in vacuo to afford 21.6 g (55% yield) 1-(5-chloro-2-nitrophenyl)-1H-[1,2,3]triazolo[4,5-b]pyridine as an off-white solid.

Step 2: 1-(5-Chloro-2-nitrophenyl)-1H-[1,2,3]triazolo[4,5-b]pyridine (10 g, 36.3 mmol) was dissolved in 200 mL concentrated HCl in a 1 L round-bottom flask fitted with a magnetic stir bar. Iron powder (4.2 g, 74.4 mmol) was added in portions to the rapidly stirring solution. The resultant thick yellow slurry was allowed to stir overnight until no visible metallic iron was observed in the reaction vessel. The following day, LCMS analysis indicated complete reduction to the aniline. The mixture was subsequently transferred to a 500 mL Buchner funnel, with the assistance of a small amount of concentrated HCl to rinse out the remaining slurry from the reaction vessel, and the insoluble material was collected by vacuum filtration. The filter cake was then stirred into a thick paste with water (15 mL) and the solids collected by vacuum filtration. The material was again stirred in 15 mL water and filtered, the mother liquors were discarded, and the solid material dried in vacuo. The resultant light brown solid was slurried in 50 mL of 1:1 (v/v) EtOAc:acetonitrile and heated to the boiling point with a heat gun. The mixture was allowed to cool to room temperature and the solids were collected by vacuum filtration. The solids were subsequently washed with a small amount of 1:1 EtOAc:acetonitrile and dried in vacuo to generate 7.5 g 4-chloro-2-[1,2,3]triazolo[4,5-b]pyridin-1-yl-phenylamine (light grey solid, 84% yield): MS (ES) M+H expected 246.0, found 246.0.

Example

1-[3-(4-tert-Butyl-benzenesulfonylamino)-5-chloro-pyridin-2-yl]-1H-pyrazole-4-carboxylic acid

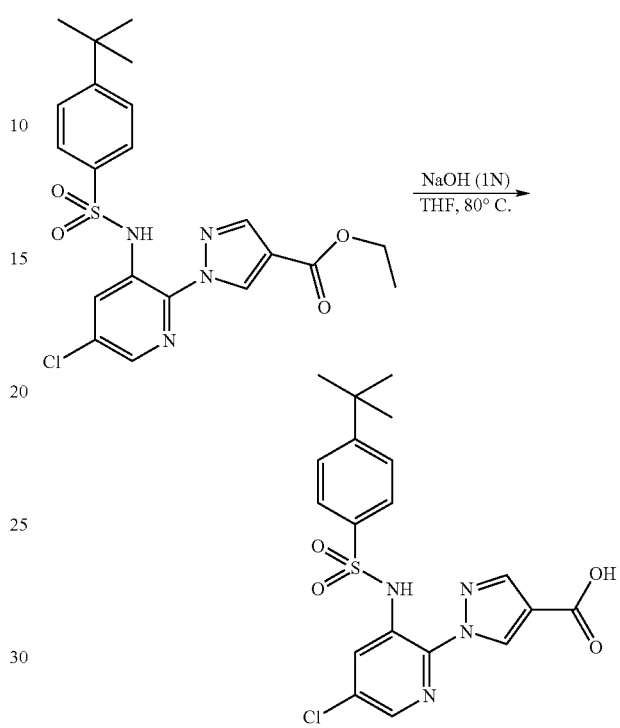

A 25 mL scintillation vial was charged with 1-[3-(4-tert-butyl-benzenesulfonylamino)-5-chloro-pyridin-2-yl]-1H-pyrazole-4-carboxylic acid ethyl ester (synthesized according to general procedure D, 93 mg, 0.2 mmol), NaOH (2 mL, 1.0 M solution in water), and THF (3 mL). The vial was sealed and stirred at 80° C. for 16 hours. The reaction solution was subsequently neutralized to pH=5 with glacial acetic acid. The mixture was extracted with ethyl acetate (2×10 mL) and the combined organics were concentrated in vacuo. The resultant residue was purified via preparative HPLC to afford 1-[3-(4-tert-butyl-benzenesulfonylamino)-5-chloro-pyridin-2-yl]-1H-pyrazole-4-carboxylic acid as a white powder: MS (ES) M+H expected 435.1, found 435.0.

General Procedure G

Example

N-(4-Chloro-2-[1,2,3]triazolo[4,5-b]pyridin-1-yl-phenyl)-4-(1,1-dimethyl-propyl)-benzenesulfonamide

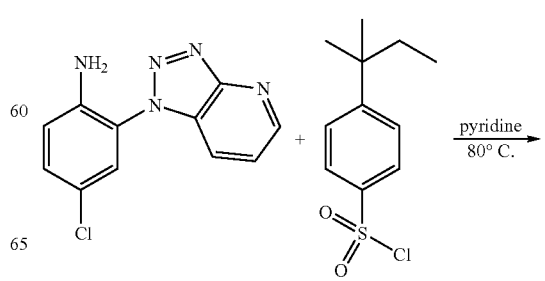

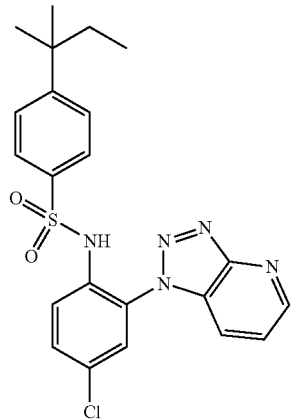

A 4 mL scintillation vial was charged with 4-chloro-2-[1,2,3]triazolo[4,5-b]pyridin-1-yl-phenylamine (100 mg, 0.363 mmol), 4-(1,1-dimethyl-propyl)-benzenesulfonyl chloride (98 g, 0.399 mmol), and pyridine (1 mL). The resultant solution was stirred 4 hours at 80° C. and then partitioned with EtOAc/1 M HCl. The organics were subsequently washed with 1 M HCl, saturated aqueous sodium bicarbonate, and brine; dried over anhydrous sodium sulfate; and removed in vacuo. The resultant residue was then purified via automated silica gel chromatography to afford the desired sulfonamide: MS (ES) M+H expected 456.2, found 456.3.

Example

N-[2-(4-Amino-pyrazol-1-yl)-5-chloro-pyridin-3-yl]-4-tert-butyl-benzenesulfonamide

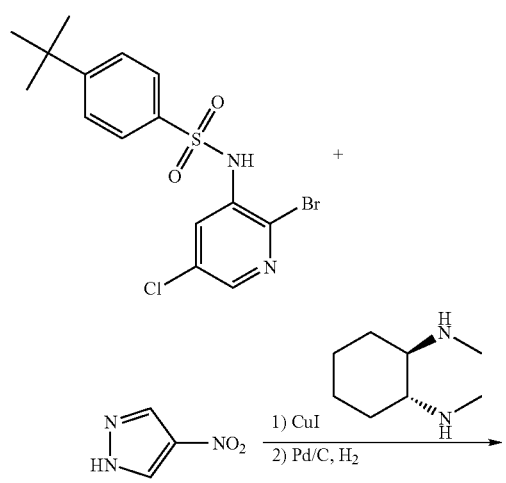

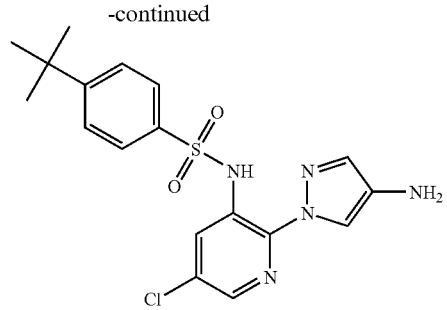

Step 1: A solution of N-(2-bromo-5-chloro-pyridin-3-yl)-4-tert-butyl-benzene sulfonamide (534 mg, 1.32 mmol), 4-nitropyrazole (224 mg, 1.98 mmol), trans-N,N'-dimethyl-cyclohexane-1,2-diamine (42 µL, 0.264 mmol), copper iodide (51 mg, 0.264 mmol), and cesium carbonate (903 mg, 2.77 mmol) in 5 mL of N,N-dimethylacetamide was heated at 130° C. for 2 hours. Ethyl acetate and water were added and the layers were separated. The organic layer was washed with brine, dried over magnesium sulfate, filtered, and concentrated in vacuo. The crude reside was subsequently purified by flash column chromatography (0-100% ethyl acetate in hexanes) to afford 4-tert-butyl-N-[5-chloro-2-(4-nitro-pyrazol-1-yl)-pyridin-3-yl]-benzenesulfonamide as a white solid.

Step 2: To a solution of 4-tert-butyl-N-[5-chloro-2-(4-nitro-pyrazol-1-yl)-pyridin-3-yl]-benzenesulfonamide (100 mg, 0.229 mmol) in 2 mL of ethanol was added 10% Pd/C and the heterogeneous solution was stirred under an atmosphere of hydrogen. After two hours, the reaction was filtered through celite and concentrated in vacuo. The crude reside was subsequently purified by flash column chromatography (0-100% ethyl acetate in hexanes) to afford N-[2-(4-amino-pyrazol-1-yl)-5-chloro-pyridin-3-yl]-4-tert-butyl-benzene sulfonamide as a white solid: MS (ES) M+H expected 406.1, found 406.0.

General Procedure H

Example

1-[2-(4-tert-Butyl-benzenesulfonylamino)-5-chloro-phenyl]-1H-[1,2,3]triazole-4-carboxylic acid amide

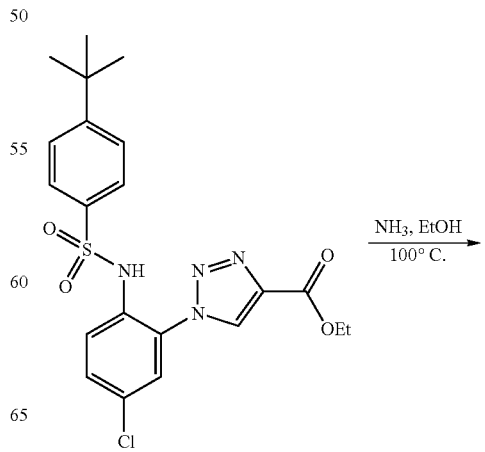

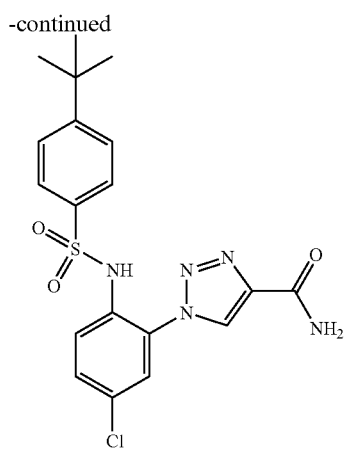

A 4 mL scintillation vial was charged with 1-[2-(4-tert-butyl-benzenesulfonylamino)-5-chloro-phenyl]-1H-[1,2,3]triazole-4-carboxylic acid ethyl ester (synthesized according to general procedure G, 10 mg, 0.02 mmol) and 2 M $NH_3$ in EtOH (1 mL). The reaction was heated to 100° C. and stirred overnight. The following day, the volatiles were removed in vacuo and the residue was purified by preparative TLC chromatography to afford 1-[2-(4-tert-butyl-benzenesulfonylamino)-5-chloro-phenyl]-1H-[1,2,3]triazole-4-carboxylic acid amide: MS (ES) M+H expected 434.1, found 434.0.

Example

N-{1-[3-(4-tert-Butyl-benzenesulfonylamino)-5-chloro-pyridin-2-yl]-1H-pyrazol-4-yl}-acetamide

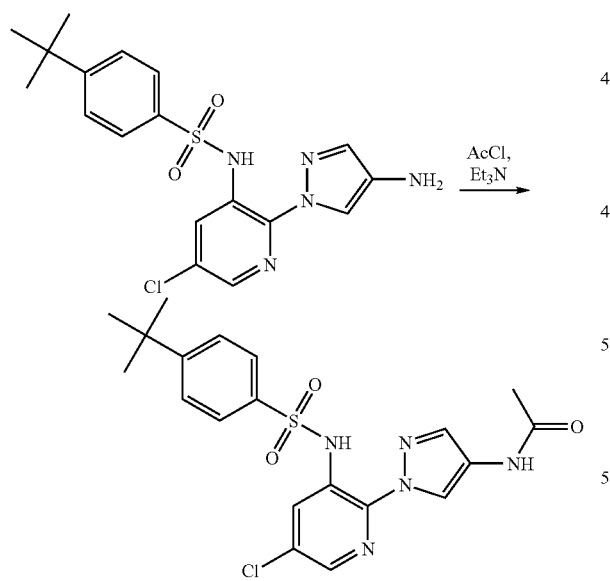

A solution of N-[2-(4-amino-pyrazol-1-yl)-5-chloro-pyridin-3-yl]-4-tert-butyl-benzenesulfonamide (20 mg, 0.049 mmol), acetyl chloride (3.5 μL, 0.049 mmol), and triethylamine (14 μL, 0.099 mmol) were stirred at room temperature for 1 hour. The reaction was concentrated in vacuo, followed by the addition of dicholoromethane (1 mL) and tetrabutylammonium fluoride (0.4 mL, 1.0 M in THF). The reaction was stirred for 2 hours at room temperature and then the crude mixture was partitioned with saturated sodium bicarbonate. The aqueous phase was subsequently extracted with dichloromethane and the combined organic layers dried over magnesium sulfate, filtered, and concentrated in vacuo. The crude product was purified by flash column chromatography (0-100% ethyl acetate in hexanes) to afford N-{1-[3-(4-tert-butyl-benzenesulfonylamino)-5-chloro-pyridin-2-yl]-1H-pyrazol-4-yl}-acetamide: MS (ES) M+H expected 448.1, found 448.0.

General Procedure I

Example

1-[2-(4-tert-Butyl-benzenesulfonylamino)-5-chloro-phenyl]-1H-[1,2,3]triazole-4-carboxylic acid

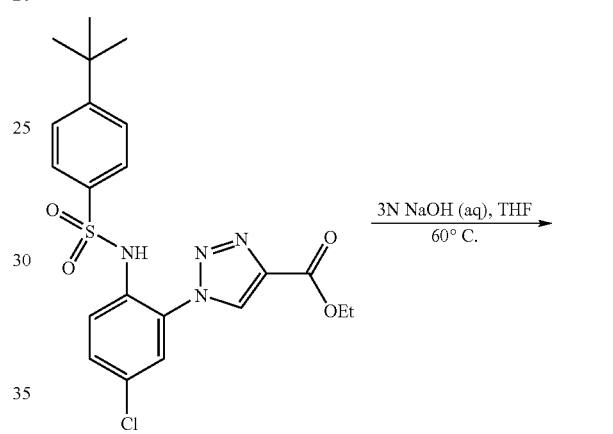

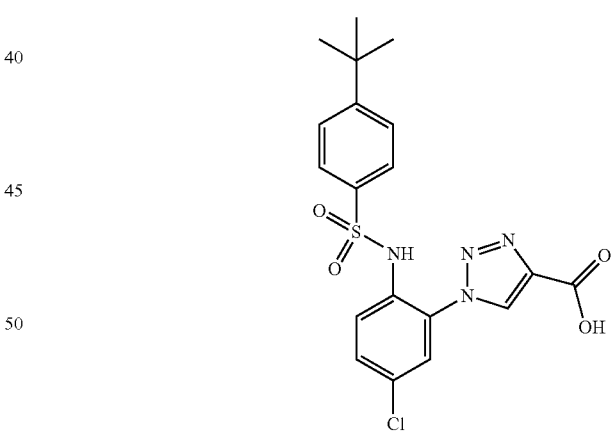

A 4 mL scintillation vial was charged with 1-[2-(4-tert-butyl-benzenesulfonylamino)-5-chloro-phenyl]-1H-[1,2,3]triazole-4-carboxylic acid ethyl ester (synthesized according to general procedure G, 10 mg, 0.02 mmol) and 3 M NaOH (aq)/THF (1:3) (1 mL). The reaction was heated to 60° C. and stirred overnight. The following day, the volatiles were removed in vacuo and the residue was purified by preparative TLC to afford 1-[2-(4-tert-butyl-benzenesulfonylamino)-5-chloro-phenyl]-1H-[1,2,3]triazole-4-carboxylic acid: MS (ES) M+H expected 435.1, found 435.0.

Example

4-tert-Butyl-N-[5-chloro-2-(4-oxazol-2-yl-pyrazol-1-yl)-pyridin-3-yl]-benzenesulfonamide

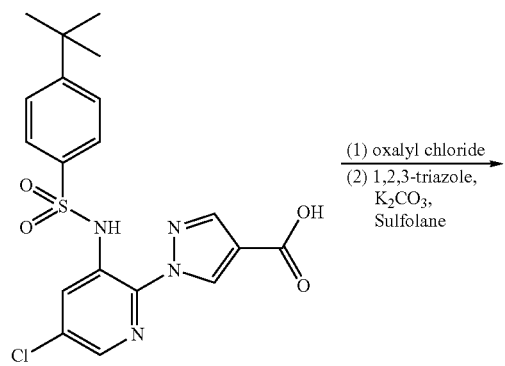

(1) oxalyl chloride
(2) 1,2,3-triazole, K$_2$CO$_3$, Sulfolane

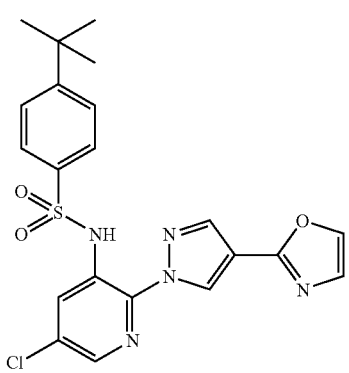

A 25 mL scintillation vial was charged with 1-[3-(4-tert-butyl-benzenesulfonylamino)-5-chloro-pyridin-2-yl]-1H-pyrazole-4-carboxylic acid (87 mg, 0.2 mmol), oxalyl chloride (2 mL, 1.0 M solution in dichloromethane), and dichloromethane (3 mL). The mixture was stirred at room temperature for 2 hours, the volatiles removed in vacuo, and the residue further dried at reduced pressure for 4 hours. The scintillation vial containing the crude acid chloride was subsequently charged with 1H-1,2,3-triazole (34 mg, 0.5 mmol), K$_2$CO$_3$ (138 mg, 1.0 mmol), and sulfolane (2 mL). The vial was sealed and stirred at 80° C. for 16 hours. The reaction solution was neutralized to pH=7 with glacial acetic acid. The mixture was extracted with ethyl acetate (2×10 mL) and the combined organics were concentrated in vacuo. The residue was purified via preparative HPLC to afford 4-tert-butyl-N-[5-chloro-2-(4-oxazol-2-yl-pyrazol-1-yl)-pyridin-3-yl]-benzenesulfonamide as a white powder: MS (ES) M+H expected 458.1, found 458.0.

General Procedure J

Example

N-[2-(4-Amino-[1,2,3]triazolo[4,5-c]pyridin-1-yl)-4-chloro-phenyl]-4-tert-butyl-benzenesulfonamide

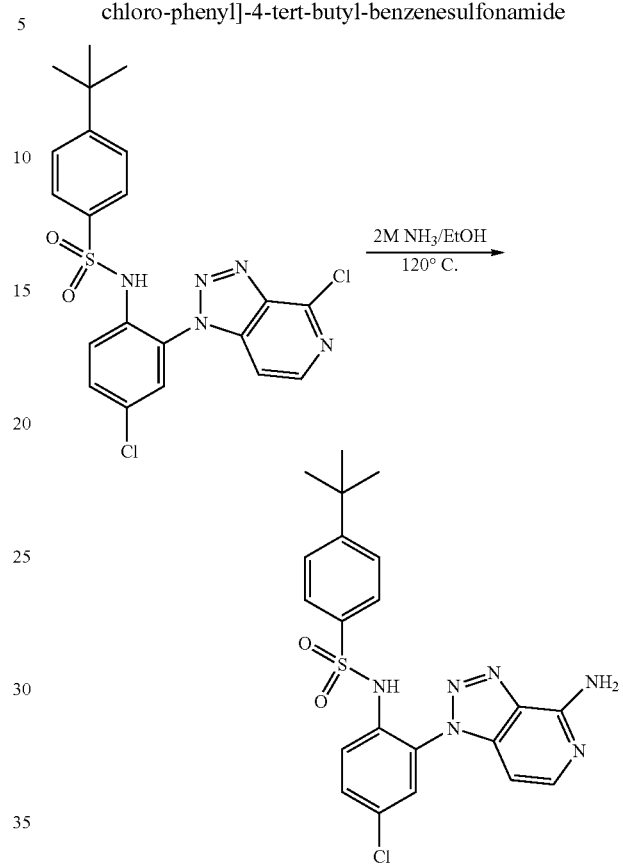

2M NH$_3$/EtOH
120° C.

A 4 mL scintillation vial was charged with 4-tert-butyl-N-[4-chloro-2-(4-chloro-[1,2,3]triazolo[4,5-c]pyridin-1-yl)-phenyl]-benzenesulfonamide (synthesized according to general procedure G, 20 mg, 0.042 mmol) and 2 M NH$_3$ in EtOH (2 mL). The reaction was sealed and heated to 120° C. for 18 hours. The EtOH was then removed in vacuo and the resultant residue was purified by preparative TLC to afford N-[2-(4-amino-[1,2,3]triazolo[4,5-c]pyridin-1-yl)-4-chloro-phenyl]-4-tert-butyl-benzenesulfonamide: MS (ES) M+H expected 457.1, found 457.0.

General Procedure K

Example

4-tert-Butyl-N-(4-cyano-2-[1,2,3]triazolo[4,5-b]pyridin-1-yl-phenyl)-benzenesulfonamide

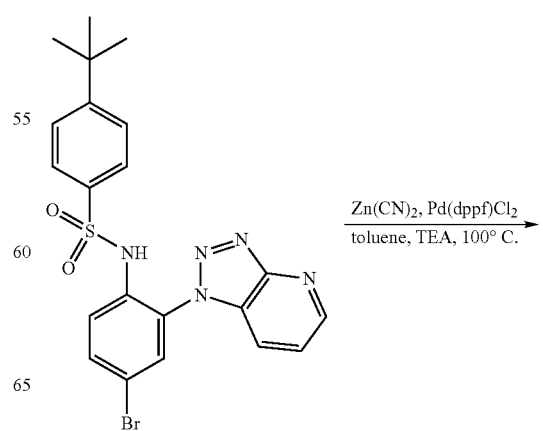

Zn(CN)$_2$, Pd(dppf)Cl$_2$
toluene, TEA, 100° C.

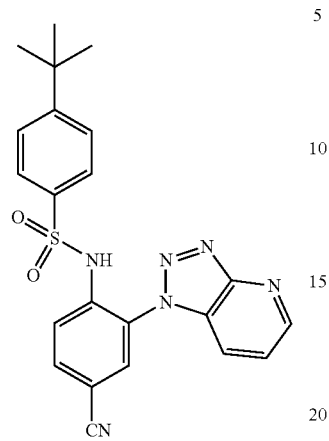

A 4 mL scintillation vial was charged with N-(4-bromo-2-[1,2,3]triazolo[4,5-b]pyridin-1-yl-phenyl)-4-tert-butyl-benzenesulfonamide (synthesized according to general procedure G, 20 mg, 0.04 mmol), $Zn(CN)_2$ (8 mg, 0.06 mmol), $Pd(dppf)Cl_2$ (4 mg, 0.005 mmol), TEA (10 µL, 0.07 mmol), and toluene (300 µL). The reaction was sealed and heated to 100° C. for 18 hours. The solvent was subsequently removed in vacuo and the resultant residue was purified by preparative TLC to afford 4-tert-butyl-N-(4-cyano-2-[1,2,3]triazolo[4,5-b]pyridin-1-yl-phenyl)-benzenesulfonamide: MS (ES) M+H expected 433.1, found 433.0.

General Procedure L

Example 4-tert-Butyl-N-(3,4-dichloro-2-pyrazol-1-yl-phenyl)-benzenesulfonamide

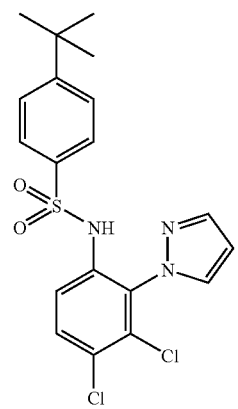

A 25 mL scintillation vial was charged with 4-tert-butyl-N-(4-chloro-2-pyrazol-1-yl-phenyl)-benzenesulfonamide (synthesized according to general procedure D, 78 mg, 0.2 mmol), N-chlorosuccinimide (67 mg, 0.5 mmol), benzoyl peroxide (2.4 mg, 0.01 mmol), and carbon tetrachloride (4 mL). The vial was sealed and stirred for 18 hours at 80° C. The resultant solution was partitioned between ethyl acetate and water and the combined organics were washed with 1 N HCl, saturated sodium bicarbonate, and brine; dried over magnesium sulfate; filtered; and concentrated in vacuo. The crude product was subsequently purified by flash column chromatography (10-100% ethyl acetate in hexanes) followed by preparative HPLC (10-90% gradient of MeCN:water) to afford the title compound as a white solid: MS (ES) M+H expected 424.1, found 424.1.

General Procedure M

Example 4-tert-Butyl-N-[4-chloro-2-(4,5,6,7-tetrahydro-[1,2,3]triazolo[4,5-b]pyridin-1-yl)-phenyl]-benzenesulfonamide

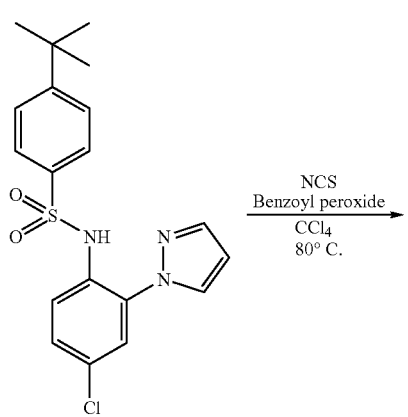

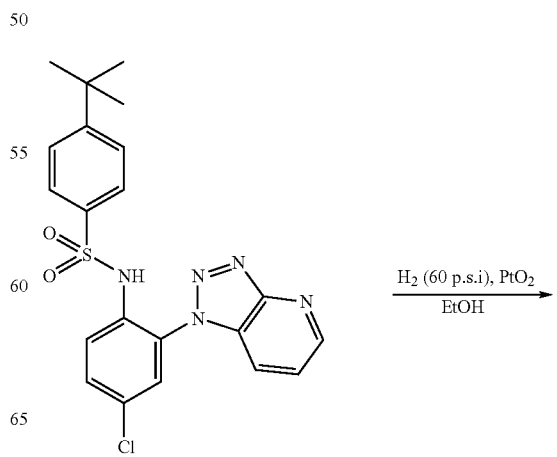

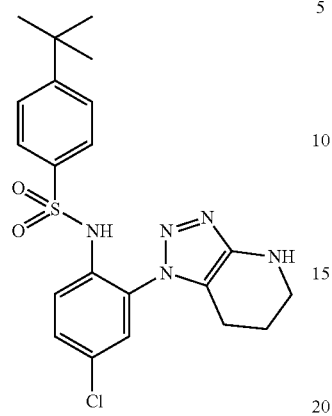

A 250 mL pressure vessel was charged with 4-tert-butyl-N-(4-chloro-2-[1,2,3]triazolo[4,5-b]pyridine-1-yl-phenyl)-benzenesulfonamide (synthesized according to general procedure G, 100 mg, 0.23 mmol), PtO$_2$ (50 mg, 0.22 mmol), and MeOH (20 mL). The pressure vessel was placed under 60 p.s.i. of H$_2$ and agitated for 8 hours. The reaction mixture was subsequently filtered through celite, concentrated in vacuo, and purified by preparative TLC to afford 4-tert-butyl-N-[4-chloro-2-(4,5,6,7-tetrahydro-[1,2,3]triazolo[4,5-b]pyridin-1-yl)-phenyl]-benzenesulfonamide: MS (ES) M+H expected 446.1, found 446.1.

General Procedure N

Example 4-tert-Butyl-N-[4-chloro-2-(4-methyl-4,5,6,7-tetrahydro-[1,2,3]triazolo[4,5-b]pyridin-1-yl)-phenyl]-benzenesulfonamide

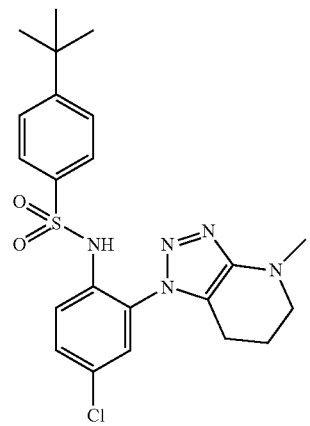

A 4 mL scintillation vial was charged with 4-tert-butyl-N-[4-chloro-2-(4,5,6,7-tetrahydro-[1,2,3]triazolo[4,5-b]pyridin-1-yl)-phenyl]-benzenesulfonamide (synthesized according to general procedure M, 11 mg, 0.025 mmol), H$_2$CO (37% in H$_2$O, 3 mg, 0.037 mmol), and HCO$_2$H (100 μL). The vial was sealed and heated to 100° C. for 1 hour. The solvent was subsequently removed in vacuo and the residue purified by preparative TLC to afford 4-tert-butyl-N-[4-chloro-2-(4-methyl-4,5,6,7-tetrahydro-[1,2,3]triazolo[4,5-b]pyridin-1-yl)-phenyl]-benzenesulfonamide: MS (ES) M+H expected 460.2, found 460.0.

General Procedure O

Example 4-tert-Butyl-N-[4-chloro-2-(4-methanesulfonyl-4,5,6,7-tetrahydro-[1,2,3]triazolo[4,5-b]pyridin-1-yl)-phenyl]-benzenesulfonamide

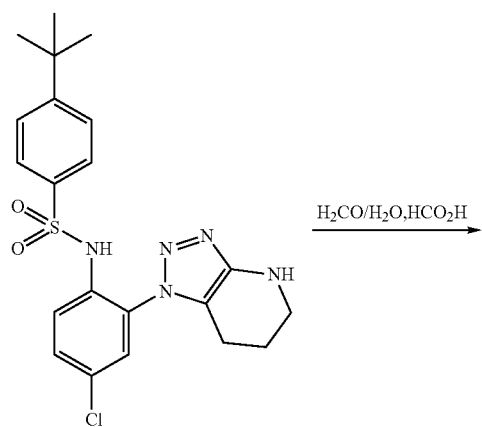

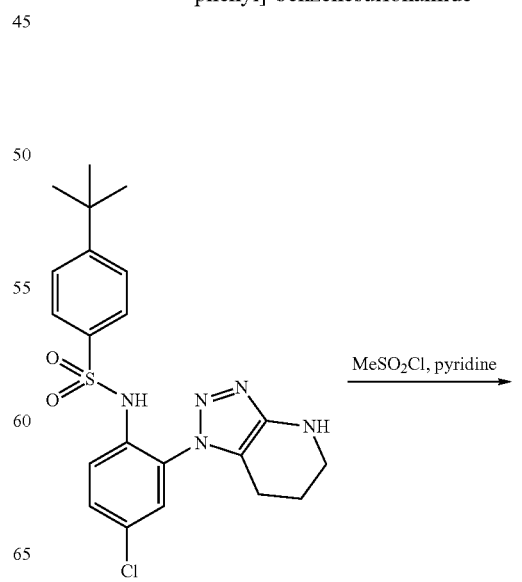

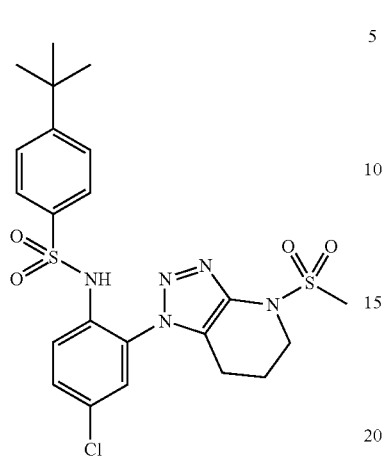

A 4 mL scintillation vial was charged with 4-tert-butyl-N-[4-chloro-2-(4,5,6,7-tetrahydro-[1,2,3]triazolo[4,5-b]pyridin-1-yl)-phenyl]-benzenesulfonamide (synthesized according to general procedure M, 13 mg, 0.029 mmol), MeSO$_2$Cl (5 mg, 0.04 mmol), and pyridine (500 μL). The reaction was stirred for 1 hour. The solvent was subsequently removed in vacuo and the residue purified by preparative TLC to afford 4-tert-butyl-N-[4-chloro-2-(4-methanesulfonyl-4,5,6,7-tetrahydro-[1,2,3]triazolo[4,5-b]pyridin-1-yl)-phenyl]-benzenesulfonamide: MS (ES) M+H expected 524.1, found 524.0.

General Procedure P

Example 4-tert-Butyl-N-[4-chloro-2-(5-isopropyl-[1,2,3]triazol-1-yl)-phenyl]-benzenesulfonamide

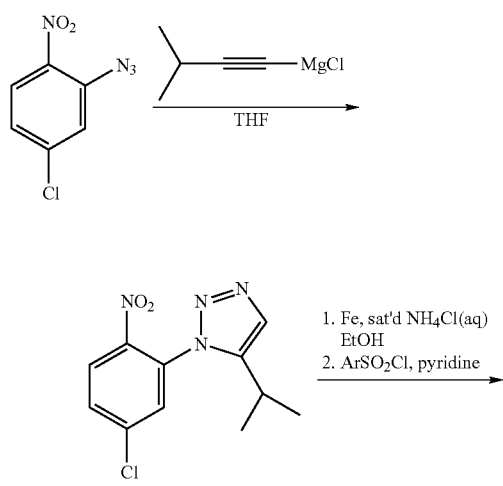

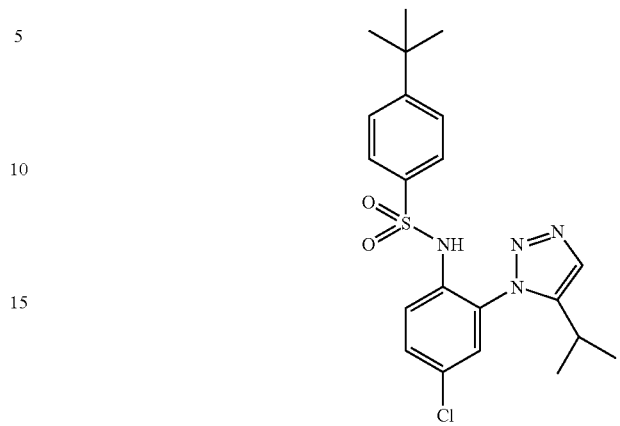

Step 1: A 30 mL scintillation vial was charged with 2-azido-4-chloro-1-nitrobenzene (200 mg, 1.0 mmol) and 0.75 M 3-methyl-1-butynylmagnesium chloride in THF (1.6 mL, 1.2 mmol; prepared by mixing 3-methyl-1-butyne (120 μL, 1.2 mmol) and iPrMgCl (1.5 mL, 1.0 M in THF) at room temperature, heating to 40° C. for 30 minutes then cooling to room temperature). The reaction was allowed to stir at room temperature for 1 hour after which the reaction was quenched with SiO$_2$ and the solvent removed. The product (adsorbed to SiO$_2$) was then loaded on a SiO$_2$ column and purified to give 1-(5-chloro-2-nitro-phenyl)-5-isopropyl-1H-[1,2,3]triazole.

Step 2: The product was then reduced (according to general procedure F, step 2) and sulfonylated (according to general procedure G) to afford 4-tert-butyl-N-[4-chloro-2-(5-isopropyl-[1,2,3]triazol-1-yl)-phenyl]-benzenesulfonamide: MS (ES) M+H expected 433.2, found 433.1.

General Procedure Q

Example 4-tert-Butyl-N-[4-chloro-2-(5-dimethylaminomethyl-[1,2,3]triazol-1-yl)-phenyl]-benzenesulfonamide

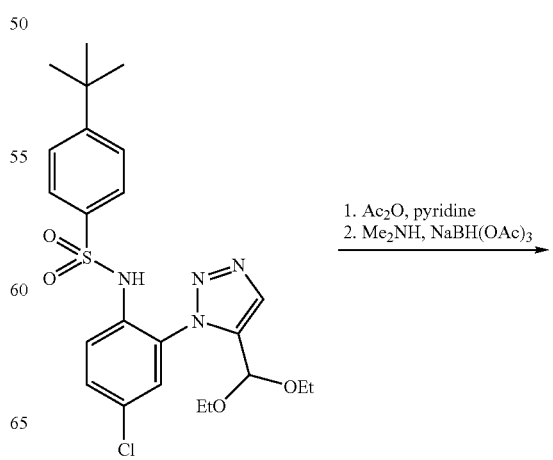

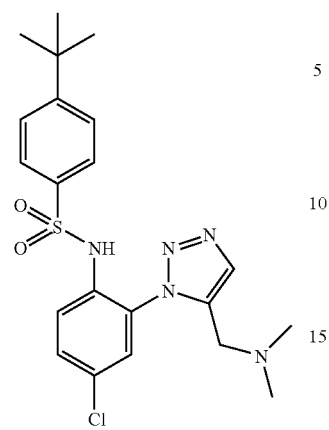

A 30 mL scintillation vial was charged with 4-tert-butyl-N-[4-chloro-2-(5-diethoxymethyl-[1,2,3]triazol-1-yl)-phenyl]-benzenesulfonamide (synthesized according to general procedure Q, 1.0 g, 2.0 mmol) and Ac$_2$O/pyridine (1:2 v/v, 6 mL), and stirred at room temperature for 4 hours. The reaction mixture was subsequently diluted with Et$_2$O and washed with 1 M HCl, saturated NaHCO$_3$, and brine. The combined organics were then dried over Na$_2$SO$_4$ and concentrated in vacuo. The resultant product (35 mg, 0.075 mmol) and dimethyl amine (80 μL, 2.0 M in THF) were combined in a 4 mL scintillation vial and stirred for 30 minutes. NaBH(OAc)$_3$ (32 mg, 0.17 mmol) was then added and the reaction was stirred for 12 hours at room temperature. The reaction mixture was subsequently diluted with Et$_2$O, washed with 1 M HCl, and the combined organics were purified by preparative TLC to generate 4-tert-butyl-N-[4-chloro-2-(5-dimethylaminomethyl-[1,2,3]triazol-1-yl)-phenyl]-benzenesulfonamide: MS (ES) M+H expected 448.2, found 448.4.

General Procedure R

Example

N-(4-Chloro-2-[1,2,3]triazolo[4,5-b]pyridin-1-yl-phenyl)-3-fluoro-4-morpholin-4-yl-benzenesulfonamide

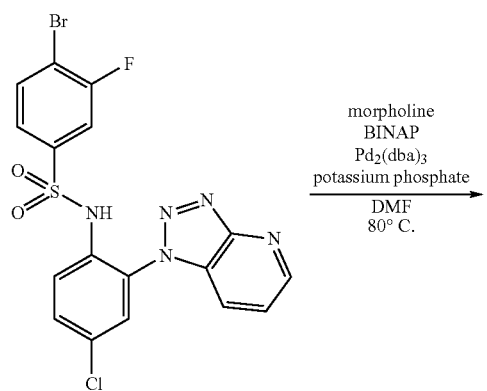

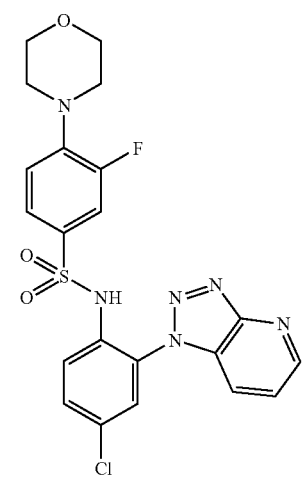

4-Bromo-N-(4-chloro-2-[1,2,3]triazolo[4,5-b]pyridin-1-yl-phenyl)-3-fluoro-benzensulfonamide (synthesized according to general procedure G, 180 mg, 0.37 mmol) was dissolved in 3 ml of anhydrous dimethylformamide under an atmosphere of nitrogen. To this mixture was added morpholine (161 mg, 1.85 mmol), 2,2'-bis(diphenylphosphine)-1,1'-binaphthyl (BINAP) (34 mg, 0.055 mmol), potassium phosphate tribasic monohydrate (511 mg, 2.22 mmol), and tris (dibenzylideneacetone) dipalladium(0) (Pd$_2$(dba)$_3$) and the resultant mixture was heated at 80° C. overnight. The following day, the reaction mixture was partitioned with a saturated solution of sodium bicarbonate and dichloromethane and the aqueous layer was extracted three times with dichloromethane. The combined organics were subsequently dried over magnesium sulfate, concentrated in vacuo, and purified by reverse phase HPLC, followed by silica gel chromatography employing ethyl acetate:hexanes (1:1), to afford 80 mg of the desired product as a white powder: MS (ES) M+H expected 489.1, found 489.0.

General Procedure S

Example 4-tert-Butyl-N-{4-chloro-2-[4-(1-hydroxy-1-methyl-ethyl)-pyrazol-1-yl]-phenyl}-benzenesulfonamide

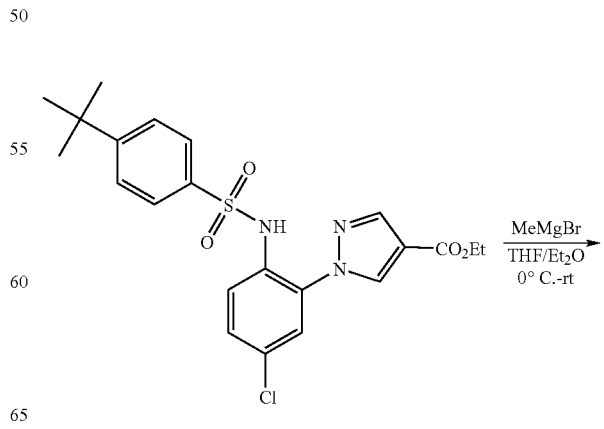

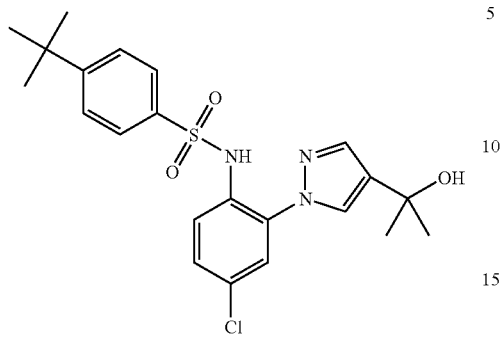

A 4 mL scintillation vial was charged with 1-[2-(4-tert-butyl-benzenesulfonylamino)-5-chloro-phenyl]-1H-pyrazole-4-carboxylic acid ethyl ester (synthesized from general procedure D, 100 mg, 0.22 mmol) in 0.5 mL of anhydrous THF and cooled to 0° C. under a nitrogen atmosphere. To this solution was added of methyl magnesium bromide (0.36 mL, 3.0 M in Et$_2$O) and the reaction was allowed to slowly warm to ambient temperature. Upon complete consumption of the starting material (via LCMS), the reaction was quenched by the addition of an NH$_4$Cl solution. The solvent was subsequently removed in vacuo and the residue was purified via preparative HPLC to afford 4-tert-butyl-N-{4-chloro-2-[4-(1-hydroxy-1-methyl-ethyl)-pyrazol-1-yl]-phenyl}-benzenesulfonamide as a white powder: MS (ES) M+H expected 448.1, found 448.1.

General Procedure T

Example 4-tert-Butyl-N-[4-chloro-2-(1H-pyrazolo[3,4-b]pyridin-3-yl)-phenyl]-benzenesulfonamide

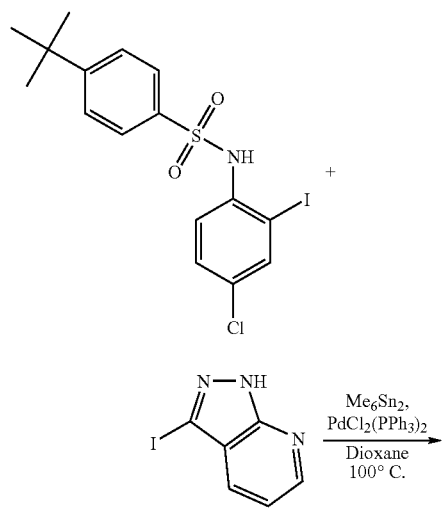

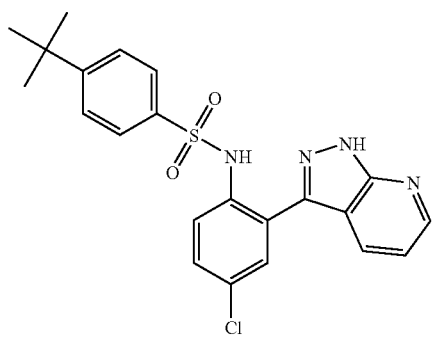

4-tert-butyl-N-(4-chloro-2-iodo-phenyl)-benzenesulfonamide (100 mg, 0.22 mmol), 3-iodo-1H-pyrazolo[3,4-b]pyridine (71 mg, 0.29 mmol), bis(triphenylphosphine)Pd(II)dichloride (20 mg, 0.03 mmol), and hexamethylditin (70 μL, 0.33 mmol) were suspended in 0.7 mL of dioxane and heated to 100° C. for 24 hours in a sealed 4 mL scintillation vial. The black crude residue obtained was purified by preparative TLC to afford 4-tert-butyl-N-[4-chloro-2-(1H-pyrazolo[3,4-b]pyridin-3-yl)-phenyl]-benzenesulfonamide: MS (ES) M+H expected 441.1, found 441.0.

General Procedure U

Example

N-(2-Boranyl-4-chloro-phenyl)-4-tert-butyl-benzenesulfonamide

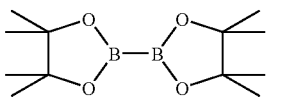

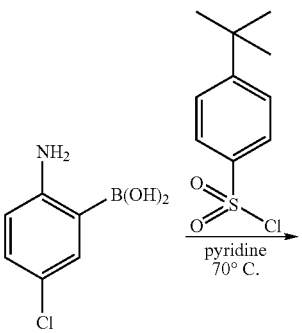

-continued

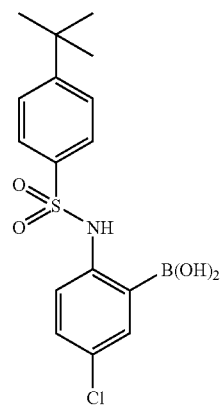

Step 1: A 100 mL round bottom flask was charged with 2-bromo-4-chloroaniline (20.6 g, 100 mmol), tricyclohexylphosphine (Cy₃P)(0.73 g, 2.02 mmol), palladium acetate (0.115 g, 0.505 mmol), 4,4,5,5,4',4',5',5'-Octamethyl-[2,2']bi[[1,3,2]dioxaborolanyl] (25.4 g, 100 mmol), triethylamine (1.22 g, 120 mmol), dioxane (200 mL). The reaction was stirred at 85° C. for 18 hours under nitrogen. The reaction mixture was quenched by adding 200 mL of water and then extracted with ethyl acetate (100 mL, 3 times). The organic layers were combined and dried over Na₂SO₄ overnight. Solid was filtered off and the filtrate was concentrated to dryness. The crude product was purified by flash chromotagraph to yield 13.2 g of product as colorless solid. MS (ES) M+H expected 140.1, found 140.1.

Step 2: A 100 mL round-bottom flask was charged with 2-boranyl-4-chloro-phenylamine (1.1 g, 7.9 mmol) and 4-tert-butyl benzenesulfonyl chloride (2.7 g, 11.6 mmol). The flask was evacuated and purged with nitrogen, followed by the addition of pyridine (20 mL). The homogeneous light purple solution was stirred 4 hours, and then poured onto a rapidly stirring cold slurry of 6 M HCl (66 mL) (formed by placing the acidic solution in acetonic dry ice). The resultant precipitated sulfonamide was filtered, washed thoroughly with 10% HCl, and dried in vacuo to afford purplish solid. The crude product was purified by flash chromatograph to yield 1.3 g of product as colorless solid: MS (ES) M+H expected 336.5, found 336.5.

General Procedure V

Example 4-tert-Butyl-N-[4-chloro-2-(1H-indazol-3-yl)-phenyl]-benzenesulfonamide

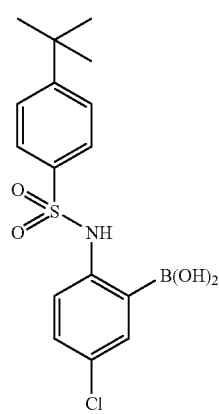

-continued

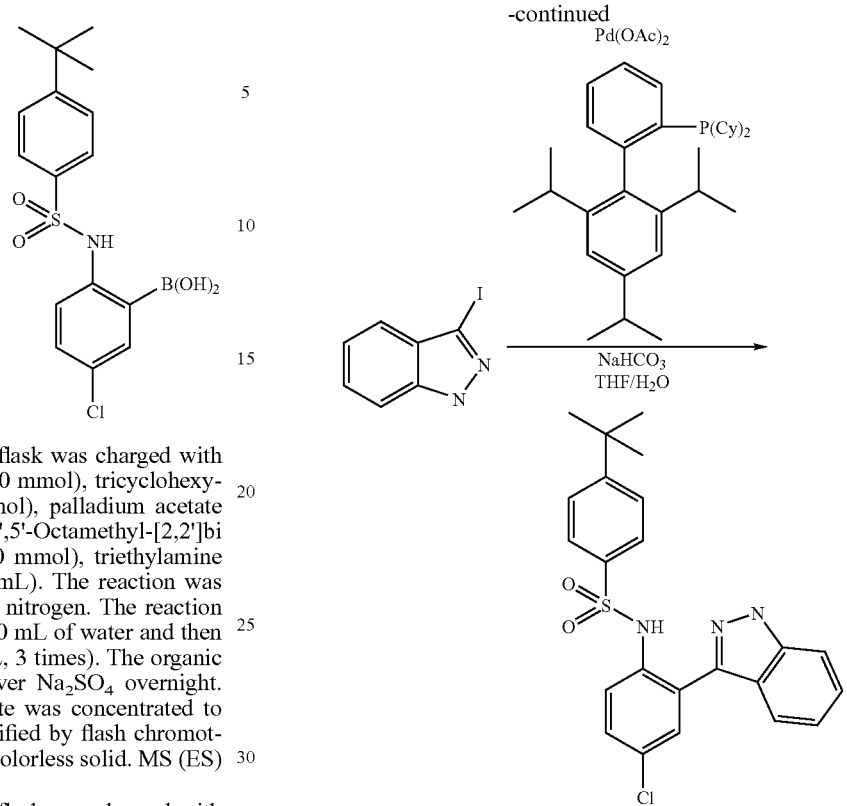

A 25 mL scintillation vial was charged with N-(2-boranyl-4-chloro-phenyl)-4-tert-butyl-benzenesulfonamide (90 mg, 0.27 mmol), tris(dibenzylideneacetone)dipalladium (18 mg, 0.02 mmol), 2-dicyclohexylphosphino-2', 4', 6'-triisopropylbiphenyl (24 mg, 0.05 mmol), 3-iodo-1H-indazole (65 mg, 0.27 mmol), saturated aqueous sodium bicarbonate (1 mL), and tetrahydrofuran (1.5 mL). The reaction was stirred at 80° C. under nitrogen overnight. The following day, the reaction was cooled to room temperature and diluted with 10 mL of ethyl acetate. The solution was subsequently washed with saturated aqueous NaHCO₃ and brine, and then concentrated to dryness. The crude product was purified by flash chromatograph to yield 23 mg of product: MS (ES) M+H expected 441.1, found 441.1.

General Procedure W

Example

N-(4-Chloro-2-[1,2,3]triazolo[4,5-b]pyridin-1-yl-phenyl)-4-{1-[(E)-hydroxyimino]-ethyl}benzenesulfonamide

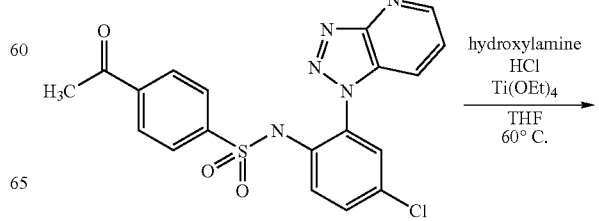

-continued

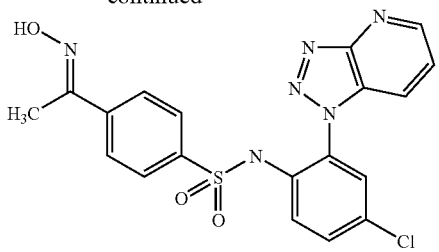

A 4 mL vial was charged with 4-acetyl-N-(4-chloro-2-[1,2,3]triazolo[4,5-b]pyridin-1-yl-phenyl)-benzenesulfonamide (synthesized according to general procedures F and G, 100 mg, 0.23 mmol), hydroxylamine hydrochloride (49 mg, 0.70 mmol), and 2 mL THF. The resultant slurry was mixed well, then titanium ethoxide (98 µL, 47 mmol) was added and the mixture heated to 60° C. overnight. The reaction mixture was subsequently diluted with ~2 mL of acetonitrile/H$_2$O and purified by reversed phase HPLC to afford N-(4-chloro-2-[1,2,3]triazolo[4,5-b]pyridin-1-yl-phenyl)-4-{1-[(E)-hydroxyimino]-ethyl}benzenesulfonamide: MS (ES) M+H expected 443.0, found 443.0.

General Procedure X

Example 4-(1-Amino-ethyl)-N-(4-chloro-2-[1,2,3]triazolo[4,5-b]pyridin-1-yl-phenyl)-benzenesulfonamide

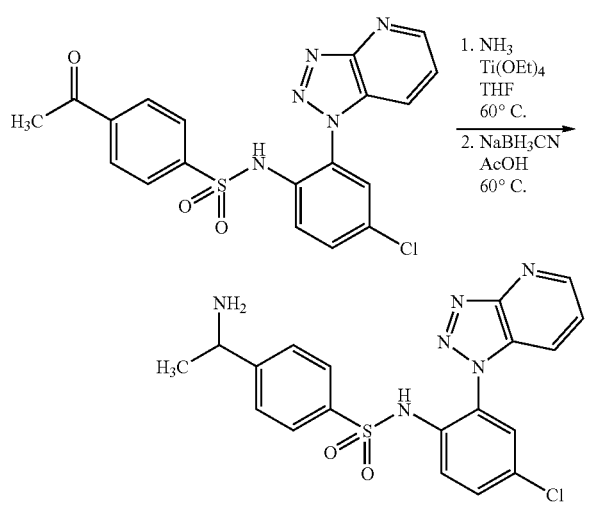

A 4 mL vial was charged with 4-acetyl-N-(4-chloro-2-,[1,2,3]triazolo[4,5-b]pyridin-1-yl-phenyl)-benzenesulfonamide (synthesize according to general procedures F and G, 100 mg, 0.23 mmol), 7 M NH$_3$ in MeOH (100 µL, 0.70 mmol, and 2 mL THF. The resulting slurry was stirred well, the titanium ethoxide (98 µL, 47 mmol) was added and the mixture heated to 60°C. for three hours. Sodium cyanoborohydride (22 mg, 0.35 mmol) and acetic acid (5 drops) were then added and the mixture was maintained at 60 ° C. overnight. The reaction mixture was diluted with ~2 mL of acetonitrile/H$_2$0 and purified by reversed phase HPLC to afford 4-(1-amino-ethyl)-N-(4-chloro-2-[1,2,3] triazolo[4,5-]pyridin-1-phenyl)-benzensulfonamide: MS (ES) M+H expected 428.0, found 428.0

General Procedure Y

Example

N-(4-Chloro-2 [1,2,3]trazolo[4,5-b]pyridin-1-yl-phenyl)-4-(1-hydroxy -1-methyl-ethyl)-benzenesulfonamide

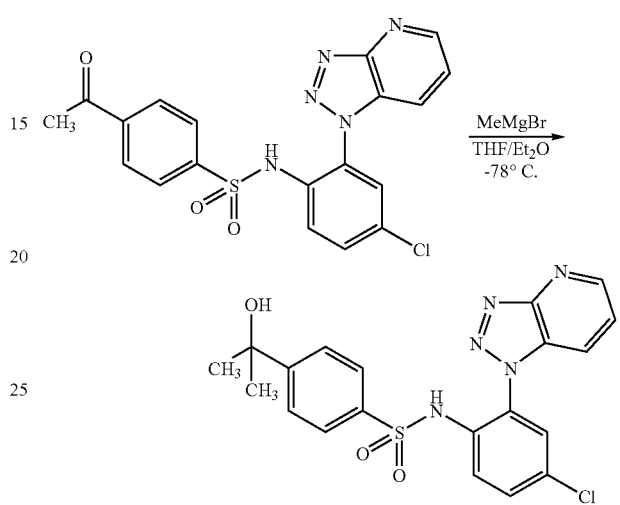

Step 1: 4-Chloro-2-fluoro-1-nitrobenzene (25 g, 142 mmol) and 1H-[1,2,3]triazolo[4,5-b]pyridine (18.8 g, 157 mmol) were slurried in DMF (50 mL) in a 200 mL round-bottom flask fitted with a magnetic stir bar. Potassium carbonate (29.5 g, 214 mmol) was added to the mixture and it was then heates while stirring in a 60°C. oil bath under N$_2$. LCMS analysis after two hours indicated complete consumption of the nitrobenzene and two different isomeric forms of the desired product. Water (250 mL) was subsequently added in a steady stream to the rapidly stirring mixture to precipitate the crude product. The resultant precipitate was collected by vacuum filtration and washed twice with 100 mL water. The resultant damp filter was slurried with 50 mL toluene and the solids collected by vacuum filtration. This action was repeated three additional times and then the resultant solid was dried in vacuo to afford 21.6 g (55% yield) 1-(5-chloro-2-nitrophenyl)-1 H-[1,2,3]triazolo[4,5-b]pyridine as an off-white solid.

Step 2: 1-(5-Chloro-2-nitrophenyl)-1H-[1,2,3]triazolo[4,5-b]pyridine (10 g, 36.3 mmol) was dissolved in 200 mL concentrated HCl in a 1 L round-bottom flask fitted with a magnetic stir bar. Iron powder (4.2 g, 74.4 mmol) was added in portions to the rapidly stirring solution. The resultant thick yellow slurry was allowed to stir overnight until no visible metallic iron was observed in the reaction vessel. The following day, LCMS analysis indicated complete reduction to the aniline. The mixture was subsequently transferred to a 500 mL Buchner funnel, with the assistance of a small amount of concentrated HCl to rinse out the remaining slurry from the reaction vessel, and the insoluble material was collected by vacuum filtration. The filter cake was then stirred into a thick paste with water (15 mL) and the solids collected by vacuum filtration. The material was again stirred in 15 mL water and filtered, the mother liquors were discarded, and the solid material dried in vacuo. The resultant light brown solid was slurried in 50 mL of 1:1 (v/v) EtOAc:acetonitrile and heated to the boiling point with a heat gun. The mixture was allowed to cool to room temperature and the solids were collected by vacuum filtration. The solids were subsequently washed with a small amount of 1:1 EtOAc:acetonitrile and dried in vacuo to generate 7.5 g 4-chloro-2-[1,2,3]triazolo[4,5-b]pyridin-1-yl-phenylamine (light grey solid, 84% yield).

Step 3: To 4-chloro-2-[1,2,3]triazolo[4,5-b]pyridin-1-yl-phenylamine (33.9 g, 138.0 mmol) was added pyridine (170 mL), followed by 4-acetylbenzenesulfonyl chloride (45.3 g, 207 mmol) at room temperature. Upon stirring for 10 minutes, the flask was cooled to 0° C. and $CH_3SO_2Cl$ (8.0 mL, 103.5 mmol) was added dropwise under a nitrogen atmosphere. The resultant reaction mixture was allowed to warm to room temperature over 8 hours with stirring. 5 N NaOH (200 mL) was subsequently added to the reaction mixture and stirred at 75° C. for 12 hours to hydrolyze the bis-sulfonamide. The hot reaction mixture was then slowly poured into 2 N HCl (500 mL) with efficient stirring. The solution was stirred for 15 minutes and the precipitated solid was isolated via filtration through a sintered-glass funnel. The solid was then washed with water (1000 mL) and heptanes (1000 mL), and then dried at 75° C. in a vacuum oven for 12 hours to provide the desired sulfonamide as yellow solid (56.5 g) in 96% yield.

A 1-L round-bottom flask was charged with the resultant ketone (54.2 g, 127 mmol). The solid was then dissolved in 500 mL anhydrous THF (tetrahydrofuran) and the solution was cooled to −40° C. To the rapidly stirring solution was added 3.0 M MeMgBr (169 mL, 508 mmol) and the reaction was warmed to −20° C. and stirred for 2 hours. Upon consumption of starting material, the reaction was quenched with acetone (40 mL) at −20° C. and then warmed to ambient temperature. An additional 100 mL water was added to the reaction and it was concentrated to a primarily aqueous heterogeneous syrup. The syrup was subsequently poured onto 500 mL 1 N HCl and stirred for 1 hour at room temperature. The resultant precipitate was filtered and the solid was washed with water (1 L) and heptanes (750 mL), and then dried at 70° C. overnight in a vacuum oven to provide 54.5 g of the crude product as a light brown solid. The solid was subsequently dissolved in 1.3 L 85% MeCN/water at reflux and the solution then cooled to ambient temperature. To the resultant solution was added activated charcoal (28 g) and the solution was stirred 5 minutes. The heterogeneous suspension was then filtered through CELITE®, the filter cake washed thoroughly with MeCN, and the filtrate concentrated in vacuo to afford 46.3 g of a slightly yellowish solid. The resultant solid was dissolved in refluxing 85% MeCN/water (712 mL), filtered (while hot) to remove a minimal quantity of insoluble material, and then cooled slowly to room temperature to enable crystallization to proceed. The flask was allowed to sit 4 hours at ambient temperature and then stored overnight in a refrigerator. The following day, the solid was collected via filtration and then washed with MeCN. Finally, the solid was dried at 70° C. overnight in a vacuum oven to afford the desired dimethyl carbinol as a white solid (42.8 g, 76%): MS (ES) M+Na expected 466.0, found 466.0.

General Procedure Z

Example

N-(4-Chloro-2-[1,2,3]triazolo[4,5-b]pyridin-1-yl-phenyl)-4-(2-hydroxy-1,1-dimethyl-ethyl)-benzene-sulfonamide

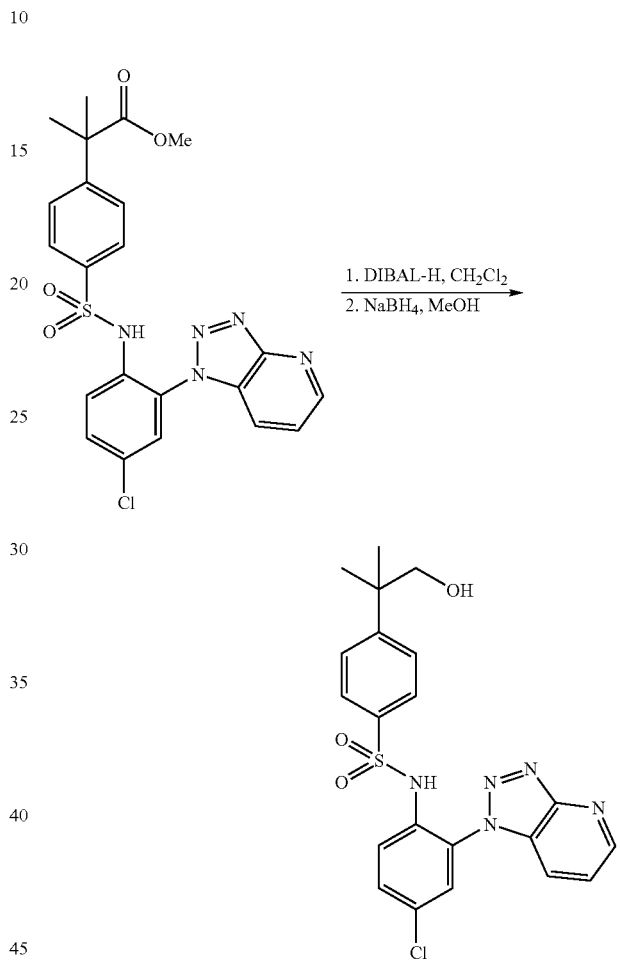

DIBAL-H (diisobutylaluminium hydride)(0.71 mL, 1.0 M solution in $CH_2Cl_2$) was added to 2-[4-(4-chloro-2-[1,2,3]triazolo[4,5-b]pyridin-1-yl-phenylsulfamoyl)-phenyl]-2-methyl-propionic acid methyl ester (synthesized according to general procedures F and G, 137 mg, 0.282 mmol) in $CH_2Cl_2$ (3 mL) at −78° C. After 1 hour, LCMS indicated a 2:1 ratio of the desired product and corresponding aldehyde intermediate. 1 N HCl (2 mL) was added to the reaction mixture, the flask was warmed to room temperature, and the solution was diluted with EtOAc (30 mL). The EtOAc layer was separated, dried ($Na_2SO_4$), and evaporated in vacuo. The resultant crude residue was treated with $NaBH_4$ (30 mg, excess) in MeOH (3 mL) at room temperature for 10 minutes and directly purified by preparative HPLC to afford the title compound as a white powder: MS (ES) M+H expected 458.1, found 458.0.

General Procedure AA

Example

N-(4-Chloro-2-[1,2,3]triazolo[4,5-b]pyridin-1-yl-phenyl)-4-(1-hydroxy-ethyl)-benzenesulfonamide

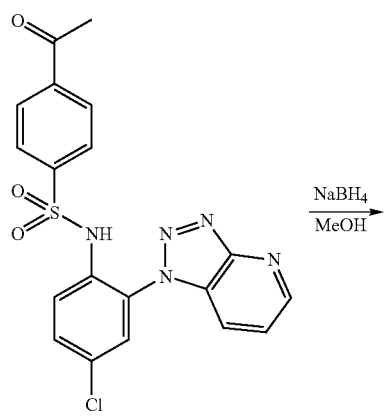

General Procedure BB

Example

N-(4-Chloro-2-[1,2,3]triazolo[4,5-b]pyridin-1-yl-phenyl)-4-(2,2,2-trifluoro-1-hydroxy-1-methyl-ethyl)-benzenesulfonamide

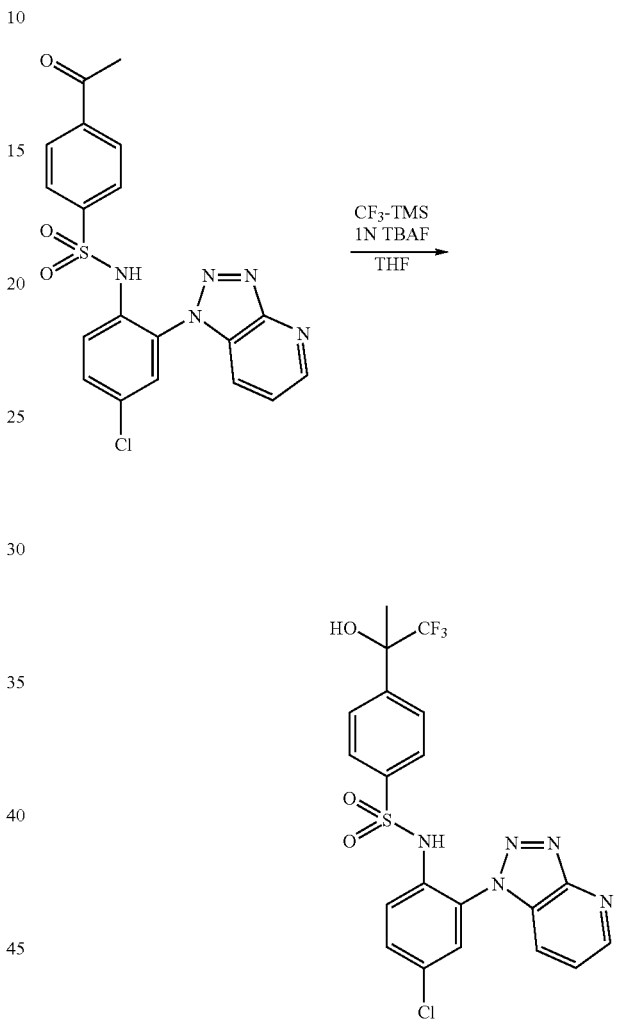

To 4-acetyl-N-(4-chloro-2-[1,2,3]triazolo[4,5-b]pyridin-1-yl-phenyl)-benzene-sulfonamide (synthesized according to general procedures F and G, 500 mg, 1.17 mmol) in MeOH (5 mL) was added NaBH$_4$ (144 mg, 3.81 mmol) at 0° C. and the mixture was stirred for one hour at room temperature. The reaction mixture was then diluted with EtOAc (50 mL) and the organics were washed with saturated aqueous NH$_4$Cl (50 mL), water (50 mL), and brine (50 mL). The organics were subsequently dried (Na$_2$SO$_4$), concentrated in vacuo, and purified by automated flash chromatography to obtain the title compound as foamy white solid (424 mg) in 84% yield: MS (ES) M+H expected 430.1, found 430.1.

To 4-acetyl-N-(4-chloro-2-[1,2,3]triazolo[4,5-b]pyridin-1-yl-phenyl)-benzene-sulfonamide (synthesized according to general procedures F and G, 500 mg, 1.17 mmol) was added CF$_3$-TMS (trifluoromethyl-trimethylsilane) (4.7 mL, 0.5 M solution in THF), followed by TBAF (tetra-n-butylammonium fluoride) (2.34 mL, 1.0 M solution in THF) at 0° C., and the solution was stirred at room temperature for 16 hours. Both TLC and LCMS analysis indicated ~10-15% completion of reaction. The reaction mixture was diluted with EtOAc (50 mL) and the organics were washed with washed with 2 N HCl (2×25 mL), water (25 mL), and brine (25 mL). The organics were subsequently dried (Na$_2$SO$_4$), concentrated in vacuo, and purified by automated flash chromatography followed by preparative HPLC to afford the title compound as a white powder: MS (ES) M+H expected 498.1, found 498.0.

General Procedure CC

Example 4-tert-Butyl-N-(4-chloro-2-(5-methyl-1H-1,2,3-triazol-1-yl)phenyl)benzenesulfonamide

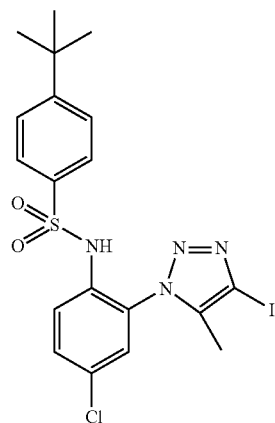

1. PhMgBr
   THF
   −78° C.
2. nBuLi
3. acetone
   −78° C.-ambient temperature

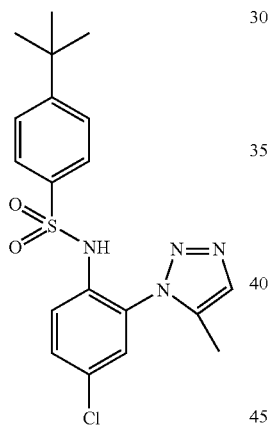

4-tert-butyl-N-(4-chloro-2-(4-iodo-5-methyl 1H-1,2,3-triazol-1-yl)phenyl)benzenesulfonamide (synthesized according to general procedure P, 75 mg, 0.14 mmol) was placed in a 10 mL 2-neck flask and the flask was evacuated and purged with $N_2$ three times. To the solid was added THF (0.71 mL) and the solution was lowered to −78° C. PhMgBr (0.079 mL, 1.8 M) was added to the solution and it was stirred for 15 minutes. n-BuLi (0.069 mL, 2.0 M) was subsequently added and the reaction was stirred an additional 60 minutes. Acetone (0.042 mL, 0.57 mmol) was added to the reaction and it was warmed to ambient temperature. The solution was subsequently partitioned with EtOAc/10% HCl and the aqueous layer was extracted three times with EtOac. The combined organics were dried over sodium sulfate, concentrated in vacuo, and purified by HPLC to afford the desired triazole: MS (ES) M+H expected 405.1, found 405.4.

General Procedure DD

Example 4-tert-Butyl-N-(4-chloro-2-(4-(1-hydroxyethyl)-5-methyl-1H-1,2,3-triazol-1-yl)phenyl)benzenesulfonamide

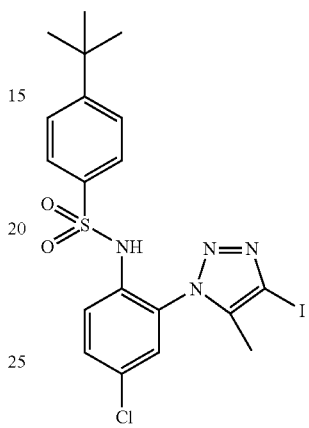

1. PhMgBr
   THF
   −78° C.
2. nBuLi
3. HCOMe
   −78° C.-0° C.

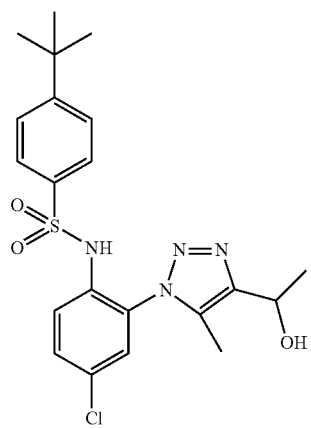

4-tert-butyl-N-(4-chloro-2-(4-iodo-5-methyl 1H-1,2,3-triazol-1-yl)phenyl)benzenesulfonamide (synthesized according to general procedure P, 200 mg, 0.38 mmol) was placed in a 10 mL 2-neck flask and the flask was evacuated and purged with $N_2$ three times. To the solid was added THF (1.9 mL) and the solution was lowered to −78° C. PhMgBr (0.21 mL, 1.8 M) was added to the solution and it was stirred for 15 minutes. n-BuLi (0.19 mL, 2.0 M) was subsequently added and the reaction was stirred an additional 30 minutes. Acetaldehyde (0.085 mL, 1.5 mmol) was added to the reaction and it was warmed to 0° C. The solution was subsequently quenched with 10% HCl and the aqueous layer was extracted three times with EtOac. The combined organics were dried over sodium sulfate, concentrated in vacuo, and purified by HPLC to afford 4-tert-butyl-N-(4-chloro-2-(4-(1-hydroxyethyl)-5-methyl-1H-1,2,3-triazol-1-yl)phenyl)benzenesulfonamide as a white solid: MS (ES) M+H expected 449.1, found 449.1.

General Procedure EE

Example 4-tert-Butyl-N-(4-chloro-2-(4-ethynyl-5-methyl-1H-1,2,3-triazol-1-yl)phenyl)benzenesulfonamide

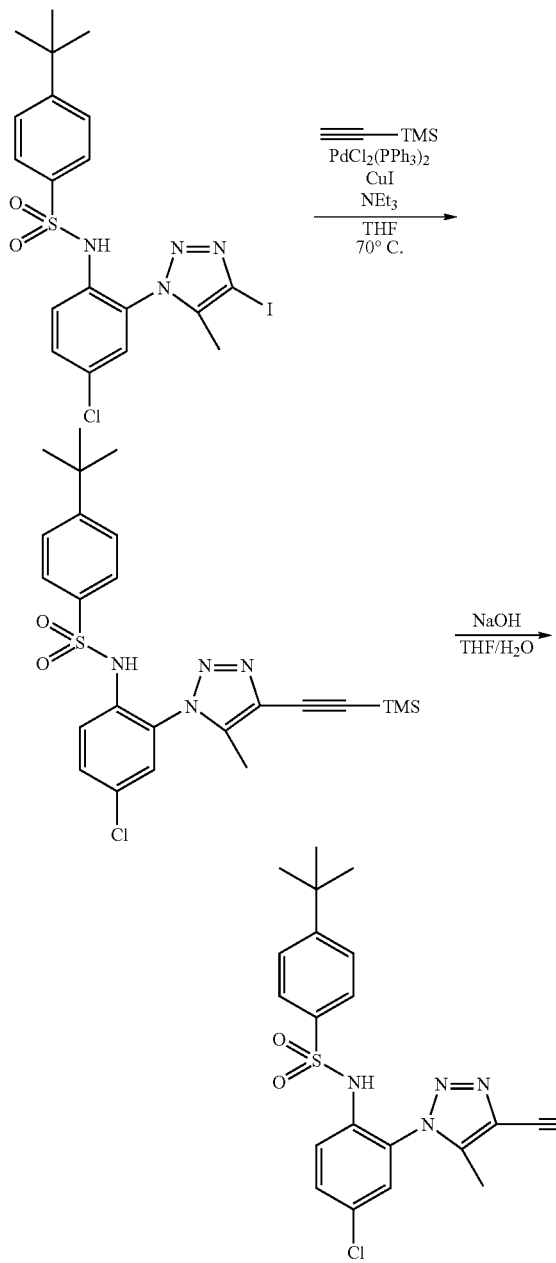

Step 1: A 1-dram vial was charged with 4-tert-butyl-N-(4-chloro-2-(4-iodo-5-methyl 1H-1,2,3-triazol-1-yl)phenyl)benzenesulfonamide (synthesized according to general procedure P, 50 mg, 0.094 mmol), TMS acetylene (20 μL, 0.14 mmol), bis(triphenylphosphine) palladium (II) dichloride (catalytic quantity), CuI (catalytic quantity), triethylamine (26 μL, 0.19 mmol), and THF (0.5 mL). The suspension was heated to 70° C. and stirred 3 hours. The crude reaction was subsequently dry loaded onto silica gel and purified by column chromatography to afford the desired acetylene.

Step 2: To the above TMS-protected acetylene (20 mg, 0.40 mmol) in THF (0.2 mL) was added aqueous NaOH (0.1 mL, 3 M). The solution was subsequently heated to 60° C. and stirred for 3 hours. The crude reaction was concentrated in vacuo, dissolved in a minimal amount of THF, and purified by preparative TLC to produce 4-tert-butyl-N-(4-chloro-2-(4-ethynyl-5-methyl-1H-1,2,3-triazol-1-yl)phenyl)benzenesulfonamide: MS (ES) M+H expected 429.1, found 429.3.

General Procedure FF

Example 4-tert-Butyl-N-(4-chloro-2-(4-ethyl-5-methyl-1H-1,2,3-triazol-1-yl)phenyl)benzenesulfonamide

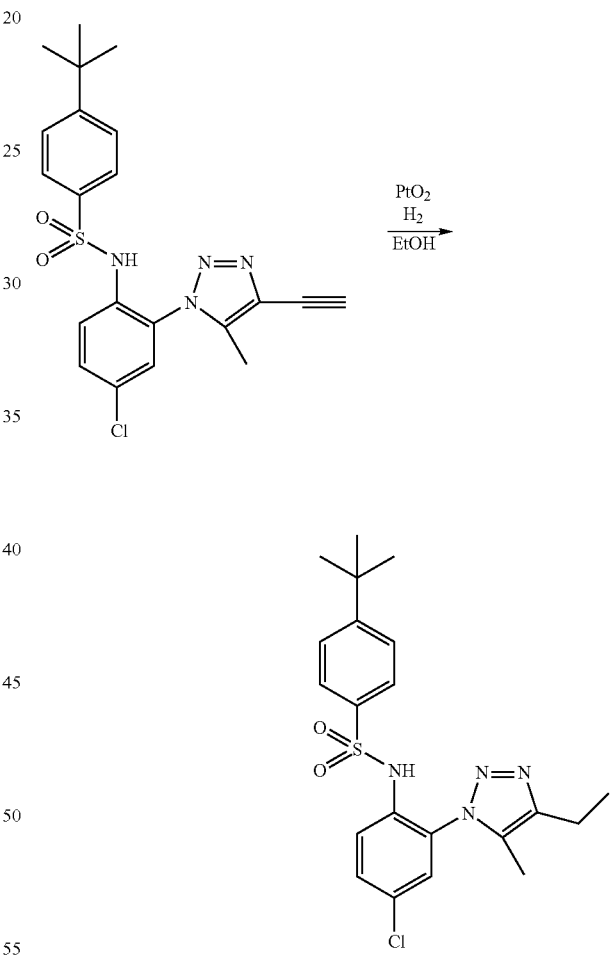

A pressure vessel was charged with 4-tert-butyl-N-(4-chloro-2-(4-ethynyl-5-methyl-1H-1,2,3-triazol-1-yl)phenyl)benzenesulfonamide (synthesized according to general procedure EE, 15 mg, 0.035 mmol), PtO$_2$ (catalytic quantity), and EtOH (10 mL). The pressure vessel was placed under 70 p.s.i. of H$_2$ and agitated for 2 hours. The reaction mixture was subsequently filtered through celite, concentrated in vacuo, and purified by preparative TLC to afford the desired disubstituted triazole: MS (ES) M+H expected 433.1, found 433.4.

General Procedure GG

Example

Methyl 1-(2-(4-tert-butylphenylsulfonamido)-5-chlorophenyl)-5-methyl-1H-1,2,3-triazole-4-carboxylate

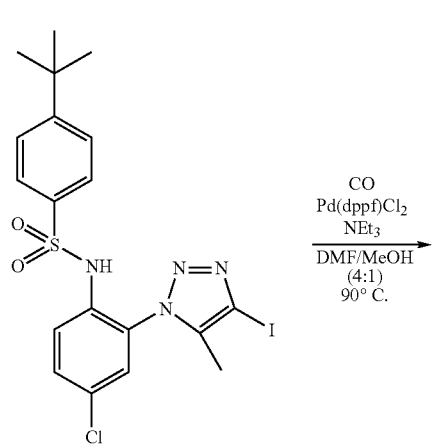

A pressure vessel was charged with 4-tert-butyl-N-(4-chloro-2-(4-iodo-5-methyl 1H-1,2,3-triazol-1-yl)phenyl) benzenesulfonamide (synthesized according to general procedure P, 100 mg, 0.19 mmol), Pd(dppf)Cl$_2$ (8 mg, 0.009 mmol), triethylamine (52 µL, 0.38 mmol), DMF (0.8 mL), and MeOH (0.2 mL). The pressure vessel was placed under 50 p.s.i. of CO at 90° C. and stirred for 10 hours. The reaction mixture was subsequently concentrated in vacuo and purified by column chromatography to afford the desired disubstituted triazole: MS (ES) M+H expected 463.1, found 463.4.

General Procedure HH

Example 4-tert-Butyl-N-(4-chloro-2-(5-methyl-4-((methylamino)methyl)-1H-1,2,3-triazol-1-yl)phenyl)benzenesulfonamide

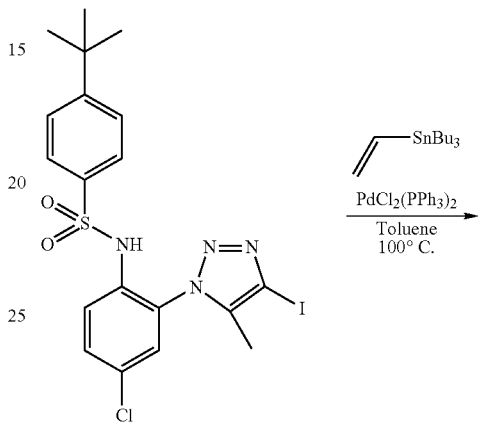

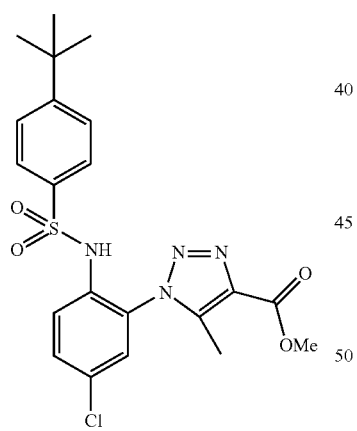

-continued

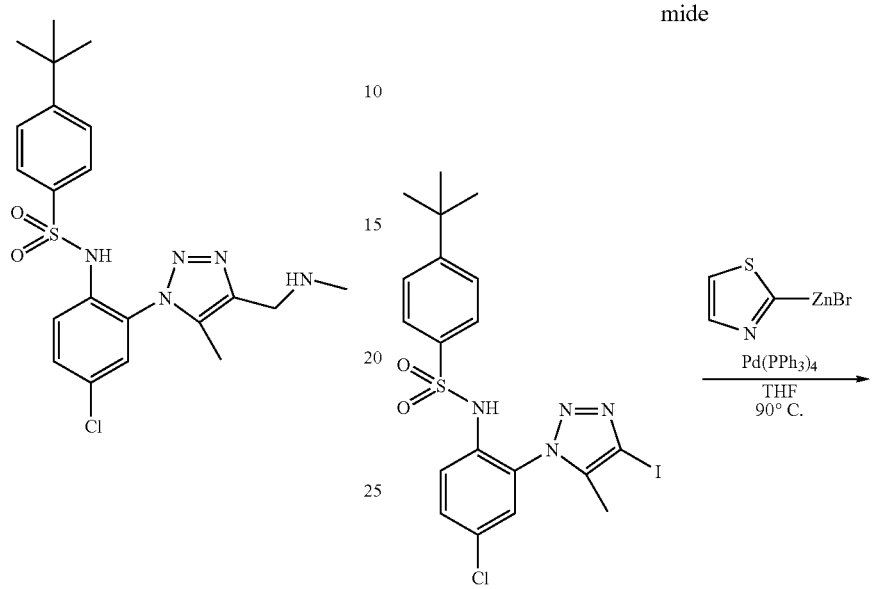

Step 1: A 1-dram vial was charged with 4-tert-butyl-N-(4-chloro-2-(4-iodo-5-methyl 1H-1,2,3-triazol-1-yl)phenyl)benzenesulfonamide (synthesized according to general procedure P, 200 mg, 0.38 mmol), tributyl(vinyl)tin (144 mg, 0.45 mmol), bis(triphenylphosphine) palladium (II) dichloride (catalytic quantity), and toluene (1.5 mL). The suspension was heated to 100° C. and stirred 10 hours. The crude reaction was subsequently concentrated in vacuo and purified by column chromatography to afford the desired vinyl-substituted triazole containing some residual tin by-products.

Step 2: To the above sulfonamide (135 mg, 0.31 mmol) in a 1-dram vial was added osmium tetroxide (64 mg, 2.5% in tBuOH), pyridine (50 µL, 0.62 mmol), and 3 mL of a 3:1 dioxane/water solution. Sodium periodate (268 mg, 1.25 mmol) was slowly added to the mixture and the reaction was stirred at ambient temperature overnight. The following day, the crude reaction was concentrated in vacuo and purified by column chromatography to produce the desired aldehyde.

Step 3: A 1-dram vial was charged with the above aldehyde (10 mg, 0.023 mmol), methylamine (23 µL, 2 M in THF), and methylene chloride (0.3 mL). The solution was stirred 30 minutes at room temperature, followed by the addition of sodium triacetoxyborohydride (10 mg, 0.046 mmol). The resultant mixture was stirred for 10 hours, concentrated in vacuo, and purified by preparative TLC to afford the desired disubstituted triazole: MS (ES) M+H expected 448.2, found 448.4.

General Procedure II

Example 4-tert-Butyl-N-(4-chloro-2-(5-methyl-4-(thiazol-2-yl)-1H-1,2,3-triazol-1-yl)phenyl)benzenesulfonamide

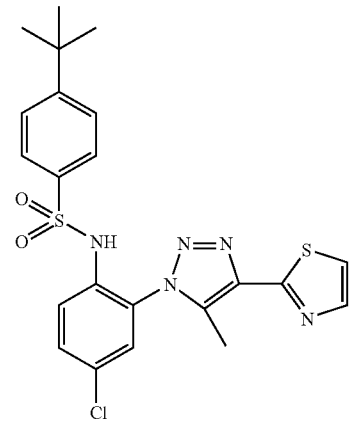

A 1-dram vial was charged with 4-tert-butyl-N-(4-chloro-2-(4-iodo-5-methyl 1H-1,2,3-triazol-1-yl)phenyl)benzenesulfonamide (synthesized according to general procedure P, 250 mg, 0.047 mmol), Pd(PPh3)4 (11 mg, 0.0099 mmol), and 2-thiazolezinc bromide (1 mL, 0.5 M in THF). The solution was heated to 90° C. and stirred for 10 hours. The crude reaction was subsequently purified by preparative TLC to produce 4-tert-butyl-N-(4-chloro-2-(5-methyl-4-(thiazol-2-yl)-1H-1,2,3-triazol-1-yl)phenyl)benzenesulfonamide: MS (ES) M+H expected 488.1, found 488.4.

General Procedure JJ

Example

1-[2-(4-tert-Butyl-benzenesulfonylamino)-5-chloro-phenyl]-5-methyl-1H-[1,2,3]triazole-4-carboxylic acid

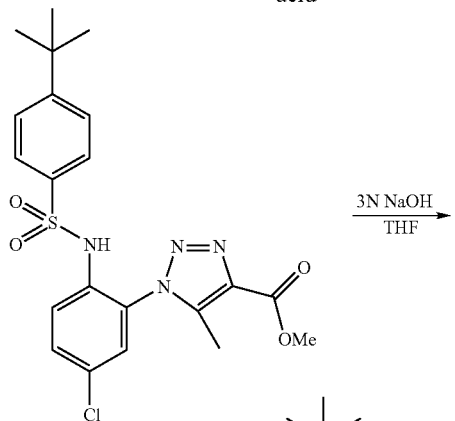

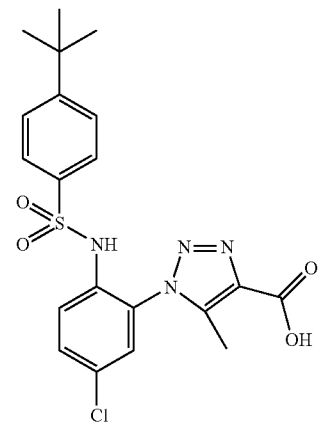

3 N NaOH (0.1 mL) was added to 1-[2-(4-tert-butyl-benzenesulfonylamino)-5-chloro-phenyl]-5-methyl-1H-[1,2,3]triazole-4-carboxylic acid methyl ester (synthesized according to general procedure GG, 22 mg, 0.047 mmol) in THF and the resultant reaction mixture stirred at 60° C. overnight. The following day, the reaction mixture was concentrated to dryness and purified by preparative TLC to generate the title compound: MS (ES) M+H expected 449.1, found 449.3.

General Procedure KK

Example 4-tert-Butyl-N-[4-chloro-2-(5-methyl-4-oxazol-2-yl-[1,2,3]triazol-1-yl)-phenyl]-benzenesulfonamide

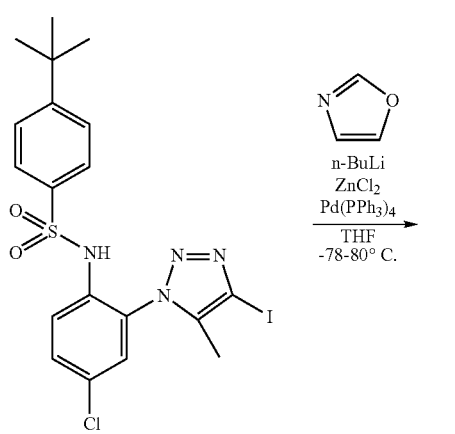

-continued

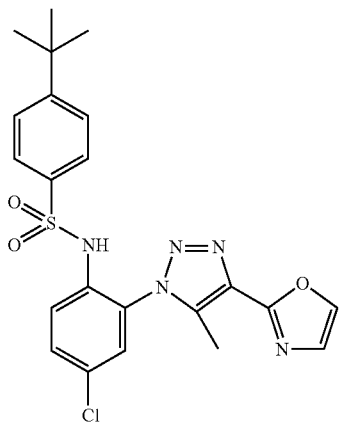

To a cooled (−78° C.) solution of n-BuLi (0.5 mL, 2.5 M solution in hexanes) in THF (3 mL) was added oxazole (0.1 mL, 1.5 mmol) via dropwise addition and the solution was stirred for 30 minutes. $ZnCl_2$ solution (3.9 mL, 0.5 M in THF) was then added and the reaction mixture was warmed to room temperature and stirred an additional 2 hours. $Pd(PPh_3)_4$ (20 mg, 0.015 mmol) and 4-tert-butyl-N-[4-chloro-2-(4-iodo-5-methyl-[1,2,3]triazol-1-yl)-phenyl]-benzenesulfonamide (synthesized according to general procedure P, 77 mg, 0.15 mmol) were then added and the reaction mixture was heated at 80° C. overnight. The reaction mixture was subsequently diluted with EtOAc (25 mL) and the combined organics were washed with water (20 mL), dried ($Na_2SO_4$), and concentrated in vacuo. The crude product was purified by preparative TLC to afford the title compound: MS (ES) M+H expected 472.1, found 472.0.

General Procedure LL

Example 4-tert-Butyl-N-[4-chloro-2-(4-hydroxymethyl-pyrazol-1-yl)-phenyl]-benzenesulfonamide

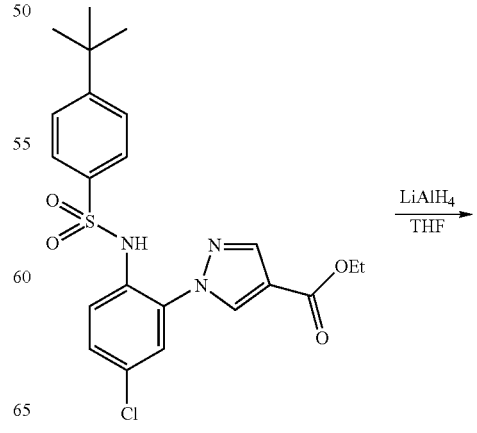

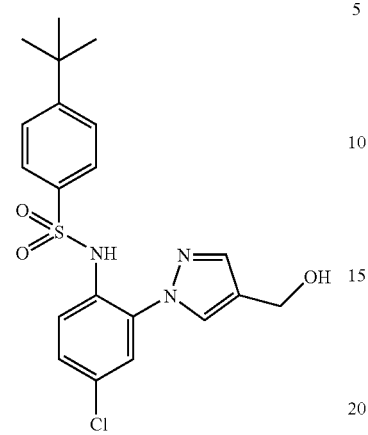

To an ice cold solution of 1-[2-(4-tert-butyl-benzenesulfonylamino)-5-chloro-phenyl]-1H-pyrazole-4-carboxylic acid ethyl ester (synthesized according to general procedure D, 220 mg, 0.47 mmol) in THF (5 mL) was added LiAlH$_4$ (1.0 mL, 2.4 M solution in THF) dropwise and the resultant reaction mixture was stirred for one hour at room temperature. Saturated Na$_2$SO$_4$ solution (3 mL) was subsequently added slowly at 0° C. and the precipitated solid was filtered through celite and washed thoroughly with EtOAc (100 mL). The filtrate was dried over Na$_2$SO$_4$, concentrated in vacuo, and purified by automated flash chromatography to afford the title compound: MS (ES) M+H expected 420.1, found 420.1.

General Procedure MM

Example 4-tert-Butyl-N-[4-chloro-2-(4-methylaminomethyl-pyrazol-1-yl)-phenyl]-benzenesulfonamide

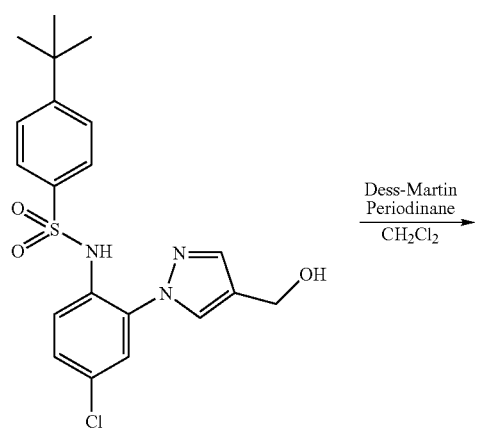

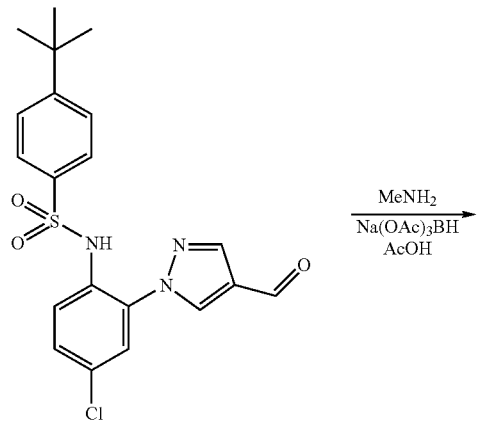

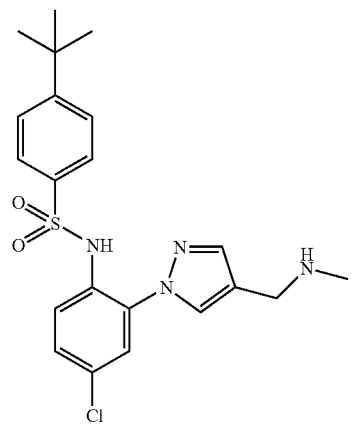

Step 1: To a solution of 4-tert-butyl-N-[4-chloro-2-(4-hydroxymethyl-pyrazol-1-yl)-phenyl]-benzenesulfonamide (synthesized according to general procedure LL, 31 mg, 0.074 mmol) in CH$_2$Cl$_2$ (3 mL) was added Dess-Martin periodinane (34 mg, 0.33 mmol) and the reaction was stirred for 3 hours at room temperature. 10% Na$_2$S$_2$O$_3$ (5 mL) and saturated aqueous NaHCO$_3$ (5 mL) were added sequentially and the mixture was stirred an additional 30 minutes. The aqueous layer was subsequently separated and extracted with EtOAc (2×25 mL). The combined organic layers were washed with saturated aqueous NaHCO$_3$ solution (20 mL) and brine (20 mL), dried (anhydrous Na$_2$SO$_4$), and concentrated in vacuo to afford 4-tert-butyl-N-[4-chloro-2-(4-formyl-pyrazol-1-yl)-phenyl]-benzenesulfonamide which was used for further transformation without purification.

Step 2: The above aldehyde was converted to 4-tert-butyl-N-[4-chloro-2-(4-methylaminomethyl-pyrazol-1-yl)-phenyl]-benzenesulfonamide according to general procedure HH, step 3: MS (ES) M+H expected 433.1, found 433.4.

General Procedure NN

Example

Ethyl 1-(2-(4-tert-butylphenylsulfonamido)-5-chlorophenyl)-5-methyl-1H-pyrazole-4-carboxylate

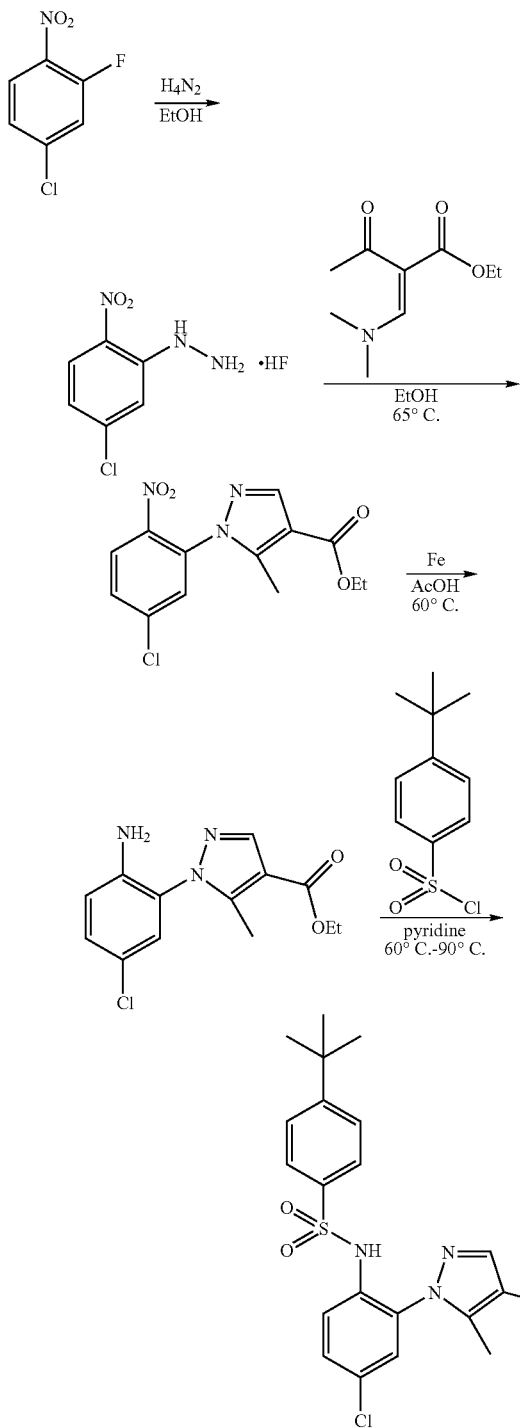

Step 1: A 20 mL vial was charged with 4-chloro-2-fluoro-1-nitrobenzene (176 mg, 1.0 mmol), hydrazine (50 µL, 1.0 mmol) and EtOH (3.0 mL). The reaction was stirred overnight, during which the product precipitated from solution. The resultant solid was filtered, washed with cold ethanol, and dried in vacuo to afford the desired aryl hydrazine as its hydrofluoride salt.

Step 2: To the above hydrazine (736 mg, 3.55 mmol) in a 25 mL round-bottom flask was added ethyl 2-((dimethylamino)methylene)-3-oxobutanoate (657 mg, 3.55 mmol) and EtOH (7 mL). The solution was heated to 65° C. and stirred overnight. The following day, the crude reaction was concentrated in vacuo and purified by column chromatography to produce the desired pyrazole.

Step 3: The bicyclic pyrazole (448 mg, 1.45 mmol) was dissolved in AcOH (15 mL) and the solution was heated to 60° C. To the rapidly stirring solution was added Fe (162 mg, 2.89 mmol) in two portions and the reaction was stirred overnight. The following day, the acetic acid was removed in vacuo and the residue was partitioned with methylene chloride and water, during which significant insoluble material persisted. The aqueous layer was extracted three times with methylene chloride, the combined organics dried over sodium sulfate, and concentrated in vacuo. The resultant residue was purified by automated silica gel chromatography to afford the desired aniline.

Step 4: The above aniline (96 mg, 0.34 mmol) was sulfonylated according to general procedure G to generate ethyl 1-(2-(4-tert-butylphenylsulfonamido)-5-chlorophenyl)-5-methyl-1H-pyrazole-4-carboxylate: MS (ES) M+H expected 476.1, found 476.4.

General Procedure OO

Example 1,1-Dimethyl-3-oxo-1,3-dihydro-isobenzofuran-5-sulfonic acid (4-chloro-2-[1,2,3]triazolo[4,5-b]pyridin-1-yl-phenyl)-amide

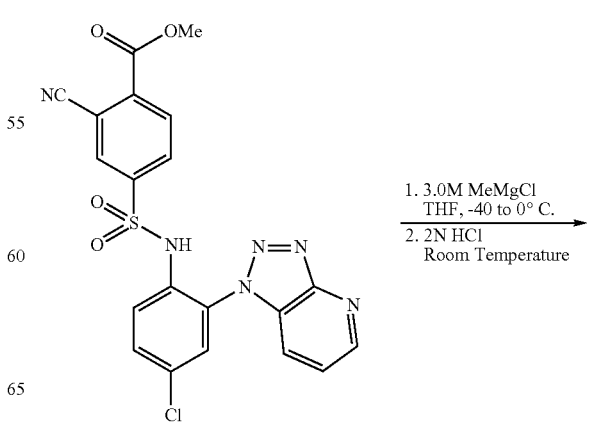

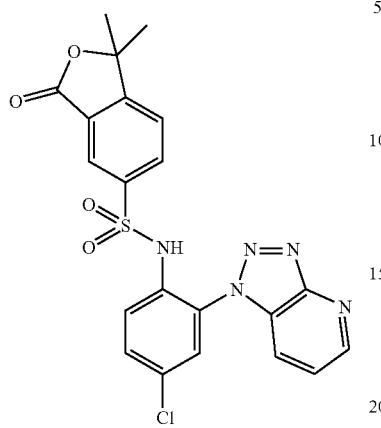

A 4 mL vial was charged with 4-(4-chloro-2-[1,2,3]triazolo[4,5-b]pyridin-1-yl-phenylsulfamoyl)-2-cyano-benzoic acid methyl ester (synthesized according to general procedure G, 23 mg, 0.05 mmol) and 1.5 mL THF. The slurry was cooled to −40° C. in a dry ice-acetonitrile bath and 3.0 M methylmagnesium chloride in Et$_2$O (83 µL, 0.25 mmol) was added dropwise. The resultant mixture was stirred five hours, during which it was warmed to 0° C. 2 N HCl (1.5 mL) was subsequently added to reaction mixture and it was stirred at room temperature overnight. The reaction mixture was then purified by reversed phase HPLC to afford 1,1-dimethyl-3-oxo-1,3-dihydro-isobenzofuran-5-sulfonic acid (4-chloro-2-[1,2,3]triazolo[4,5-b]pyridin-1-yl-phenyl)-amide: MS (ES) M+H expected 470.0, found 470.0.

General Procedure PP

Example

N-(4-Chloro-2-[1,2,3]triazolo[4,5-b]pyridin-1-yl-phenyl)-3-fluoro-4-(1-hydroxy-1-methyl-ethyl)-benzenesulfonamide sodium salt

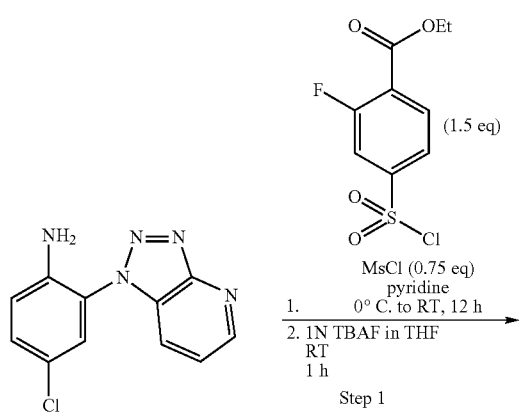

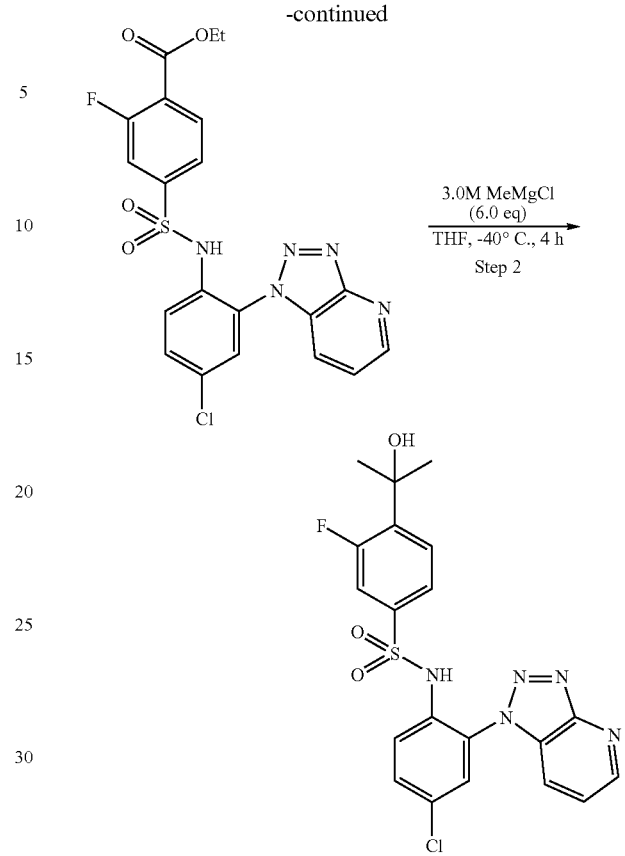

Step 1: To 4-chloro-2-[1,2,3]triazolo[4,5-b]pyridin-1-yl-phenylamine (153.5 mg, 0.626 mmol) in pyridine (2 mL) was added 4-chlorosulfonyl-2-fluoro-benzoic acid ethyl ester (200 mg, 0.752 mmol) followed by methanesulfonyl chloride (32 µL, 0.47 mmol) at 0° C. under a nitrogen atmosphere. The resultant reaction mixture was allowed to warm to room temperature and stirred for overnight. The following day, reaction mixture was diluted with EtOAc (25 mL), washed with 2N HCl (2×15 mL), dried (Na$_2$SO$_4$) and evaporated. The resulting bis-sulfonamides crude mixture was treated with 1 N TBAF (in THF, 2 mL) at room temperature for 1 hour. The reaction mixture was then diluted with EtOAc (25 mL), washed with 2 N HCl (2×15 mL), water (10 mL), brine (10 mL), dried (Na$_2$SO$_4$) and evaporated. The resulting crude product was purified by SiO$_2$ chromatography using 50→100% EtOAc in hexanes solvent system to obtain 4-(4-chloro-2-[1,2,3]triazolo[4,5-b]pyridin-1-yl-phenylsulfamoyl)-2-fluoro-benzoic acid ethyl ester.

Step 2: The title compound was prepared via conversion from its ethyl ester according to general procedure Y: MS (ES) M+Na expected 484.0, found 484.0.

Measuring Efficacy of Chemokine Modulators

In Vitro Assays

A variety of assays can be used to evaluate the compounds provided herein, including signaling assays, chemotaxis (migration assays), ligand binding assays, and other assays of cellular response. Chemokine receptor signaling assays can be used to measure the ability of a compound, such as a potential CCR9 antagonist, to block CCR9 ligand- (e.g. TECK)-induced signaling. A migration assay can be used to measure the ability of a compound of interest, such as a possible chemokine antagonist, to block chemokine-mediated cell migration in vitro. The latter is believed to resemble chemokine-induced cell migration in vivo. A ligand binding assay can be used to measure the ability of a compound, such as a potential CCR9 antagonist, to block the interaction of TECK with its receptor.

In a suitable assay, a chemokine protein (whether isolated or recombinant) is used which has at least one property, activity, or functional characteristic of a mammalian chemokine protein. The property can be a binding property (to, for example, a ligand or inhibitor), a signaling activity (e.g., activation of a mammalian G protein, induction of rapid and transient increase in the concentration of cytosolic free calcium ion), cellular response function (e.g., stimulation of chemotaxis or inflammatory mediator release by leukocytes), and the like.

The assay can be a cell-based assay that utilizes cells stably or transiently transfected with a vector or expression cassette having a nucleic acid sequence that encodes the chemokine receptor. Cell lines naturally expressing the chemokine can also be used. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., TECK) as a competitor.

Binding inhibition assays can be used to evaluate the present compounds. In these assays, the compounds are evaluated as inhibitors of ligand binding using, for example, TECK. In another embodiment, the CCR9 receptor is contacted with a ligand such as TECK and a measure of ligand binding is made. The receptor is then contacted with a test agent in the presence of a ligand (e.g., TECK) and a second measurement of binding is made. A reduction in the extent of ligand binding is indicative of inhibition of binding by the test agent. The binding inhibition assays can be carried out using whole cells which express the chemokine, or a membrane fraction from cells which express the chemokine.

The binding of a G protein coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote et al., Cell, 72:415-425 (1993); Van Riper et al., J. Exp. Med., 177:851-856 (1993) and Dahinden et al., J. Exp. Med., 179:751-756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present invention. Examples of suitable assays include those described in PCT/US97/15915; Springer et al., WO 94/20142; Berman et al., Immunol. Invest., 17:625-677 (1988); and Kavanaugh et al., J. Immunol., 146:4149-4156 (1991)).

Calcium signaling assays measure calcium concentration over time, preferably before and after receptor binding. These assays can be used to quantify the generation of a receptor-signaling mediator, $Ca^{++}$, following receptor binding (or absence thereof). These assays are useful in determining the ability of a compound, such as those of the present invention, to generate the receptor signaling mediator by binding to a receptor of interest. Also, these assays are useful in determining the ability of a compound, such as those of the present invention, to inhibit generation of the receptor signaling mediator by interfering with binding between a receptor of interest and a ligand.

In calcium signaling assays used to determine the ability of a compound to interfere with binding between a chemokine receptor and a known chemokine ligand, chemokine receptor-expressing cells (CCR9-expressing cells such as T cell line MOLT-4 cells) are first incubated with a compound of interest, such as a potential chemokine antagonist, at increasing concentrations. The cell number can be from $10^5$ to $5\times10^5$ cells per well in a 96-well microtiter plate. The concentration of the compound being tested may range from 0 to 100 µM. After a period of incubation (which can range from 5 to 60 minutes), the treated cells are placed in a Fluorometric Imaging Plate Reader (FLIPR®) (available from Molecular Devices Corp., Sunnyvale, Calif.) according to the manufacturer's instruction. The FLIPR® system is well known to those skilled in the art as a standard method of performing assays. The cells are then stimulated with an appropriate amount of the chemokine ligand (TECK for CCR9) at 5-100 nM final concentration, and the signal of intracellular calcium increase (also called calcium flux) is recorded. The efficacy of a compound as an inhibitor of binding between the chemokine and the ligand can be calculated as an $IC_{50}$ (the concentration needed to cause 50% inhibition in signaling) or $IC_{90}$ (at 90% inhibition).

In vitro cell migration assays can be performed (but are not limited to this format) using the 96-well microchamber (called ChemoTX™). The ChemoTX™ system is well known to those skilled in the art as a type of chemotactic/cell migration instrument. In this assay, CCR9-expressing cells (such as MOLT-4) are first incubated with a compound of interest, such as a possible CCR9 antagonist at increasing concentrations. Typically, fifty thousand cells per well are used, but the amount can range from $10^3$-$10^6$ cells per well. The chemokine ligand (for example, CCR9 ligand TECK, typically at 50 nM (but can range from 5-100 nM)), is placed at the lower chamber and the migration apparatus is assembled. Twenty microliters of test compound-treated cells are then placed onto the membrane. Migration is allowed to take place at 37° C. for a period of time, typically 2.5 hours for CCR9. At the end of the incubation, the number of cells that migrated across the membrane into the lower chamber is then quantified. The efficacy of a compound as an inhibitor of chemokine-mediated cell migration is calculated as an $IC_{50}$ (the concentration needed to reduce cell migration by 50%) or $IC_{90}$ (for 90% inhibition).

In Vivo Efficacy Models for Human IBD

T cell infiltration into the small intestine and colon have been linked to the pathogenesis of human inflammatory bowel diseases which include Coeliac disease, Crohn's disease and ulcerative colitis. Blocking trafficking of relevant T cell populations to the intestine is believed to be an effective approach to treat human IBD. CCR9 is expressed on gut-homing T cells in peripheral blood, elevated in patients with small bowel inflammation such as Crohn's disease and Coeliac disease. CCR9 ligand TECK is expressed in the small intestine. It is thus believed that this ligand-receptor pair plays a role in IBD development by mediating migration of T cells to the intestine. Several animal models exist and can be used for evaluating compounds of interest, such as potential CCR9 antagonists, for an ability to affect such T cell migration and/or condition or disease, which might allow efficacy predictions of antagonists in humans.

Animal Models with Pathology Similar to Human Ulcerative Colitis

A murine model described by Panwala and coworkers (Panwala et al., J. Immunol., 161(10):5733-44 (1998)) involves genetic deletion of the murine multi-drug resistant gene (MDR). MDR knockout mice (MDR−/−) are susceptible to developing a severe, spontaneous intestinal inflammation when maintained under specific pathogen-free facility conditions. The intestinal inflammation seen in MDR−/− mice has a pathology similar to that of human inflammatory bowel disease (IBD) and is defined by Th1 type T cells infiltration into the lamina propria of the large intestine.

Another murine model was described by Davidson et al., *J Exp Med.*, 184(1):241-51 (1986). In this model, the murine IL-10 gene was deleted and mice rendered deficient in the production of interleukin 10 (IL-10−/−). These mice develop a chronic inflammatory bowel disease (IBD) that predominates in the colon and shares histopathological features with human IBD.

Another murine model for IBD has been described by Powrie et al., *Int. Immunol.*, 5(11):1461-71 (1993), in which a subset of CD4+ T cells (called CD45RB (high)) from immunocompetent mice are purified and adoptively transferred into immunodeficient mice (such as C.B-17 scid mice). The animal restored with the CD45RBhighCD4+ T cell population developed a lethal wasting disease with severe mononuclear cell infiltrates in the colon, pathologically similar with human IBD.

Murine Models with Pathology Similar to Human Crohn's Disease

The TNF ARE(−/−) model. The role of TNF in Crohn's disease in human has been demonstrated more recently by success of treatment using anti-TNF alpha antibody by Targan et al., N. Engl. J Med., 337(15):1029-35 (1997). Mice with aberrant production of TNF-alpha due to genetic alteration in the TNF gene (ARE−/−) develop Crohn's-like inflammatory bowel diseases (see Kontoyiannis et al., Immunity, 10(3):387-98 (1999)).

The SAMP/yit model. This model is described by Kosiewicz et al., *J Clin. Invest.*, 107(6):695-702 (2001). The mouse strain, SAMP/Yit, spontaneously develops a chronic inflammation localized to the terminal ileum. The resulting ileitis is characterized by massive infiltration of activated T lymphocytes into the lamina propria, and bears a remarkable resemblance to human Crohn's disease.

Examples of In Vitro Assay

Reagents

MOLT-4 cells were obtained from the American Type Culture Collection (Manassas, Va.) and cultured in RPMI tissue culture medium supplemented with 10% fetal calf serum (FCS) in a humidified 5% $CO_2$ incubator at 37° C. Recombinant human chemokine proteins TECK was obtained from R&D Systems (Minneapolis, Minn.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).

Chemotaxis Assay

Chemotaxis assay was used to determine the efficacy of potential receptor antagonists in blocking migration mediated through chemokines (such as CCR9). This assay was routinely performed using the ChemoTX® microchamber system with a 5-µm pore-sized polycarbonate membrane. To begin such an assay, chemokine expressing cells (such as MOLT-4 cells for CCR9 assay) were harvested by centrifugation of cell suspension at 1000 RPM on a GS-6R Beckman centrifuge. The cell pellet was resuspended in chemotaxis buffer (HBSS with 0.1% BSA) at $5\times10^6$ cells/mL for CCR9 assay. Test compounds at desired concentrations were prepared from 10 mM stock solutions by serial dilutions in chemotaxis buffer. An equal volume of cells and compounds were mixed and incubated at room temperature for 15 minutes. Afterwards, 20 µL of the mixture was transferred onto the porous membrane of a migration microchamber, with 29 µL of chemokine ligand (50 nm chemokine TECK protein for CCR9 assay) placed at the lower chamber. Following an incubation at 37° C. (150-minute for CCR9), during which cells migrated against the chemokine gradient, the assay was terminated by removing the cell drops from atop the filter. To quantify cells migrated across the membrane, 5 µL of 7× CYQUANT® solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. $IC_{50}$ calculation was further performed by non-linear squares regression analysis using Graphpad Prism (Graphpad Software, San Diego, Calif.).

In Vivo Efficacy

A 17-day study of type II collagen-induced arthritis is conducted to evaluate the effects of a modulator on arthritis-induced clinical ankle swelling. Rat collagen-induced arthritis is an experimental model of polyarthritis that has been widely used for preclinical testing of numerous anti-arthritic agents (see Trentham et al., J. Exp. Med. 146(3):857-868 (1977), Bendele et al., *Toxicologic Pathol.* 27:134-142 (1999), Bendele et al., *Arthritis. Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17-day study. The test modulator is dosed daily by sub-cutaneous injection from day 9 to day 17 at a dose of 100 mg/kg and a volume of 1 mL/kg in the following vehicle (24.5% Cremaphore EL, 24.5% common oil, 1% Benzylalcohol and 50% Distilled water). Caliper measurements of the ankle joint diameter are taken daily, and reducing joint swelling is taken as a measure of efficacy.

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities.

In a study using the MDR1a-knockout mice, a CCR9 antagonist is evaluated by prophylactic administration for its ability to delay disease onset. Female mice (n=34) are dosed with 50 mg/kg twice a day by subcutaneous injections for 14 consecutive weeks starting at age 10 weeks. The study is evaluated for IBD-associated growth retardation.

Evaluation of a Test Modulator in a Rat Model of Thioglycollate-induced Peritoneal Inflammation A 2-day study of thioglycollate-induced inflammation is conducted to evaluate the effects of the test modulator. The hallmarks of this model are reliable onset and progression of robust, easily measurable inflammatory cellular infiltrate. For the induction of inflammatory peritonitis in Lewis rats, Brewer-Thioglycollate (1.0 mL, 4% solution in distilled water) is injected intra peritoneal (i.p.). Before this injection, the treatment group received test modulator or vehicle and the control group received the same volume of PBS as i.p. injection. After 2 days, a peritoneal lavage is performed with ice-cold PBS (phosphate-buffered saline) containing 1 mM EDTA. The recovered cells are counted with a cell counter (Coulter Counter; Coulter Pharmaceutical, Palo Alto, Calif.) and monocytes/macrophages were identified by flow cytometry using light-scatter properties.

Evaluation of a Test Modulator in a Mouse Model of Bacterial Infection

A 1-day study of *streptococcus pneumoniae* infection is conducted to evaluate the effects of the test modulator. The model measures bacterial infection and spread in an animal following pulmonary infection with live bacterial cultures, measured by inflammatory cellular infiltrate, and assessment of bacterial burden. C57/B6 mice are inoculated intra nasally with LD50 400 CFU at day 0. Groups are either test modulator or vehicle control treated 1 day prior to bacterial inoculation and twice daily throughout the study. Bacterial burden is measured at 24 hours by plating serial dilutions of homogenized lung tissue on agar plates and counting colonies.

It is therefore intended that the foregoing detailed description be regarded as illustrative rather than limiting, and that it be understood that it is the following claims, including all equivalents, that are intended to define the spirit and scope of this invention.

The invention claimed is:

1. A compound that is N-(4-Chloro-2-[1,2,3]triazolo[4,5-b]pyridin-1-yl-phenyl)-4-(1-hydroxy-1-methyl-ethyl)-benzene-sulfonamide, or a salt thereof.

2. A compound that is N-(4-Chloro-2-[1,2,3]triazolo[4,5-b]pyridin-1-yl-phenyl)-4-(1-hydroxy-1-methyl-ethyl)-benzene-sulfonamide.

3. A compound that is N-(4-Chloro-2-[1,2,3]triazolo[4,5-b]pyridin-1-yl-phenyl)-4-(1-hydroxy-1-methyl-ethyl)-benzene-sulfonamide sodium salt.

4. A composition comprising a pharmaceutically acceptable carrier and a compound of claim 1.

5. A composition comprising a pharmaceutically acceptable carrier and a compound of claim 2.

6. A composition comprising a pharmaceutically acceptable carrier and a compound of claim 3.

* * * * *